(12) United States Patent
Shimamura et al.

(10) Patent No.: US 7,548,636 B2
(45) Date of Patent: Jun. 16, 2009

(54) ORGANISM RECOGNITION SYSTEM

(75) Inventors: Toshishige Shimamura, Kanagawa (JP);
Hiroki Morimura, Kanagawa (JP);
Satoshi Shigematsu, Kanagawa (JP);
Norio Sato, Kanagawa (JP); Masami Urano, Kanagawa (JP); Katsuyuki Machida, Kanagawa (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 753 days.

(21) Appl. No.: 10/520,879

(22) PCT Filed: Aug. 12, 2004

(86) PCT No.: PCT/JP2004/011605

§ 371 (c)(1),
(2), (4) Date: Jan. 7, 2005

(87) PCT Pub. No.: WO2005/016146

PCT Pub. Date: Feb. 24, 2005

(65) Prior Publication Data

US 2006/0034493 A1 Feb. 16, 2006

(30) Foreign Application Priority Data

| | | | |
|---|---|---|---|
| Aug. 15, 2003 | (JP) | ............................. | 2003-293806 |
| Sep. 5, 2003 | (JP) | ............................. | 2003-314557 |
| Sep. 5, 2003 | (JP) | ............................. | 2003-314565 |
| Nov. 27, 2003 | (JP) | ............................. | 2003-397004 |

(51) Int. Cl.
*G06K 9/00* (2006.01)
*G06F 7/04* (2006.01)

(52) U.S. Cl. ........................ 382/115; 382/124; 340/5.82

(58) Field of Classification Search .................. 382/115
See application file for complete search history.

(56) References Cited

U.S. PATENT DOCUMENTS

| | | | | |
|---|---|---|---|---|
| 3,639,905 | A * | 2/1972 | Yaida et al. ................. | 340/5.82 |
| 4,394,773 | A * | 7/1983 | Ruell .......................... | 382/124 |
| 4,771,268 | A * | 9/1988 | Sone et al. .................... | 341/22 |
| 5,311,550 | A * | 5/1994 | Fouche et al. ............... | 375/260 |
| 5,325,442 | A * | 6/1994 | Knapp ........................ | 382/124 |
| 5,541,580 | A * | 7/1996 | Gerston et al. ........... | 340/573.4 |

(Continued)

FOREIGN PATENT DOCUMENTS

JP      08-23885 B     3/1996

(Continued)

*Primary Examiner*—Bhavesh M Mehta
*Assistant Examiner*—David P Rashid
(74) *Attorney, Agent, or Firm*—Blakely, Sokoloff, Taylor & Zafman

(57) ABSTRACT

A response signal generating unit (3) applies a predetermined supply signal (2S) to a detection element (1) and outputs, as a response signal (3S), a signal which has changed in accordance with the impedance of an object (10) with which the unit is in contact through the detection element (1). A waveform information detection unit (4) detects waveform information corresponding to the impedance of the object (10) on the basis of the response signal (3S) from the response signal generating unit (3), and outputs a detection signal (4S) representing the waveform information. A biometric recognition unit (5) determines on the basis of the detection signal (4S) from the waveform information detection unit (4) whether or not the object (10) is a living body.

13 Claims, 35 Drawing Sheets

U.S. PATENT DOCUMENTS

| | | | |
|---|---|---|---|
| 5,594,806 A * | 1/1997 | Colbert | 382/115 |
| 5,745,046 A * | 4/1998 | Itsumi et al. | 340/5.83 |
| 5,936,379 A * | 8/1999 | Matsuoka | 318/810 |
| 5,990,804 A * | 11/1999 | Koyama | 340/5.82 |
| 6,011,860 A * | 1/2000 | Fujieda et al. | 382/126 |
| 6,144,757 A * | 11/2000 | Fukuzumi | 382/124 |
| 6,175,641 B1 * | 1/2001 | Kallo et al. | 382/124 |
| 6,181,808 B1 * | 1/2001 | Fukuzumi | 382/126 |
| 6,314,195 B1 * | 11/2001 | Fukuzumi | 382/115 |
| 6,501,284 B1 * | 12/2002 | Gozzini | 324/681 |
| 6,647,133 B1 * | 11/2003 | Morita et al. | 382/124 |
| 6,898,299 B1 * | 5/2005 | Brooks | 382/115 |
| 6,914,517 B2 * | 7/2005 | Kinsella | 340/5.83 |
| 7,184,581 B2 * | 2/2007 | Johansen et al. | 382/124 |
| 2001/0053535 A1 * | 12/2001 | Bashir et al. | 435/34 |
| 2003/0036054 A1 * | 2/2003 | Ladisch et al. | 435/5 |
| 2003/0044051 A1 * | 3/2003 | Fujieda | 382/124 |
| 2003/0072475 A1 * | 4/2003 | Tamori | 382/124 |
| 2003/0157587 A1 * | 8/2003 | Gomez et al. | 435/30 |

FOREIGN PATENT DOCUMENTS

| | | |
|---|---|---|
| JP | 9-19420 | 1/1997 |
| JP | 09-259272 A | 10/1997 |
| JP | 10-75936 | 3/1998 |
| JP | 10-165382 A | 6/1998 |
| JP | 10-240942 A | 9/1998 |
| JP | 10-289304 A | 10/1998 |
| JP | 10-290796 A | 11/1998 |
| JP | 11-185020 A | 7/1999 |
| JP | 2000-020684 A | 1/2000 |
| JP | 2000-98048 | 4/2000 |
| JP | 2000-172833 A | 6/2000 |
| JP | 2001-000422 A | 1/2001 |
| JP | 2002-112975 | 4/2002 |
| JP | 2002-112980 A | 4/2002 |
| JP | 2002-162204 A | 6/2002 |
| JP | 2002-520079 A | 7/2002 |
| JP | 2002-279413 A | 9/2002 |
| JP | 2003-10138 | 1/2003 |
| JP | 2003-075135 A | 3/2003 |
| JP | 2003-111749 A | 4/2003 |
| WO | WO-01-94902 | 12/2001 |

* cited by examiner

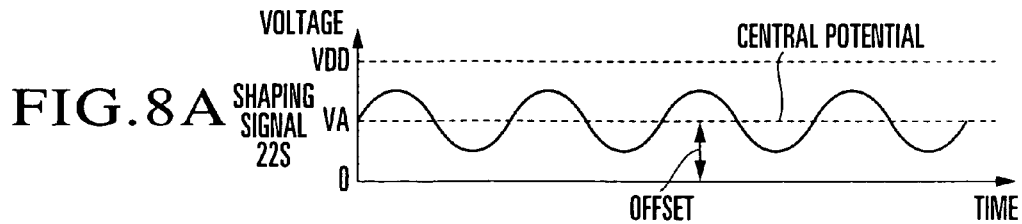
FIG.8A SHAPING SIGNAL 22S
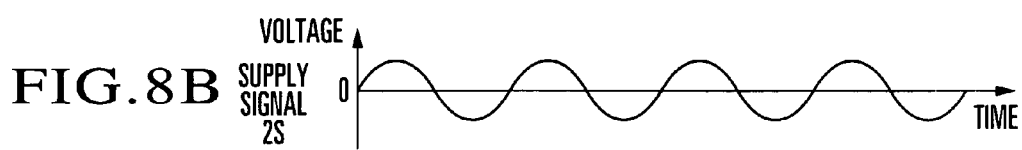
FIG.8B SUPPLY SIGNAL 2S
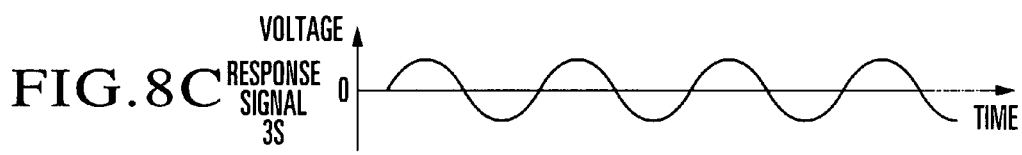
FIG.8C RESPONSE SIGNAL 3S
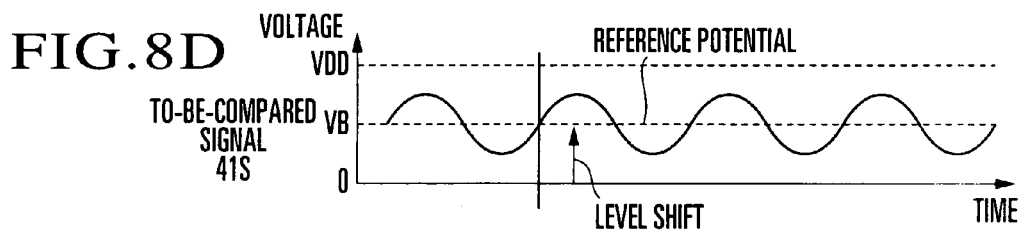
FIG.8D TO-BE-COMPARED SIGNAL 41S
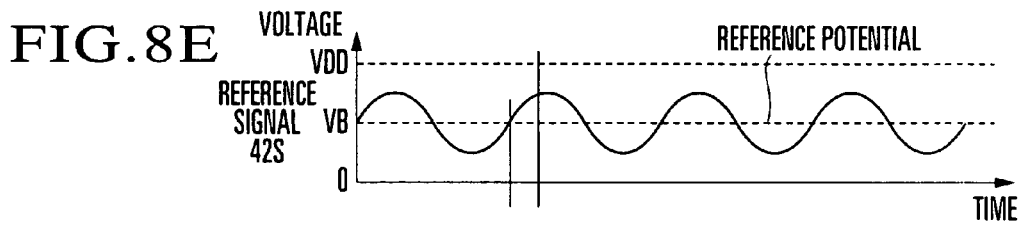
FIG.8E REFERENCE SIGNAL 42S
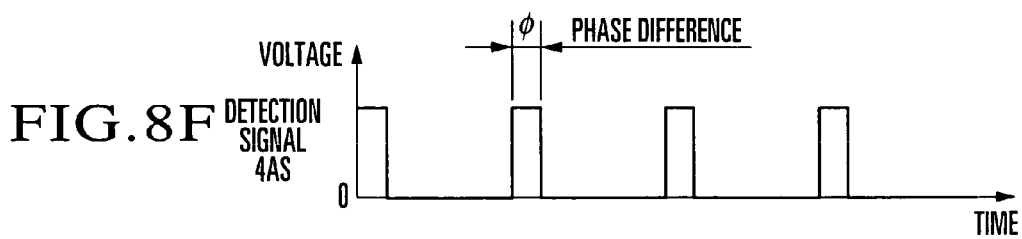
FIG.8F DETECTION SIGNAL 4AS

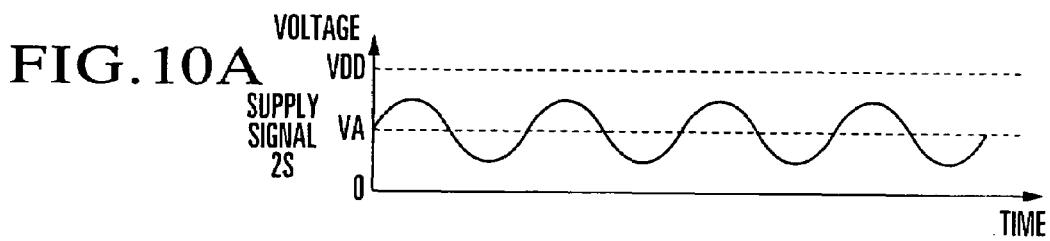
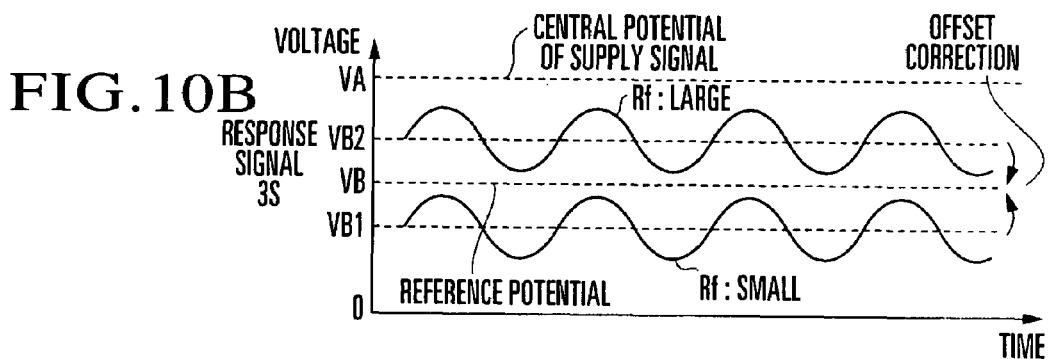
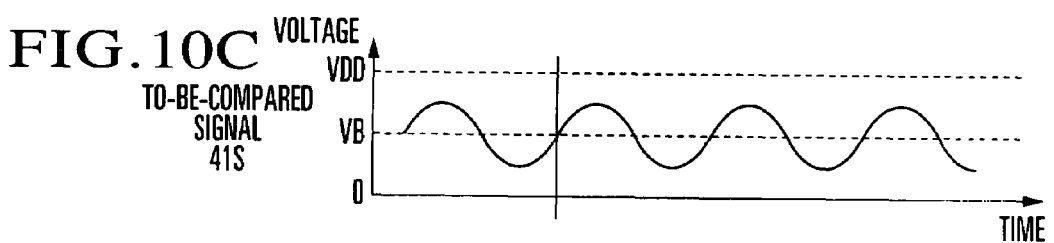
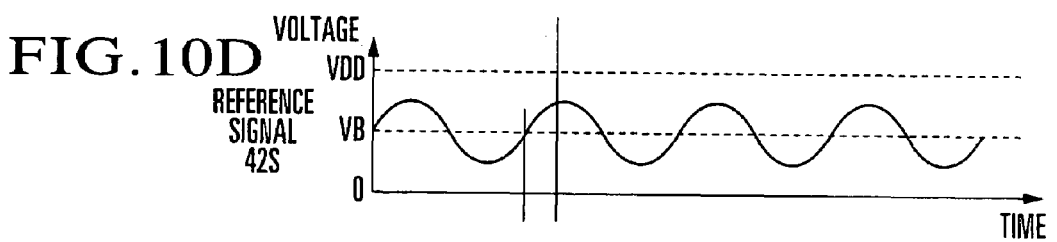
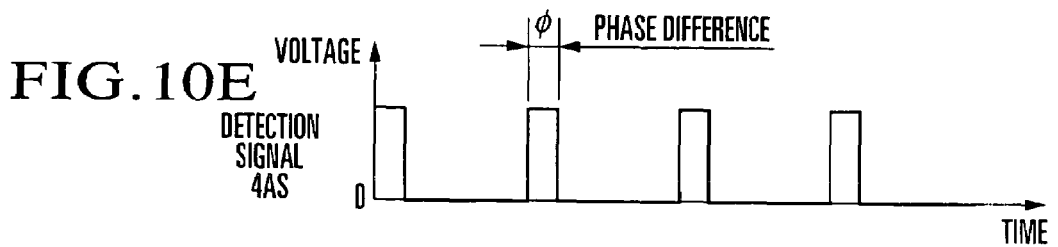

FIG. 16A
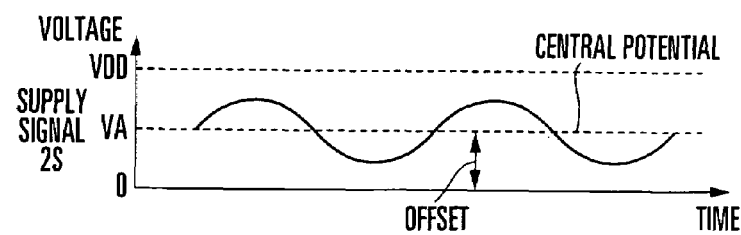
FIG. 16B
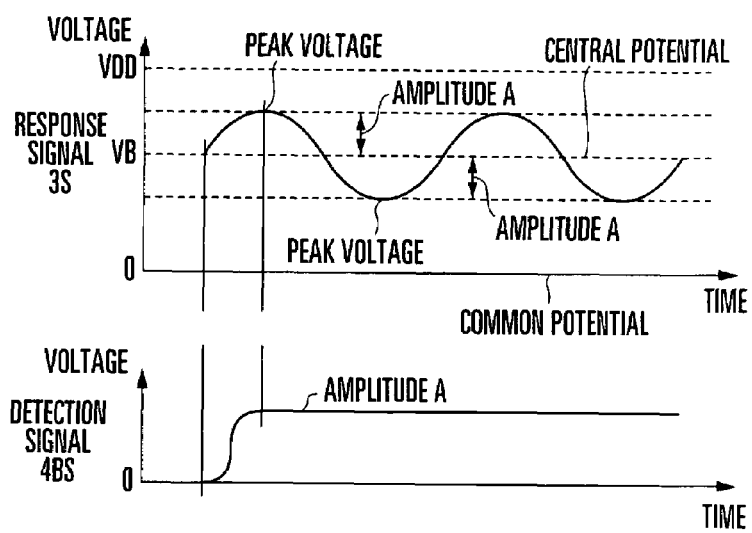
FIG. 16C
FIG. 17A
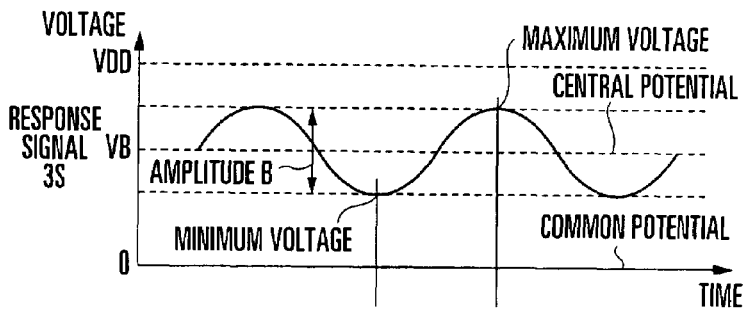
FIG. 17B

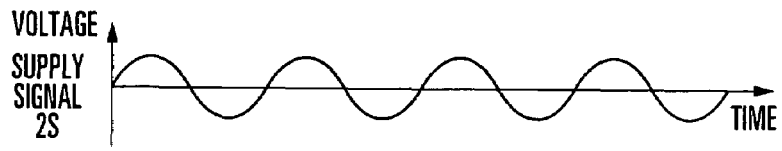
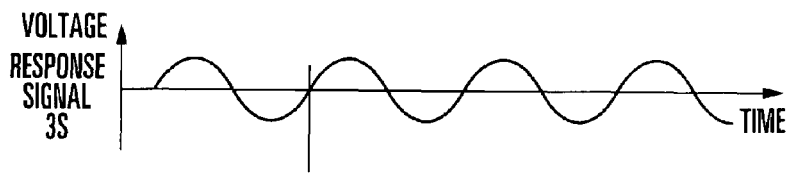
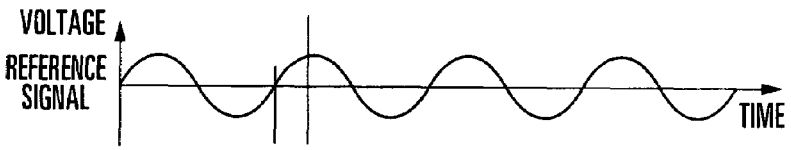
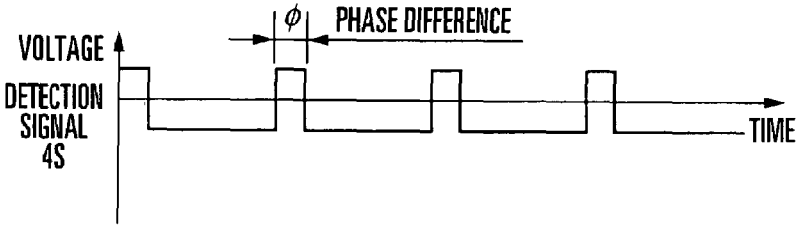
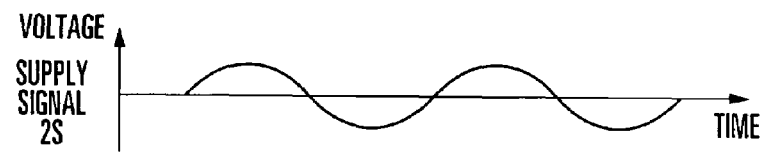
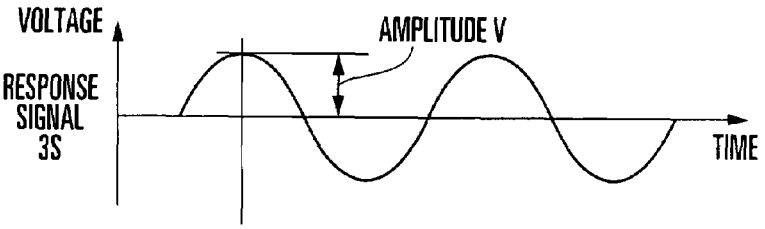
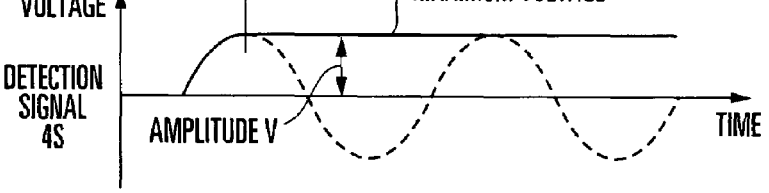

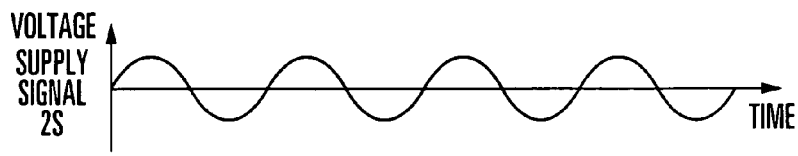
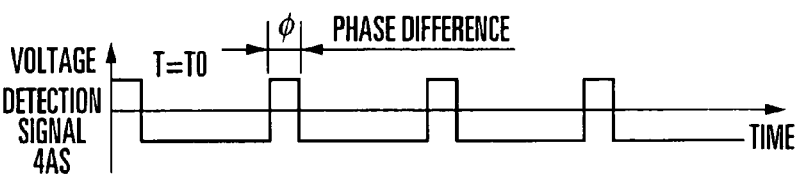
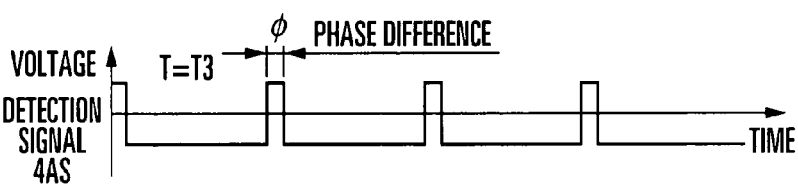
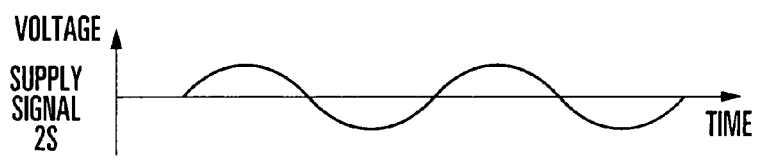
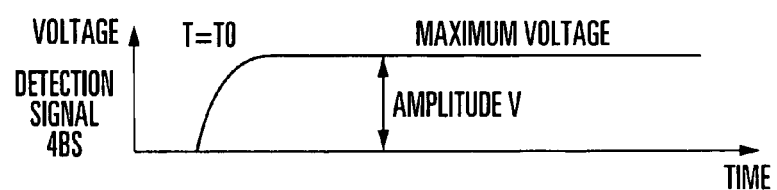
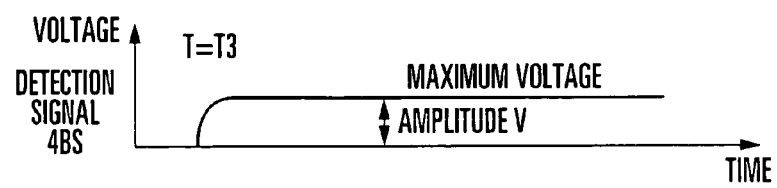

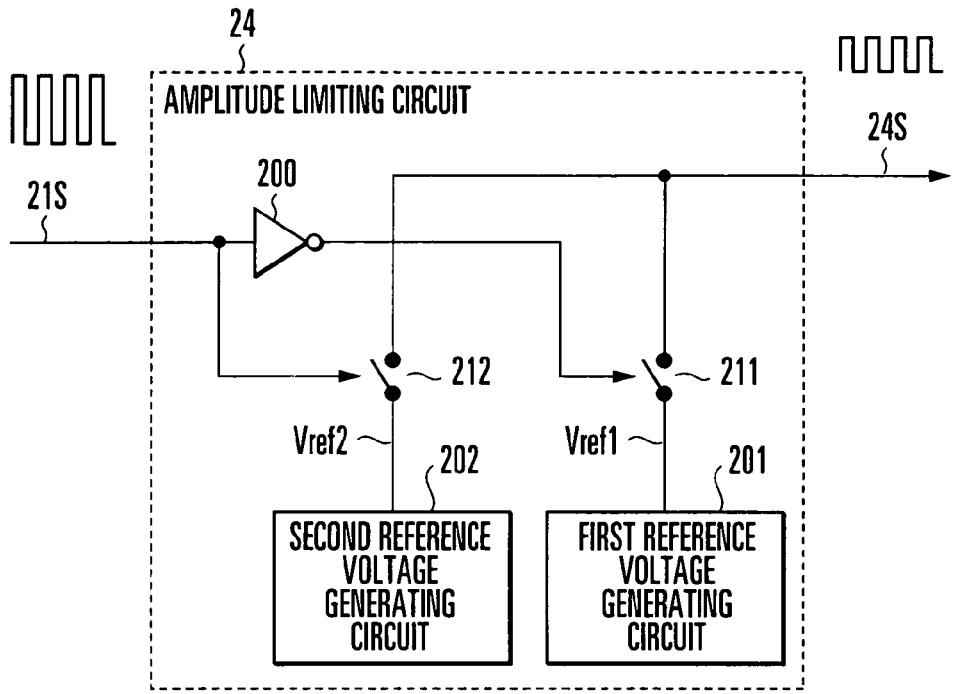
F I G. 32
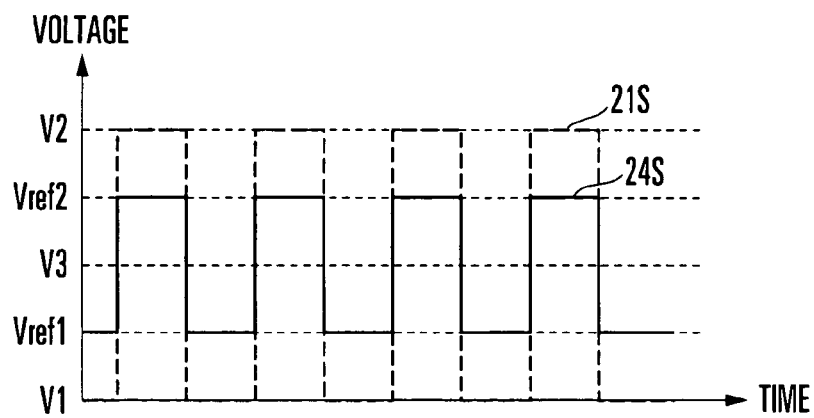
F I G. 33

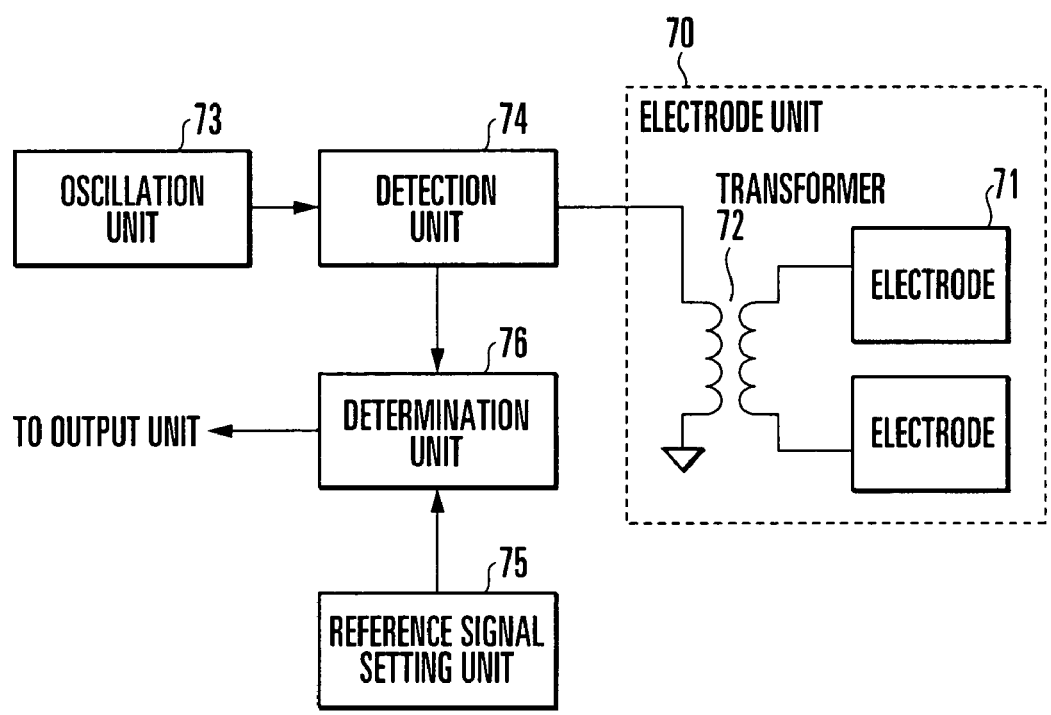
F I G. 45

ORGANISM RECOGNITION SYSTEM

TECHNICAL FIELD

The present invention relates to a technique of detecting and recognizing a living body and, more particularly, to a biometric recognition technique of determining whether or not an object is a living body, when performing individual recognition by detecting biometric information such as a fingerprint from the object.

BACKGROUND ART

With the progress of information-oriented society, techniques for the security protection of information processing systems have advanced. For example, ID cards have been used for entrance control for a computer room. However, there is a high chance that an ID card will be lost or stolen. For this reason, an individual recognition system has begun to be introduced, in which the fingerprints of individuals or the like are registered in advance instead of ID cards, and are collated at the time of entrance to the room.

In such an individual recognition system, an unauthorized person may pass a check by creating a replica of a registered fingerprint. For this reason, an individual recognition system needs to recognize whether an object is a living body, as well as performing fingerprint collation.

Conventionally, as a biometric recognition technique of detecting whether an object is a living body, a technique like that shown in FIG. 45 which uses impedance matching with an object has been proposed (see, for example, Japanese Patent Laid-Open No. 2000-172833). This biometric detection apparatus comprises an oscillation unit 73 which outputs a high-frequency signal, an electrode unit 70 of a non-resonant circuit formed from an electrode 71 to which the high-frequency signal from the oscillation unit 73 is applied and with which an object makes contact, a detection unit 74 which outputs a reflected wave signal corresponding to a change in the impedance of the electrode unit 70, a determination unit 76 which compares the reflected wave signal from the detection unit 74 with a predetermined reference signal to determine whether or not the object which contacts the electrode 71 is a living body, and a reference signal setting unit 75 in which a reference signal for determination whether or not the object is a living body is set in advance and which supplies the reference signal to the determination unit 76.

In this biometric detection apparatus, the oscillation unit 73 supplies a high-frequency signal to the electrode unit 70. The object is a living body such as a finger, and the impedance of the electrode unit 70 changes when the object contacts the electrode 71. Assume that when a human body contacts the electrode unit 70, the impedance of the object side matches the impedance on the input side of the electrode unit 70. In this case, if an object is a human body, the reflected wave of a high-frequency signal decreases due to the above impedance matching. The detection unit 74 detects this reflected wave. The determination unit 76 then compares it with the reference signal. If the reflected wave is lower than the detection level, it is determined that a human body has contacted the electrode unit.

DISCLOSURE OF INVENTION

Problems to be Solved by the Invention

Such a conventional technique, however, uses the principle of determination of a reflected wave level based on imped-ance matching, and requires external parts such as an inductance and capacitance for the detection unit 74 which detects the reflected wave of a supplied high-frequency signal in addition to a transformer 72 for impedance matching for the electrode unit 70.

A larger number of parts are therefore required. This makes it difficult to reduce the size of the apparatus, and increases the manufacturing cost. In addition, since it is easy to read out detection signals from interconnections which connect parts or estimate biometric determination conditions on the basis of the element values of external parts so as to perform fraudulent biometric recognition, satisfactory security cannot be ensured.

The present invention has been made to solve the above problems, and has as its object to provided a biometric recognition apparatus which can minutely detect an electrical characteristic of an object without requiring any inductance or capacitance such as a transformer for impedance matching to be used for the measurement of a reflected wave or increasing the apparatus size, and can easily reduce the apparatus size and form the apparatus into a chip.

Means of Solution to the Problems

A biometric recognition apparatus according to the present invention comprises a detection element which electrically contacts an object, a supply signal generating unit which generates an AC supply signal, a response signal generating unit which includes a resistive element connected between the supply signal generating unit and the detection element, applies the supply signal to the detection element through the resistive element, extracts, from one terminal of the resistive element, a response signal containing not less than one individual parameter which changes depending on whether or not the object is a living body, and outputs the signal, a waveform information detection unit which detects at least one of the individual parameters as waveform information from the response signal, and outputs a detection signal representing the waveform information, and a biometric recognition unit which determines on the basis of the detection signal whether or not the object is a living body.

Effects of the Invention

According to the present invention, a predetermined supply signal is applied to the detection element through the resistive element, and a response signal is extracted, which contains at least one individual parameter which changes depending on whether or not an object which is in contact with the apparatus through the detection element is a living body. It is then determined on the basis of the detection signal indicating at least one individual parameter from the response signal whether or not the object is a living body. This makes it possible to detect an electrical characteristic of an object by using a phase comparison circuit such as a general comparator or logic circuit, which is a very simple circuit arrangement as compared with the prior art, without requiring a resistive element or capacitive element which requires a large area. This in turn can easily realize a reduction in the size of the biometric recognition apparatus and the formation of a chip.

BRIEF DESCRIPTION OF DRAWINGS

FIGS. 8A to 8F are signal waveform charts showing signals at the respective components of the biometric recognition apparatus in FIG. 7;

FIGS. 10A to 10E are signal waveform charts showing signals at the respective components of the biometric recognition apparatus in FIG. 9;

FIGS. 16A to 16C are signal waveform charts showing signals at the respective components of the biometric recognition apparatus in FIG. 15;

FIGS. 17A and 17B are signal waveform charts showing signals at the respective components of another biometric recognition apparatus;

FIGS. 19A to 19D are signal waveform charts showing the operation of detecting a phase difference from a response signal;

FIGS. 20A to 20C are signal waveform charts showing the operation of detecting an amplitude from a response signal;

FIGS. 25A to 25C are signal waveform charts showing changes in phase difference with changes in elapse time;

FIGS. 26A to 26C are signal waveform charts showing changes in amplitude with changes in elapsed time;

FIG. 32 is a view showing an example of the arrangement of an amplitude limiting circuit used in FIG. 31;

FIG. 33 is a signal waveform chart showing the operation of the amplitude limiting circuit in FIG. 32;

FIG. 45 is a view showing an example of the arrangement of a conventional fingerprint collation apparatus.

BEST MODE FOR CARRYING OUT THE INVENTION

The embodiments of the present invention will be described next with reference to the accompanying drawings.

First Embodiment

Figure 1:
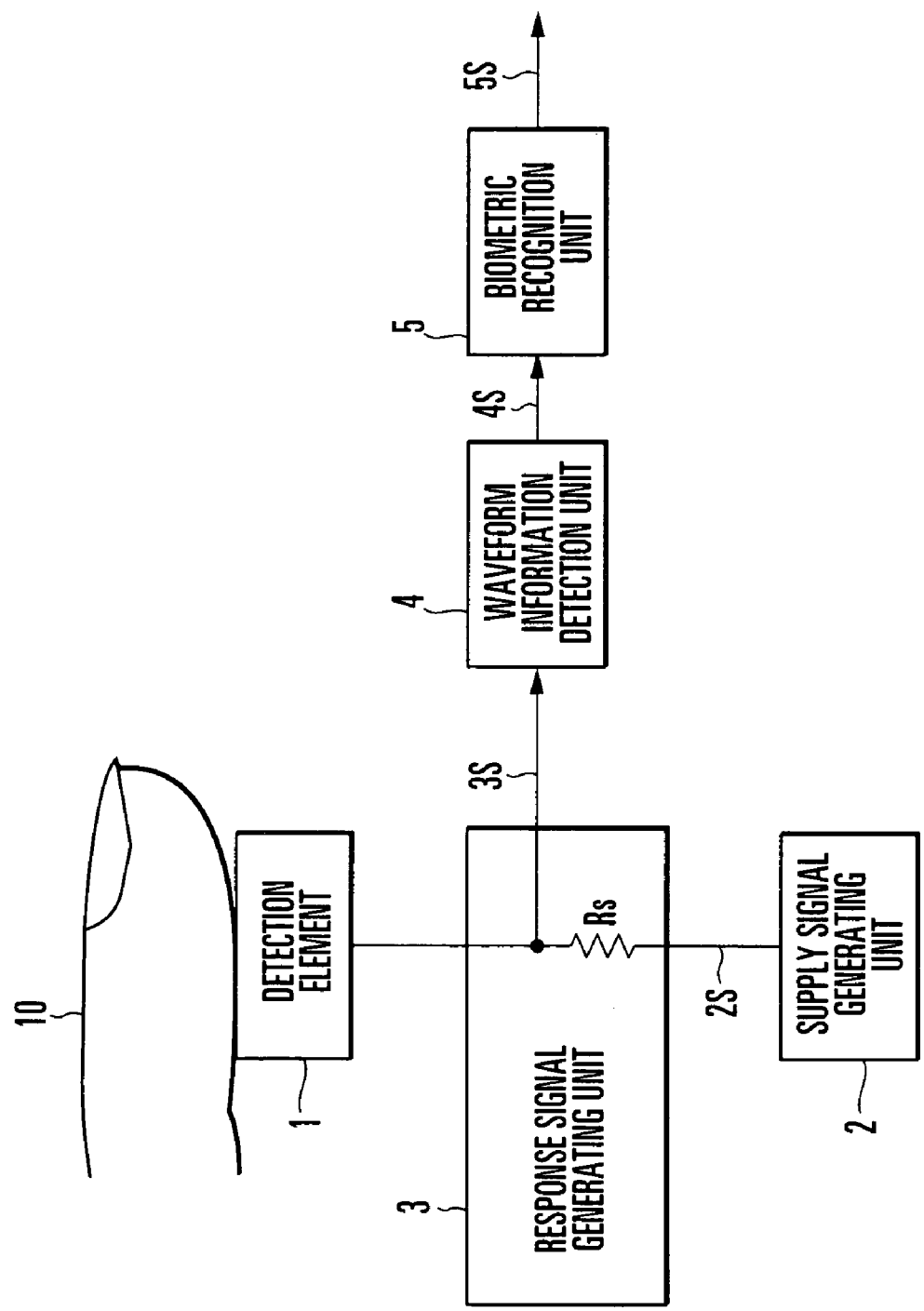
FIG. 1 is a block diagram showing the arrangement of a biometric recognition apparatus according to the first embodiment of the present invention.

A biometric recognition apparatus according to the first embodiment of the present invention will be described first with reference to FIG. 1. FIG. 1 is a block diagram showing the arrangement of the biometric recognition apparatus according to the first embodiment of the present invention.

This biometric recognition apparatus is provided with a detection element 1, supply signal generating unit 2, response signal generating unit 3, waveform information detection unit 4, and biometric recognition unit 5.

The detection element 1 electrically contacts an object 10 through a detection electrode, and connects the capacitive and resistive components of the impedance of the object 10 to the response signal generating unit 3. The supply signal generating unit 2 generates a supply signal 2S formed from a sine wave having a predetermined frequency or the like and outputs it to the response signal generating unit 3. The response signal generating unit 3 has a resistive element R connected between the supply signal generating unit 2 and the detection element 1, and applies the supply signal 2S from the supply signal generating unit 2 to the detection element 1 through the resistive element Rs. The response signal generating unit 3 then outputs, to the waveform information detection unit 4, a response signal 3S which changes in accordance with the output impedance of the detection element 1, i.e., the capacitive and resistive components of the impedance of the object 10, from one terminal of the resistive element Rs, i.e., the node between the resistive element Rs, and the detection element 1.

The waveform information detection unit 4 detects a phase difference or amplitude with respect to the supply signal 2S from the waveform represented by the response signal 3S from the response signal generating unit 3, and outputs a detection signal 4S containing waveform information representing such a phase difference or amplitude to the biometric recognition unit 5. The biometric recognition unit 5 recognizes/determines, on the basis of the waveform information contained in the detection signal 4S from the waveform information detection unit 4, whether or not the object 10 is a living body, and outputs a recognition result 5S.

The operation of the biometric recognition apparatus according to this embodiment will be described next. When the object 10 contacts the detection element 1, the supply signal 2S applied from the supply signal generating unit 2 to the detection element 1 changes in accordance with the impedance characteristic unique to the object 10, i.e., the capacitive and resistive components. The resultant signal is output as the response signal 3S to the response signal generating unit 3. The phase difference or amplitude of the response signal 3S is detected by the waveform information detection unit 4. The detection signal 4S containing information representing the detection result is then output to the biometric recognition unit 5.

The biometric recognition unit 5 recognizes/determines whether or not the object 10 is a living body, based on whether or not the waveform information contained in the detection signal 4S falls within the reference range of biometric waveform information of the authentic living body, and outputs the recognition result 5S.

As described above, in this embodiment, the waveform information detection unit 4 is provided to detect waveform information representing the phase difference or amplitude of the response signal 3S, thereby detecting information representing the real or imaginary component of the intrinsic impedance of the object 10. The biometric recognition unit 5 then determines, on the basis of the detected information, whether or not the object 10 is a living body. As compared with the prior art, therefore, an electrical characteristic of the object can be closely examined by a relatively simple circuit arrangement for detecting waveform information. This makes it possible to reduce the size of the biometric recognition apparatus and form it into a chip.

Note that in this embodiment, the phase difference or amplitude contained in the response signal 3S can be regarded as one or more individual parameters which change depending on whether the object is a living body. More specifically, the response signal generating unit 3 extracts, from one terminal of the resistive element Rs, i.e., the node between the resistive element Rs, and the detection element 1, the response signal 3S containing one or more individual parameters which change depending on whether the object is a living body. The waveform information detection unit 4 detects at least one individual parameter from the waveform of the response signal 3S as waveform information, and outputs a detection signal representing the waveform information.

In the above case, therefore, the phase and amplitude of the response signal 3S which change in accordance with the impedance of the object 10 which is in contact with the apparatus through the detection element 1 is used as an individual parameter.

The magnitude of the imaginary or real component of the object may be computed from such a phase difference or amplitude, and may be compared with the reference range of the imaginary or real components of the authentic living body. In this case, the real and imaginary components of the impedance of the object 10 which is in contact with the apparatus through the detection element 1 are used as individual parameters.

Second Embodiment

Figure 2:
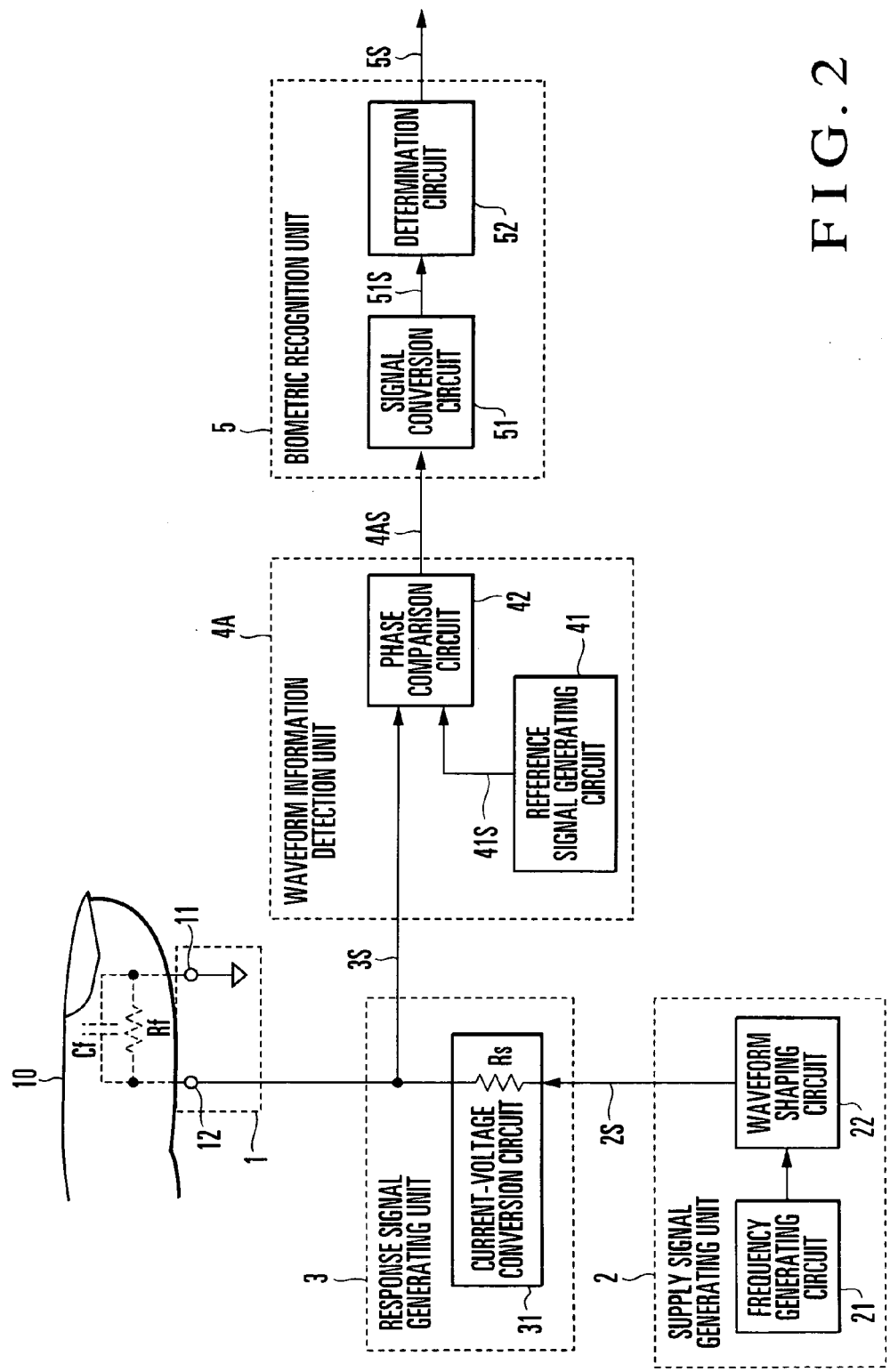
FIG. 2 is a block diagram showing the arrangement of a biometric recognition apparatus according to the second embodiment of the present invention.
Figure 3A:
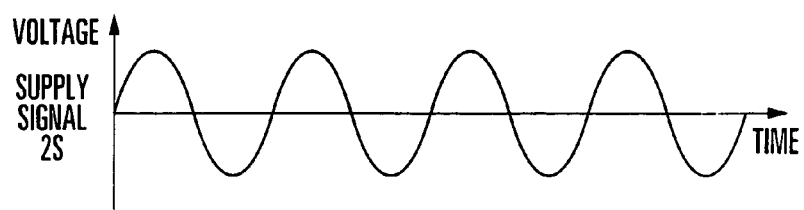
FIGS. 3A to 3D are signal waveform charts showing signals at the respective components of the biometric recognition apparatus in FIG. 2.
Figure 3B:
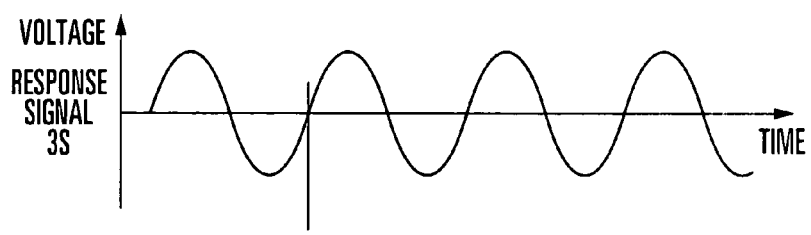
Figure 3C:
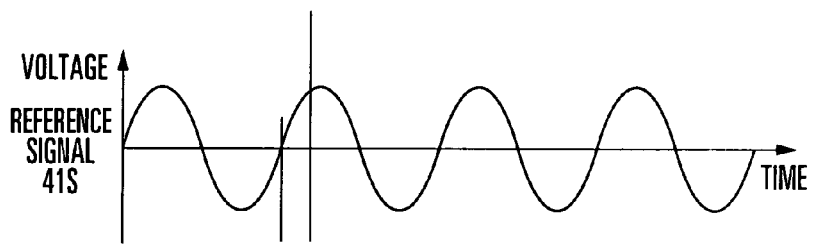
Figure 3D:
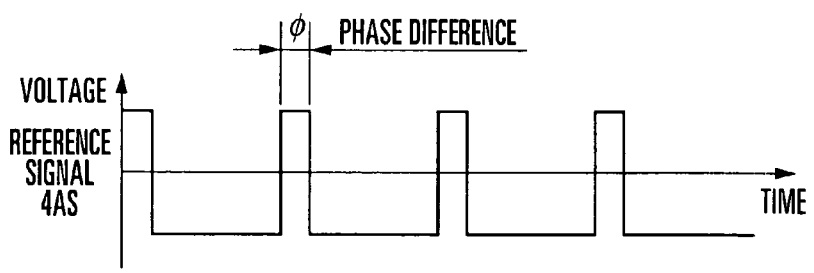

A biometric recognition apparatus according to the second embodiment of the present invention will be described next. FIG. 2 is a block diagram showing the biometric recognition apparatus according to the second embodiment of the present invention. The same reference numerals as in FIG. 1 denote the same or equivalent parts in FIG. 2.

This embodiment will exemplify a practical arrangement of the first embodiment described above, in which a waveform information detection unit 4 detects the phase difference of a response signal 3S as waveform information used for biometric recognition/determination.

Referring to FIG. 2, a detection element 1 is provided with detection electrodes 11 and 12 to electrically contact an object 10. A supply signal generating unit 2 is provided with a frequency generating circuit 21 and waveform shaping circuit 22. A response signal generating unit 3 is provided with a current-voltage conversion circuit 31. A waveform information detection unit 4A is provided with a reference signal generating circuit 42 and phase comparison circuit 42. A biometric recognition unit 5A is provided a signal conversion circuit 51 and a determination circuit 52.

In the detection element 1, the detection electrode 11 is connected to a common potential such as ground potential, and the detection electrode 12 is connected to the output stage of the current-voltage conversion circuit 31 of the response signal generating unit 3. In the supply signal generating unit 2, the frequency generating circuit 21 generates a clock signal having a predetermined frequency, and the waveform shaping circuit 22 generates and outputs a supply signal 2S formed from a sine wave or the like on the basis of a clock signal from the frequency generating circuit 21. Note that the supply signal 2S may be supplied from an external waveform generating device instead of the supply signal generating unit 2.

The current-voltage conversion circuit 31 of the response signal generating unit 3 is formed from a resistive element Rs connected between the supply signal generating unit 2 and the detection element 1. The current-voltage conversion circuit 31 applies the supply signal 2S to the object 10 with an output impedance sufficiently lower than that of the living body. The current-voltage conversion circuit 31 converts a current flowing in the object 10 through the detection element 1 at this time into a voltage, and outputs it as a response signal 3S.

The reference signal generating circuit 42 of the waveform information detection unit 4A outputs a reference signal 42S synchronized with the supply signal 2S to a phase comparison circuit 42. The phase comparison circuit 42 compares the response signal 3S with the reference signal 42S to detect an impedance characteristic unique to the object 10, a phase difference corresponding to a capacitive component in this case, and outputs it as a detection signal 4AS. In this case, the supply signal 2S may be used as the reference signal 42S.

The signal conversion circuit 51 of the biometric recognition unit 5 converts the detection signal 4AS from the phase comparison circuit 42 into a converted signal 51S which allows easy determination by the determination circuit 52. The determination circuit 52 determines whether the phase difference indicated by the converted signal 51S from the signal conversion circuit 51 falls within a phase difference reference range which indicates the impedance characteristic of the authentic living body, thereby determining whether or not the object 10 is a living body. The determination circuit 52 then outputs a recognition result 5S with respect to the object 10.

The operation of the biometric recognition apparatus in FIG. 2 will be described next. The object 10 is connected to the output stage of the current-voltage conversion circuit 31 through the detection electrodes 11 and 12 of the detection element 1. In this case, the intrinsic impedance of the object 10 can be represented by a capacitive component Cf and resistive component Rf connected between the detection electrodes 11 and 12 of the detection element 1. Therefore, the supply signal 2S applied from the current-voltage conversion circuit 31 with a predetermined output impedance is voltage-divided by the output impedance of the current-voltage conversion circuit 31 and the intrinsic impedance of the object 10. The current flowing in the object 10 then changes in phase or amplitude in accordance with the intrinsic impedance of the object 10. Such a change is converted into a voltage and output as the response signal 3S.

In this embodiment, the phase comparison circuit 42 of the waveform information detection unit 4A compares the phase of the reference signal 42S output from the reference signal generating circuit 42 with that of the response signal 3S, and outputs a detection signal 4AS containing the phase information (phase difference) of the response signal 3S.

FIGS. 3A to 3D show signal waveform examples at the respective components in FIG. 2. When a sine wave centered on a common potential such as ground potential is used as the supply signal 2S, the phase of the response signal 3S changes in accordance with the impedance of the object 10. By using a signal synchronized with the supply signal 2S as the reference signal 42S and making the phase comparison circuit 42 compare the phase of the reference signal 42S with that of the response signal 3S, for example, the detection signal 4AS having a phase difference .phi. as a pulse width is output.

Since the phase comparison circuit 42 is provided for the waveform information detection unit 4A to compare the phase of the response signal 3S with that of the reference signal 42S in this manner, a phase which changes in accordance with the intrinsic capacitive component of the object 10 can be detected as waveform information representing the waveform of the response signal 3S. This makes it possible to minutely detect an electrical characteristic of an object, information representing the imaginary component of the intrinsic impedance of the object 10 in this case, by using a phase comparison circuit such as a general comparator or logic circuit, which is a very simple circuit arrangement as compared with the prior art, without requiring a resistive element or capacitive element which requires a large area. This in turn can easily realize a reduction in the size of the biometric recognition apparatus and the formation of a chip.

Third Embodiment

Figure 4:
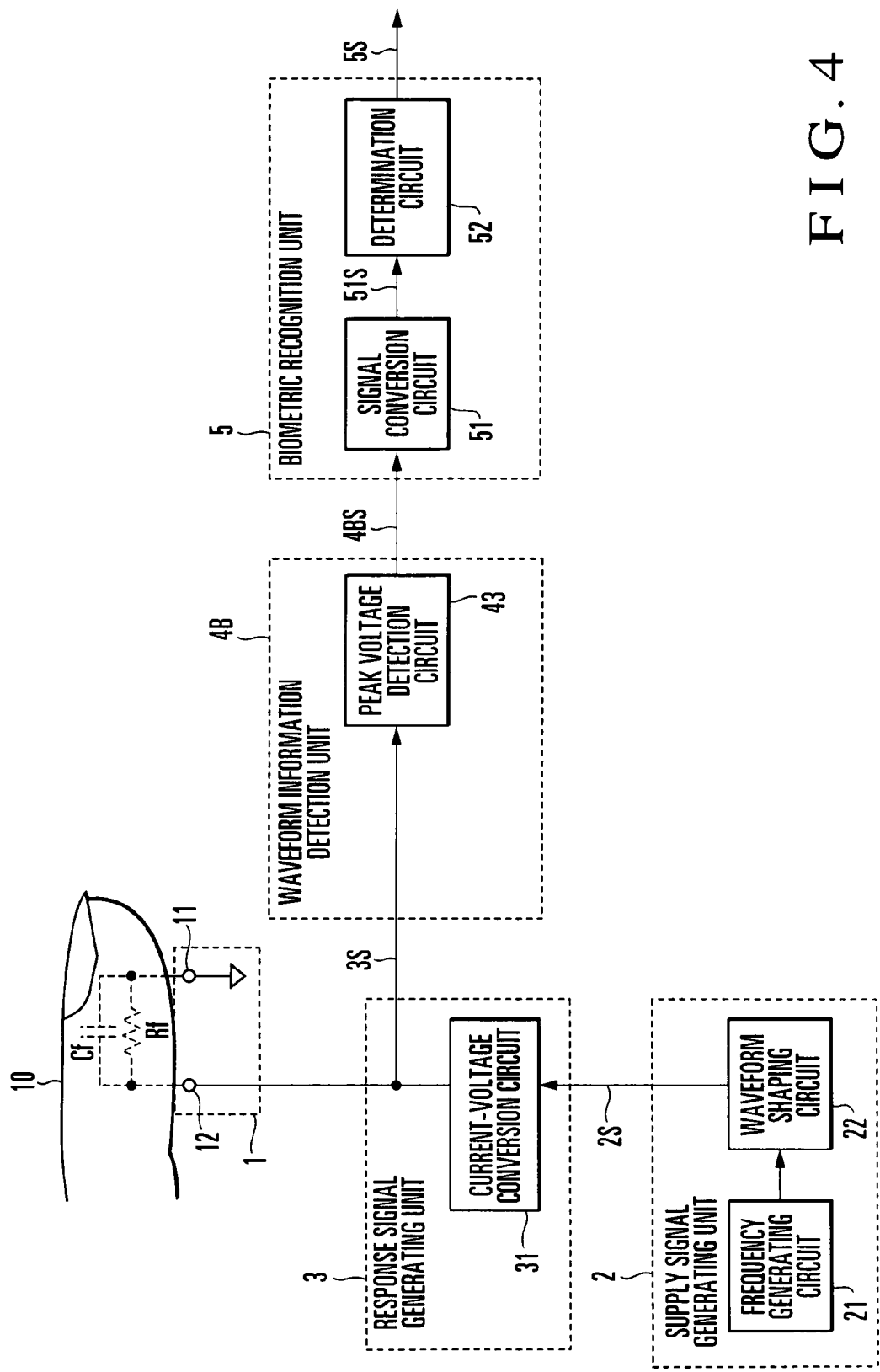
FIG. 4 is a block diagram showing the arrangement of a biometric recognition apparatus according to the third embodiment of the present invention.

A biometric recognition apparatus according to the third embodiment of the present invention will be described next. FIG. 4 is a block diagram showing a biometric recognition apparatus according to the third embodiment of the present invention. The same reference numerals as in FIG. 2 denote the same or equivalent parts in FIG. 4.

The second embodiment described above has exemplified the case wherein the waveform information detection unit 4A detects the phase information representing the capacitive component of the impedance of the object 10, which is contained in the response signal 3S, as the waveform information representing the imaginary component of the intrinsic impedance of the object 10. The third embodiment will exemplify a case wherein a waveform information detection unit 4B detects the resistive component of the impedance of an object 10, which is contained in a response signal 3S, as waveform information representing the real component of the intrinsic impedance of the object 10.

Referring to FIG. 4, the waveform information detection unit 4B is provided with a peak voltage detection circuit 43. The peak voltage detection circuit 43 detects an amplitude change corresponding to the impedance characteristic unique to the object 10, the resistive component in this case, from the response signal 3S, and outputs it as a detection signal 4BS. Practical examples of the peak voltage detection circuit 43 include a sample/hold circuit and the like. The arrangement of the biometric recognition apparatus in FIG. 4 is the same as that shown in FIG. 2 except for the waveform information detection unit 4B, and a detailed description thereof will be omitted.

The operation of the biometric recognition apparatus in FIG. 4 will be described next. The object 10 is connected to the output stage of a current-voltage conversion circuit 31 through detection electrodes 11 and 12 of a detection element 1. In this case, the intrinsic impedance of the object 10 can be represented by a capacitive component Cf and resistive component Rf connected between the detection electrodes 11 and 12 of the detection element 1. A supply signal 2S applied from the current-voltage conversion circuit 31 with a predetermined output impedance is voltage-divided by the output impedance of the current-voltage conversion circuit 31 and the intrinsic impedance of the object 10. The current flowing in the object 10 then changes in phase or amplitude in accordance with the intrinsic impedance of the object 10. Such a change is converted into a voltage and output as the response signal 3S.

In this embodiment, the peak voltage detection circuit 43 of the waveform information detection unit 4B outputs the detection signal 4BS containing the amplitude peak value of the response signal 3S.

Figure 5A:
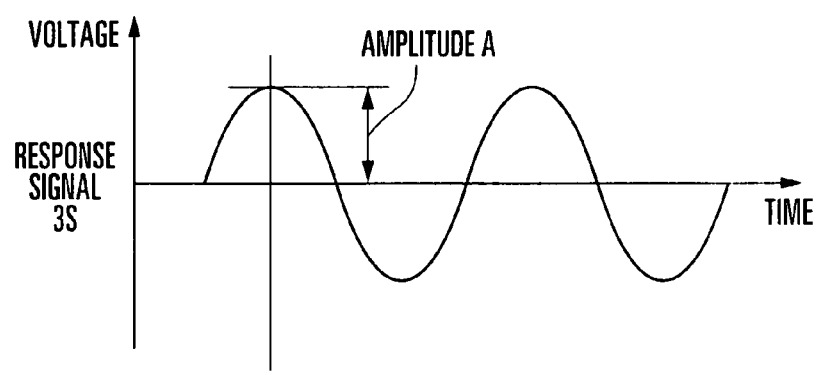
FIGS. 5A and 5B are signal waveform charts showing signals at the respective components of the biometric recognition apparatus in FIG. 4.
Figure 5B:
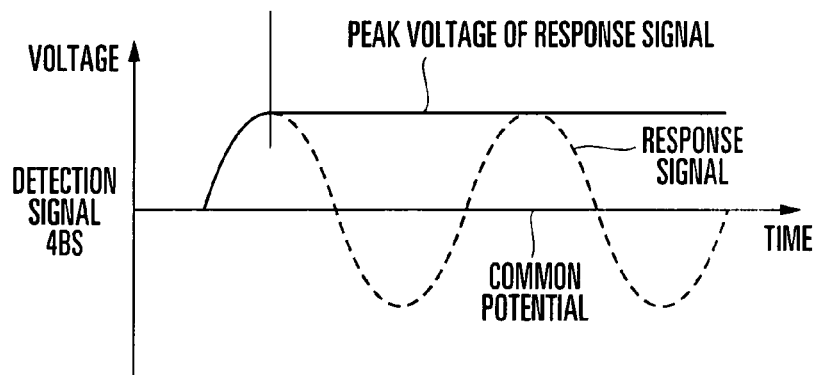

FIGS. 5A and 5B show signal waveform examples at the respective components in FIG. 4. When a sine wave centered on a common potential such as ground potential is used as a supply signal 2S, the response signal 3S changes in amplitude around the common potential in accordance with the impedance of the object 10. The peak voltage detection circuit 43 detects the peak voltage of the response signal 3S, i.e., the maximum or minimum value of the voltage, and outputs the detection signal 4BS representing a DC potential proportional to an amplitude A of the response signal 3S.

As described above, the waveform information detection unit 4B is provided with the peak voltage detection circuit 43 to detect an amplitude which changes in accordance with the intrinsic resistive component of the object 10 as waveform information representing the waveform of the response signal 3S. This makes it possible to minutely detect an electrical characteristic of an object, information representing the real component of the intrinsic impedance of the object 10 in this case, by using a peak voltage detection circuit such as a general sample/hold circuit, which is a very simple circuit arrangement as compared with the prior art, without requiring a resistive element or capacitive element which requires a large area. This in turn can easily realize a reduction in the size of the biometric recognition apparatus and the formation of a chip.

Fourth Embodiment

Figure 6:
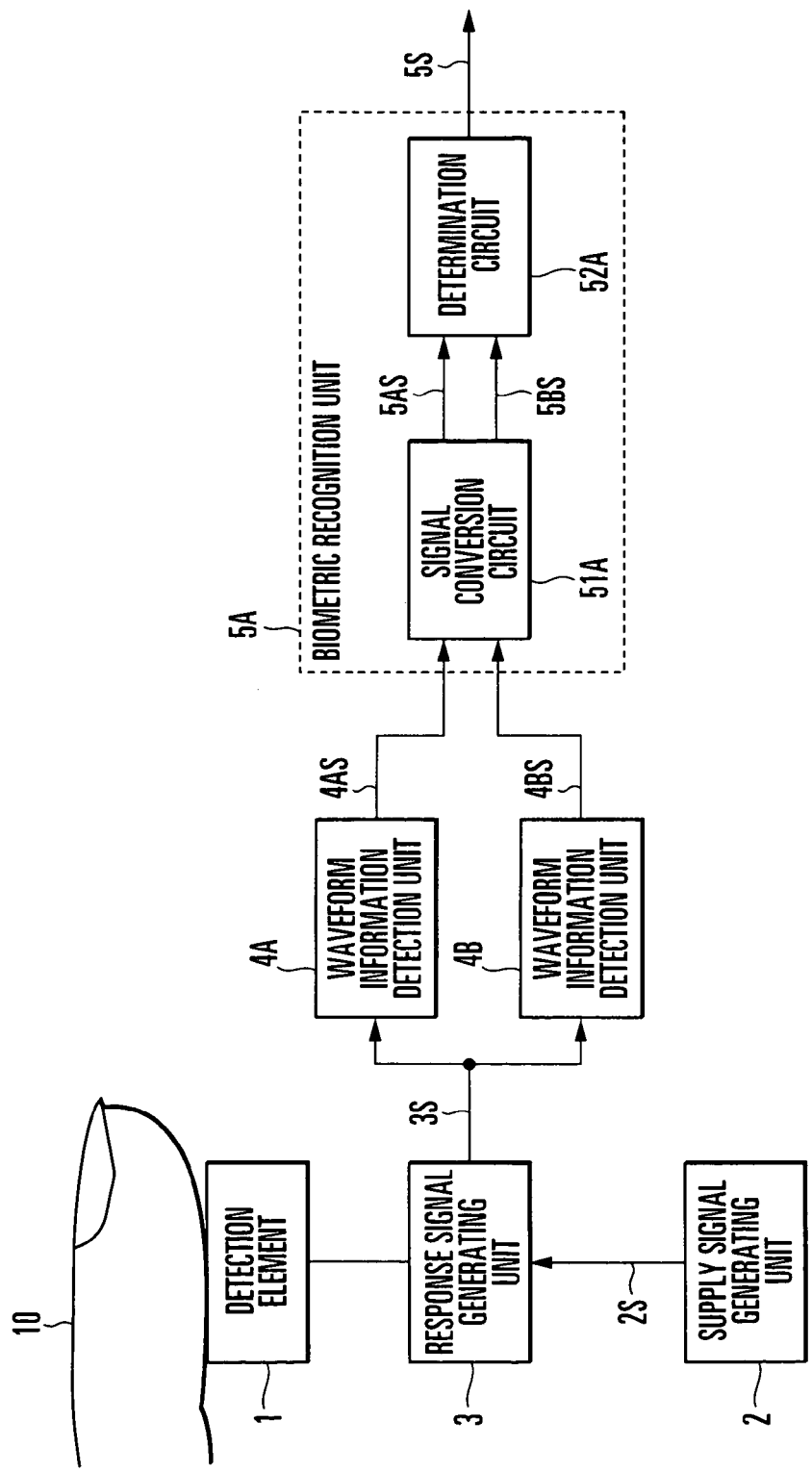
FIG. 6 is a block diagram showing the arrangement of a biometric recognition apparatus according to the fourth embodiment of the present invention.

A biometric recognition apparatus according to the fourth embodiment of the present invention will be described next with reference to FIG. 6. FIG. 6 is a block diagram showing the biometric recognition apparatus according to the fourth embodiment of the present invention. The same reference numerals as in FIG. 1 denote the same or equivalent parts in FIG. 6.

The first embodiment described above has exemplified the case wherein the waveform information detection unit 4 is provided to detect waveform information representing phase or amplitude information from the response signal 3S. The fourth embodiment will exemplify a case wherein two waveform information detection units 4A and 4B are provided to concurrently detect waveform information representing phase information and amplitude information from a response signal 3S, thereby performing biometric recognition.

The waveform information detection unit 4A is equivalent to the waveform information detection unit 4A in FIG. 2 described above, and is designed such that a phase comparison circuit 42 compares a reference signal 42S output from a reference signal generating circuit 42 with the response signal 3S to output a detection signal 4AS containing phase information of the response signal 3S. The waveform information detection unit 4B is equivalent to the waveform information detection unit 4B in FIG. 4 described above, and is designed such that a peak voltage detection circuit 43 detects the amplitude peak value of the response signal 3S to output a detection signal 4BS containing the peak value.

A signal conversion circuit 51A of a biometric recognition unit 5A converts the detection signals 4AS and 4BS from the waveform information detection units 4A and 4B into converted signals 5AS and 5BS, and output them to a determination circuit 52A. The determination circuit 52A determines whether or not the converted signals 5AS and 5BS from the signal conversion circuit 51A fall within a phase different reference range and amplitude reference range which represent the impedance characteristics of the authentic living body, thereby recognizing/determining whether or not an object 10 is a living body, and outputting a recognition result 5S with respect to the object 10.

As described, in this embodiment, the waveform information detection units 4A and 4B are provided to detect waveform information representing the phase difference and amplitude of the response signal 3S, and the biometric recognition unit 5A determines on the basis of the detected information whether or not the object 10 is a living body. This makes it possible to minutely detect an electrical characteristic of an object, information representing the real and imaginary components of the intrinsic impedance of the object 10 in this case, by using a phase comparison circuit such as a general comparator or logic circuit, which is a very simple circuit arrangement as compared with the prior art, without requiring a resistive element or capacitive element which requires a large area. This in turn can easily realize a reduction in the size of the biometric recognition apparatus and the formation of a chip.

In addition, performing biometric recognition/determination on the basis of information representing both the real and imaginary components of the impedance of an object makes it very difficult to separately adjust the real component and imaginary component of an object by selecting a material and quality for the object as compared with the case wherein biometric recognition/determination is performed by using information obtained by detecting real and imaginary components as a whole. This can obtain high security against fraudulent recognition activities using an artificial finger and the like. According to the above arrangement which separately detects real and imaginary components, as shown in FIG. 6, the waveform information detection unit 4A detects an imaginary component on the basis of waveform information representing the phase difference of the response signal 3S, and the waveform information detection unit 4B detects a real component on the basis of waveform information representing the amplitude of the response signal 3S. However, similar functions and effects can be obtained even if another arrangement is used as an arrangement which separately detects real and imaginary components.

In each of the first to fourth embodiments described above, consider a practical example of the biometric recognition unit 5 or 5A. When, for example, the detection signal 4AS having a pulse width corresponding to phase information is used, the signal conversion circuit 51 or 51A may convert the pulse width of this signal, and the comparator of the signal conversion circuit 51 or 51A may compare the voltage with a phase different reference range defined by voltages. When a phase difference reference range defined by time lengths is to be used, the gate circuit of the determination circuit 52 or 52A may directly compare the detection signal 4AS with a reference pulse representing the phase different reference range. This makes it possible to omit the signal conversion circuit 51 or 51A.

When the detection signal 4BS having a potential corresponding to amplitude information is to be used, the voltage comparator of the signal conversion circuit 51 or 51A may compare the signal with an amplitude difference reference range defined by voltages. This makes it possible to omit the signal conversion circuit 51 or 51A. When an amplitude reference range defined by time lengths is to be used, the signal conversion circuit 51 or 51A may convert the voltage into a pulse width, and the gate circuit of the determination circuit 52 or 52A may compare it with a reference pulse representing this amplitude reference range.

According to the above description, the biometric recognition unit 5 or 5A is comprised of an analog circuit. However, this unit may be comprised of a digital circuit. For example, the detection signal 4AS or 4BS is A/D-converted by the signal conversion circuit 51 or 51A, and the obtained digital value may be compared with digital information representing a phase different reference range or amplitude reference range by using the determination circuit 52 or 52A.

In this manner, the intrinsic impedance of an object is detected as waveform information representing the waveform of a response signal, and it is determined on the basis of the waveform information whether or not the object is a living body. This makes it possible to form the biometric recognition unit 5 or 5A by using a very simple circuit like that described above and to easily realize a reduction in the size of the biometric recognition apparatus and the formation of a chip.

Note that the magnitude of the imaginary or real component of an object may be computed from such a phase difference or amplitude, and the computed magnitude may be compared with the reference range of the imaginary or real components of the authentic living body.

Fifth Embodiment

Figure 7:
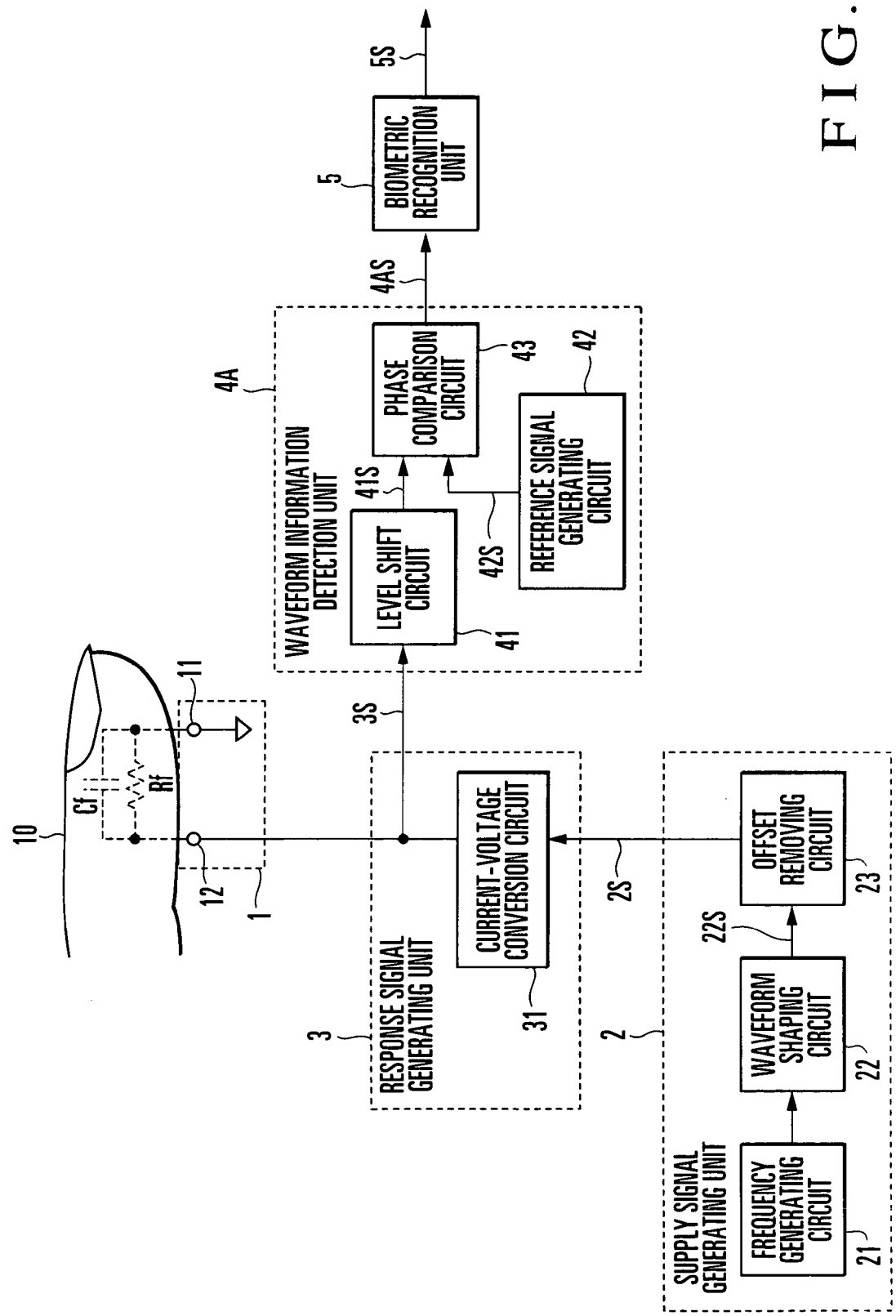
FIG. 7 is a block diagram showing the arrangement of a biometric recognition apparatus according to the fifth embodiment of the present invention.

A biometric recognition apparatus according to the fifth embodiment of the present invention will be described next with reference to FIG. 7. FIG. 7 is a block diagram showing the arrangement of the biometric recognition apparatus according to the fifth embodiment. FIG. 7 shows the details of examples of the arrangements of the supply signal generating unit 2, response signal generating unit 3, and waveform information detection unit 4 in the biometric recognition apparatus in FIG. 1.

This biometric recognition apparatus is designed such that a waveform information detection unit 4A detects the phase difference between a response signal 3S and a reference signal 42S synchronized with an original supply signal 2S as the above waveform information, and outputs a detection signal 4AS containing the waveform information. Note that the same reference numerals as in the first embodiment (see FIG. 1) denote the same or equivalent parts in the fifth embodiment.

Referring to FIG. 7, a detection element 1 is provided with detection electrodes 11 and 12 to electrically contact an object 10. A supply signal generating unit 2 is provided with a frequency generating circuit 21, waveform shaping circuit 22, and offset removing circuit 23. A response signal generating unit 3 is provided with a current-voltage conversion circuit 31. The waveform information detection unit 4A is provided with a level shift circuit 41, reference signal generating circuit 42, and phase comparison circuit 43.

In the detection element 1, the detection electrode 11 is connected to a common potential such as ground potential, and the detection electrode 12 is connected to the output stage of the current-voltage conversion circuit 31 of the response signal generating unit 3. This common potential is supplied from a predetermined supply circuit unit (not shown) such as a power supply circuit with a constant potential (low impedance).

In the supply signal generating unit 2, the frequency generating circuit 21 generates a clock signal having a predetermined frequency, and the waveform shaping circuit 22 generates an AC shaping signal 22S formed from a repetitive waveform such as a sine wave or triangular wave on the basis of the clock signal from the frequency generating circuit 21 and outputs it to the offset removing circuit 23. The offset removing circuit 23 removes a DC potential difference between the common potential and the central potential of the shaping signal 22S, i.e., an offset, from the shaping signal 22S to generate the supply signal 2S whose central potential coincides with the common potential, and outputs it. Note that the supply signal 2S may be supplied from an external waveform generating device instead of the supply signal generating unit 2.

The current-voltage conversion circuit 31 of the response signal generating unit 3 applies the supply signal 2S to the object 10 with a predetermined output impedance sufficiently lower than the impedance of the living body. In this case, the current-voltage conversion circuit 31 converts the current flowing in the object 10 through the detection element 1 into a voltage and outputs it as the response signal 3S.

In order to make the central potential of the response signal 3S, which coincides with the common potential, coincide with a predetermined reference potential, the level shift circuit 41 of the waveform information detection unit 4A level-shifts the overall DC bias of the signal, and outputs the resultant signal as a to-be-compared signal 41S to the phase comparison circuit 43. The reference signal generating circuit 42 outputs a reference signal 42S synchronized with the supply signal 2S to the phase comparison circuit 43. The phase comparison circuit 43 compares the phase of the to-be-compared signal 41S with that of the reference signal 42S to detect a phase difference corresponding to an intrinsic impedance characteristic of the object 10, a capacitive component in this case, as waveform information, and outputs the detection signal 4AS containing the waveform information. In this case, the supply signal 2S may be used as the reference signal 42S.

The biometric recognition unit 5 determines whether or not the phase difference represented by the detection signal 4AS from the phase comparison circuit 43 falls within a phase difference reference range representing an impedance characteristic of the authentic living body, thereby recognizing/determining whether or not the object 10 is a living body. The biometric recognition unit 5 then outputs a recognition result 5S with respect to the object 10.

The operation of the biometric recognition apparatus according to this embodiment will be described next. The object 10 is connected to the output stage of the current-voltage conversion circuit 31 through the detection electrodes 11 and 12 of the detection element 1. The intrinsic impedance of the object 10 can be represented by a capacitive component Cf and resistive component Rf connected between the detection electrodes 11 and 12 of the detection element 1. Therefore, the supply signal 2S applied from the current-voltage conversion circuit 31 with a predetermined output impedance is voltage-divided by the output impedance of the current-voltage conversion circuit 31 and the intrinsic impedance of the object 10. The current flowing in the object 10 then changes in phase or amplitude in accordance with the intrinsic impedance of the object 10. Such a change is converted into a voltage and output as the response signal 3S.

In this embodiment, the phase comparison circuit 43 of the waveform information detection unit 4A compares the phase of the to-be-compared signal 41S with the reference signal 42S output from the reference signal generating circuit 42, and outputs the detection signal 4AS containing the phase information (phase difference) of the response signal 3S.

In this case, if there is an offset between a common potential such as ground potential connected to the detection electrode 11 of the detection element 1 and the supply signal 2S applied to the detection electrode 12, since a DC current flows in the object 10, an offset corresponding to the resistive component Rf of the object 10 also occurs in the response signal 3S. In this embodiment, the offset removing circuit 23 is provided for the supply signal generating unit 2 to remove the offset between the supply signal 2S and the common potential to suppress the application of a DC current to the object 10 and prevent the occurrence of an offset in the response signal 3S.

In addition, the level shift circuit 41 is provided for the waveform information detection unit 4A to level-shift the response signal 3S so as to generate the to-be-compared signal 41S whose central potential coincides with a reference potential. A phase difference is detected by using the to-be-compared signal 41S.

FIGS. 8A to 8F show signal waveform examples at the respective components in FIG. 7. The waveform shaping circuit 22 of the supply signal generating unit 2 generates the shaping signal 22S whose central potential coincides with a potential VA almost intermediate between an operating power supply potential VDD of the circuit and ground potential (0 V=GND). In this case, when ground potential is used as a common potential, an offset corresponding to the central potential VA is present in the shaping signal 22S. The offset removing circuit 23 removes this offset to generate and output the supply signal 2S whose central potential coincides with the common potential. As a consequence, no DC current is applied to the object 10, and a signal whose central potential coincides with a common potential can be obtained as the response signal 3S without any offset caused by the resistive component Rf of the object 10.

In this embodiment, in order to operate each signal processing circuit by using a single operating power supply, i.e., an operation power supply only in the positive direction (negative direction) with respect to ground potential, the level shift circuit 41 of the waveform information detection unit 4A level-shifts the response signal 3S to make the amplitude of the response signal 3S fall between ground potential and the operating power supply potential VDD, and outputs the resultant signal as the to-be-compared signal 41S.

In comparing the to-be-compared signal 41S with the reference signal 42S, the phase comparison circuit 43 temporarily converts these analog signals into digital signals to make the logic circuit perform phase comparison. In converting analog signals into digital signals, a method of amplifying the analog signals with high gains or comparing them with a predetermined threshold.

In this case, if the central potential of an analog signal does not coincide with a desired reference potential, an error occurs in the phase obtained from the digital signal. When, for example, an analog signal is amplified with a high gain, since the analog signal is digitized by making it saturate to either the operating power supply potential VDD or ground potential with a reference voltage serving as a threshold. If, therefore, the central potential of the analog signal deviates from the reference potential, the length of an interval of the analog signal in which the potential is higher than the reference potential becomes asymmetrical with the length of an interval of the signal in which the potential is lower than the reference potential. Even if the response signal 3S is a sine wave, therefore, the duty ratio of the obtained digital signal does not become 1:1, and an error occurs in a phase (the timing of a leading or trailing edge). This applies the same to a case wherein an analog signal is digitized by being compared with a predetermined threshold, i.e., a reference potential.

When, therefore, the response signal 3S is to be level-shifted by the level shift circuit 41 of the waveform information detection unit 4A, the response signal 3S is level-shifted such that the central potential coincides with the reference signal. This can realize a single operating power supply and suppress the occurrence of the above phase error.

The reference signal 42S from the reference signal generating circuit 42 is digitized by the phase comparison circuit 43 in the same manner as described above. In this case, making the central potential of the reference signal 42S generated by the reference signal generating circuit 42 coincide with the reference potential at the time of level shifting makes it possible to easily obtain a digital signal with very little phase shift and accurately detect a phase difference.

When a sine wave centered on a common potential such as ground potential is used as the supply signal 2S, the phase of the response signal 3S changes in accordance with the impedance of the object 10. By using a signal synchronized with the supply signal 2S as the reference signal 42S and making the phase comparison circuit 43 compare the phase of the signal with that of the response signal 3S, i.e., the to-be-compared signal 41S, the detection signal 4AS is output, which has a phase difference $\phi$ corresponding to the capacitive component of the impedance of the object 10 as a pulse width.

Since the phase comparison circuit 43 is provided for the waveform information detection unit 4A to compare the phase of the response signal 3S with that of the reference signal 42S in this manner, a phase which changes in accordance with the intrinsic capacitive component of the object 10 can be detected as waveform information representing the waveform of the response signal 3S. This makes it possible to minutely detect an electrical characteristic of an object, information representing the imaginary component of the intrinsic impedance of the object 10 in this case, by using a phase comparison circuit such as a general comparator or logic circuit, which is a very simple circuit arrangement as compared with the prior art, without requiring a resistive element or capacitive element which requires a large area. This in turn can easily realize a reduction in the size of the biometric recognition apparatus and the formation of a chip.

In addition, the offset removing circuit 23 generates the supply signal 2S whose central potential coincides with a common potential and applies it to the object 10. The level shift circuit 41 then level-shifts the response signal 3S to make the central potential coincide with the reference potential to generate the to-be-compared signal 41S. Phase comparison is performed on the basis of the to-be-compared signal 41S. This makes it possible to separately set an operating power supply potential for a signal processing circuit and a common potential with a relatively simple circuit arrangement. Therefore, for example, using ground potential as a common potential can improve noise resistance and allows the use of a single power supply as an operating power supply for the signal processing circuit. This makes it possible to reduce the layout area of the circuit as compared with a case wherein positive and negative power supplies are used. This in turn can reduce the manufacturing cost of the biometric recognition apparatus.

Sixth Embodiment

Figure 9:
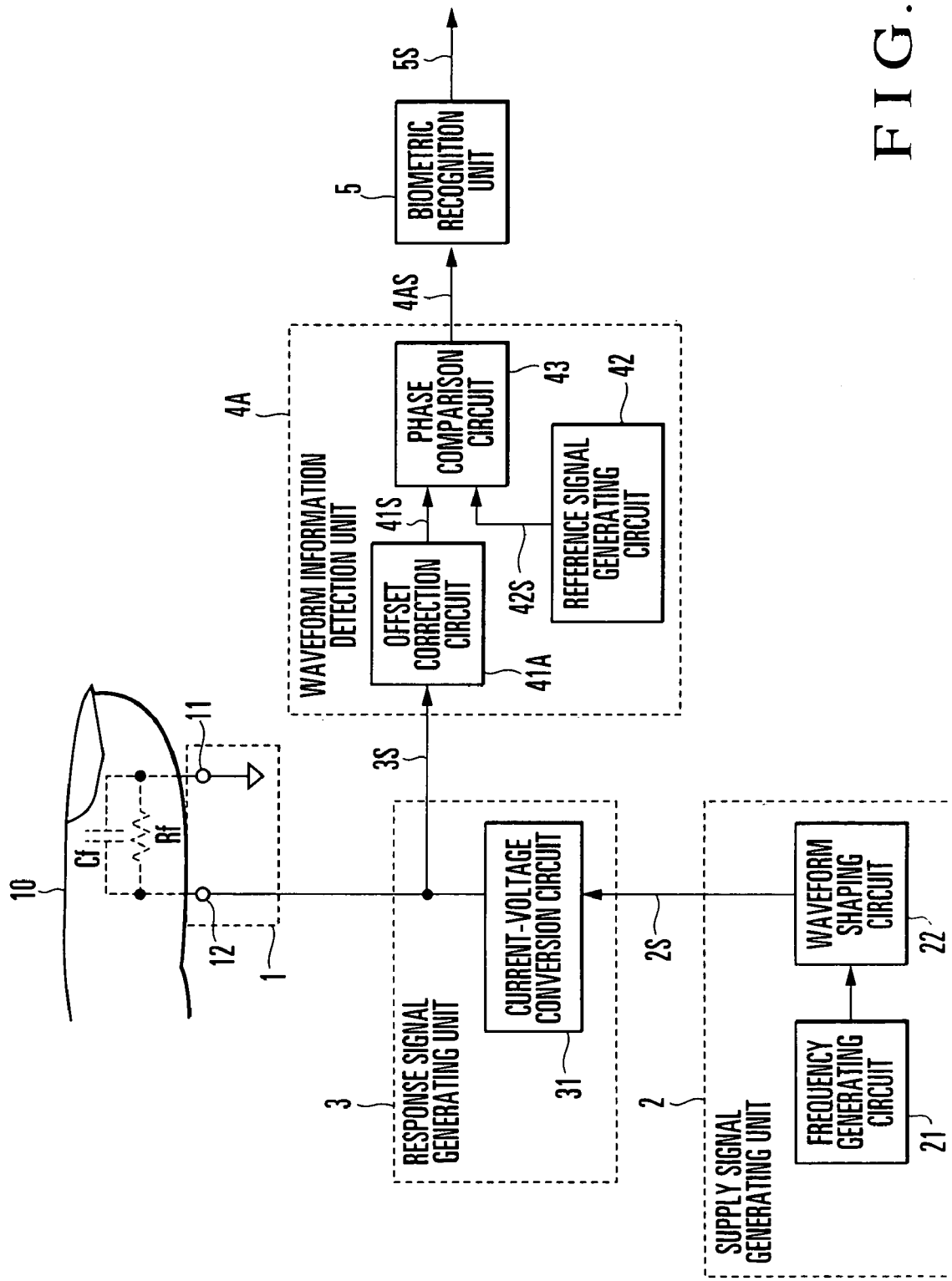
FIG. 9 is a block diagram showing the arrangement of a biometric recognition apparatus according to the sixth embodiment of the present invention.

A biometric recognition apparatus according to the sixth embodiment of the present invention will be described next with reference to FIG. 9. FIG. 9 is a block diagram showing the biometric recognition apparatus according to the sixth embodiment of the present invention.

In this embodiment, the phase of a response signal 3S is detected as waveform information as in the fifth embodiment described above (see FIG. 7). The sixth embodiment, however, differs from the fifth embodiment in that a signal containing an offset with respect to a common potential is applied as a supply signal 2S to a detection element 1 to make a waveform information detection unit 4A correct an offset caused in the response signal 3S. Note that the same reference numerals as in FIG. 7 denote the same or equivalent parts in FIG. 9.

A supply signal generating unit 2 is comprised of a frequency generating circuit 21 and waveform shaping circuit 22, but is not provided with the above offset removing circuit 23.

The waveform information detection unit 4A is provided with an offset correction circuit 41A instead of the above level shift circuit 41. The offset correction circuit 41A corrects an offset caused in the response signal 3S, i.e., the DC potential difference between the central potential of the response signal 3S and a reference potential, in accordance with a resistive component Rf of an object 10.

The operation of the biometric recognition apparatus according to this embodiment will be described next with reference to FIGS. 10A to 10E. FIGS. 10A to 10E show signal waveform examples at the respective components of the biometric recognition apparatus in FIG. 9.

The waveform shaping circuit 22 of the supply signal generating unit 2 generates and outputs the supply signal 2S whose central potential coincides with a potential VA almost intermediate between an operating power supply potential VDD of the circuit and ground potential (0 V=GND). As a consequence, a DC current is applied to the object 10, and the response signal 3S becomes a signal containing the offset caused by the resistive component Rf of the object 10. Assume that when Rf is a predetermined value, the central potential of the response signal 3S becomes a reference potential VB. In this case, if Rf is larger than the predetermined value, VB2 higher than the reference potential VB becomes the central potential. If Rf is smaller than the predetermined value, VB1 lower than the reference potential VB becomes the central potential.

In this embodiment, the offset correction circuit 41A of the waveform information detection unit 4A level-shifts the response signal 3S to make the amplitude of the response signal 3S fall between ground potential and the operating power supply potential VDD, and outputs the resultant signal as a to-be-compared signal 41S, thereby allowing the subsequent circuit to operate on a single operating power supply, i.e., an operating power supply only in the positive direction (negative direction) with respect to ground potential.

In this case, causing the offset correction circuit 41A to level-shift the response signal 3S so as to make the central potential coincide with the reference potential VB used for phase comparison makes it possible not only to realize a single operating power supply, but also to suppress the occurrence of a phase error in the above digitizing operation.

In this manner, the waveform information detection unit 4A is provided with a phase comparison circuit 43 to compare the phase of the response signal 3S with the reference signal 42S, thereby detecting a phase which changes in accordance with the intrinsic capacitive component of the object 10 as waveform information representing the waveform of the response signal 3S. This makes it possible to minutely detect an electrical characteristic of an object, information representing the imaginary component of the intrinsic impedance of the object 10 in this case, by using a phase comparison circuit such as a general comparator or logic circuit, which is a very simple circuit arrangement as compared with the prior art, without requiring a resistive element or capacitive element which requires a large area. This in turn can easily realize a reduction in the size of the biometric recognition apparatus and the formation of a chip.

In addition, the offset correction circuit 41A generates the to-be-compared signal 41S by correcting the offset of the response signal 3S so as to make the central potential become the reference potential. Phase comparison is then performed on the basis of the to-be-compared signal 41S. This makes it possible to separately set an operating power supply potential for a signal processing circuit and a common potential with a relatively simple circuit arrangement. Therefore, for example, using ground potential as a common potential can improve noise resistance and allows the use of a single power supply as an operating power supply for the signal processing circuit. This makes it possible to reduce the layout area of the circuit as compared with a case wherein positive and negative power supplies are used. This in turn can reduce the manufacturing cost of the biometric recognition apparatus.

Seventh Embodiment

Figure 11:
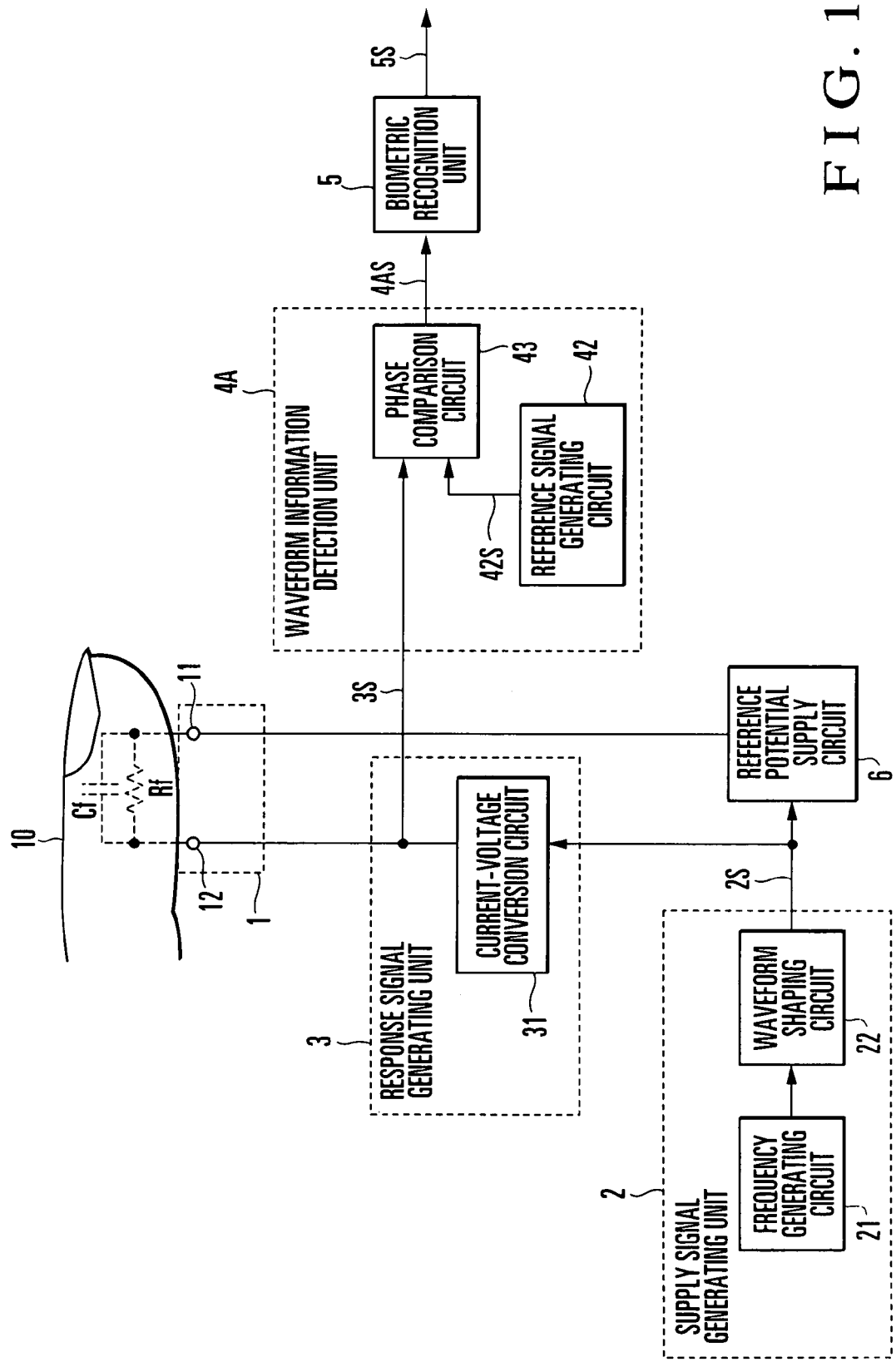
FIG. 11 is a block diagram showing the arrangement of a biometric recognition apparatus according to the seventh embodiment of the present invention.
Figure 12A:
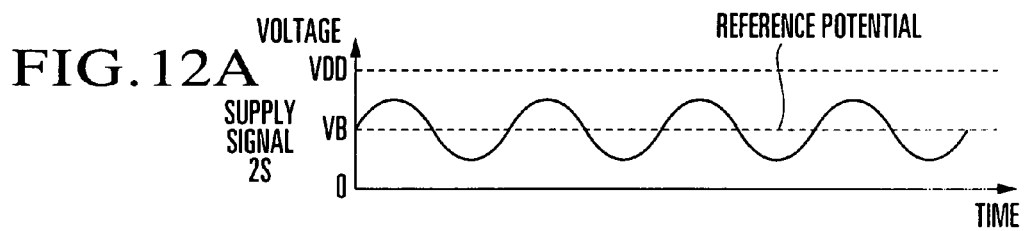
FIGS. 12A to 12D are signal waveform charts showing signals at the respective components of the biometric recognition apparatus in FIG. 11.
Figure 12B:
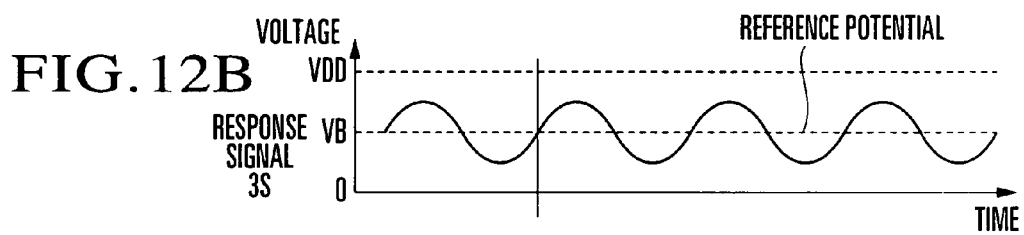
Figure 12C:
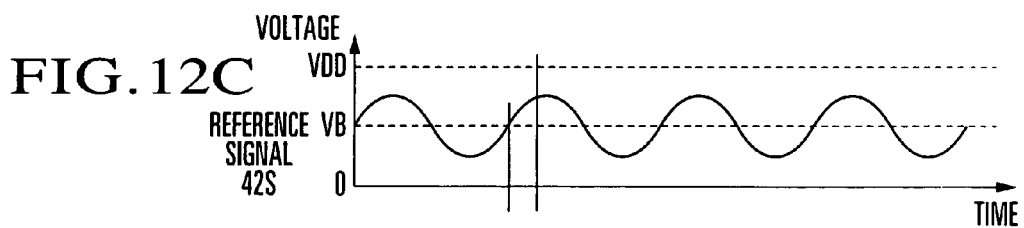
Figure 12D:
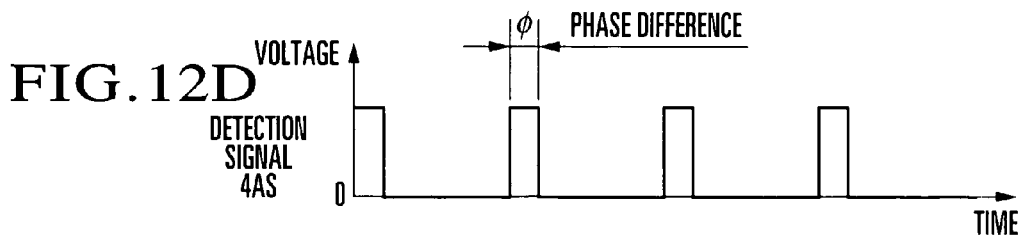

A biometric recognition apparatus according to the seventh embodiment of the present invention will be described next with reference to FIG. 11. FIG. 11 is a block diagram showing the biometric recognition apparatus according to the seventh embodiment of the present invention.

In this embodiment, the phase of a response signal 3S is detected as waveform information as in the sixth embodiment described above (see FIG. 9). The seventh embodiment however differs from the sixth embodiment in that a reference potential supply unit 6 is provided to supply a common potential equal to the central potential of a supply signal 2S to a detection element 1. The same reference numerals as in FIG. 9 denote the same or equivalent parts in FIG. 11.

The reference potential supply unit 6 is a circuit which detects the central potential of the supply signal 2S generated by a supply signal generating unit 2, generates a reference potential VB equal to the central potential, and supplies the reference potential to a detection electrode 11 of the detection element 1 with a low impedance. In this case, as the supply signal 2S, an intermediate potential between an operating power supply potential VDD for each signal circuit and ground potential is used, and the reference potential also becomes equal to the intermediate potential.

Note that a waveform information detection unit 4A is comprised of a reference signal generating circuit 42 and phase comparison circuit 43, but is not provided with the above offset correction circuit 41A.

The operation of the biometric recognition apparatus according to this embodiment will be described next with reference to FIGS. 12A to 12D. FIGS. 12A to 12D show signal waveform examples at the respective components of the biometric recognition apparatus in FIG. 11.

A waveform shaping circuit 22 of the supply signal generating unit 2 generates and outputs the supply signal 2S whose central potential coincides with an intermediate potential between the operating power supply potential VDD for the circuit and ground potential. The reference potential supply unit 6 detects the central potential of the supply signal 2S and supplies the reference potential VB equal to the detected potential to the detection electrode 11. With this operation, no DC current is applied to an object 10, and the response signal 3S becomes a signal whose central potential coincides with the reference potential VB.

In this case, the reference potential VB is used as a reference potential used for the phase comparison circuit 43, and the response signal 3S is directly input to the phase comparison circuit 43, in which the phase of the response signal 3S is compared with that of a reference signal 42S.

In this manner, the waveform information detection unit 4A is provided with the phase comparison circuit 43 to compare the phase of the response signal 3S with the reference signal 42S, thereby detecting a phase which changes in accordance with the intrinsic capacitive component of the object 10 as waveform information representing the waveform of the response signal 3S. This makes it possible to minutely detect an electrical characteristic of an object, information representing the imaginary component of the intrinsic impedance of the object 10 in this case, by using a phase comparison circuit such as a general comparator or logic circuit, which is a very simple circuit arrangement as compared with the prior art, without requiring a resistive element or capacitive element which requires a large area. This in turn can easily realize a reduction in the size of the biometric recognition apparatus and the formation of a chip.

In addition, since a reference potential equal to the central potential of the supply signal 2S is supplied as a common potential for the detection element 1 from the reference potential supply unit 6, a desired detection signal having waveform information corresponding to the impedance of an object can be obtained with a relatively simple circuit arrangement using a single power supply instead of positive and negative power supplies. This makes it possible to reduce the layout area of the circuit as compared with a case wherein positive and negative power supplies are used. This in turn can reduce the manufacturing cost of the biometric recognition apparatus.

Eighth Embodiment

Figure 13:
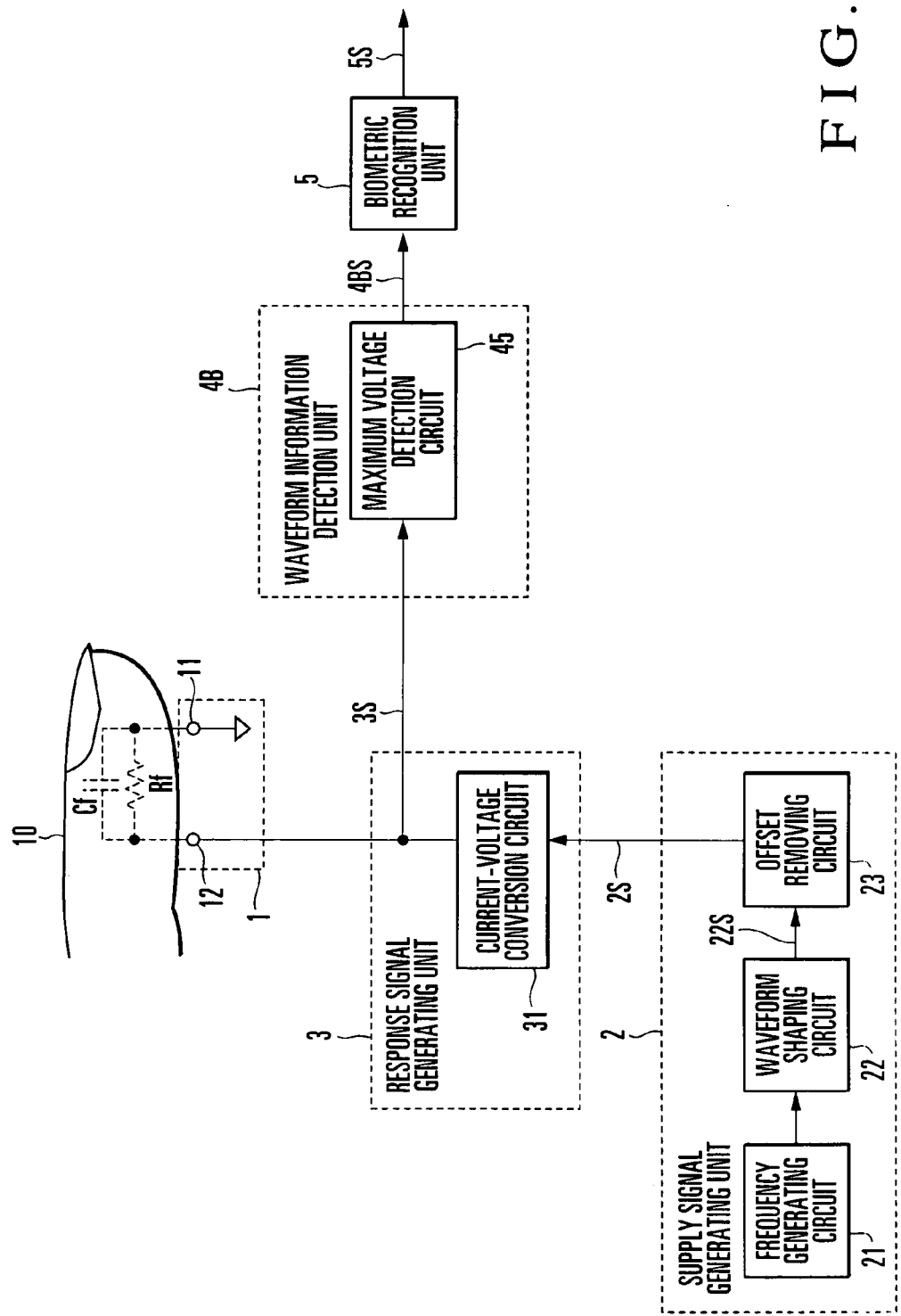
FIG. 13 is a block diagram showing the arrangement of a biometric recognition apparatus according to the eighth embodiment of the present invention.
Figure 14A:
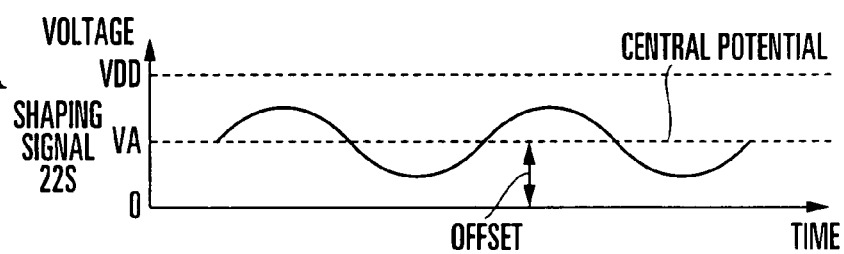
FIGS. 14A to 14D are signal waveform charts showing signals at the respective components of the biometric recognition apparatus in FIG. 13.
Figure 14B:
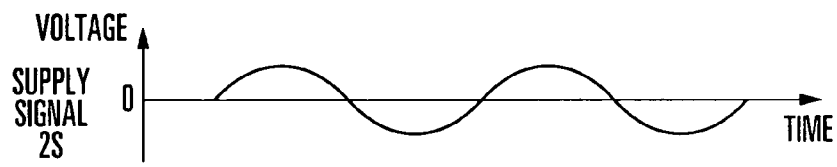
Figure 14C:
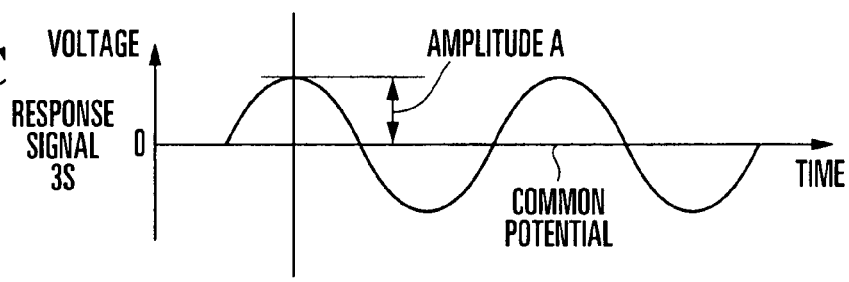
Figure 14D:
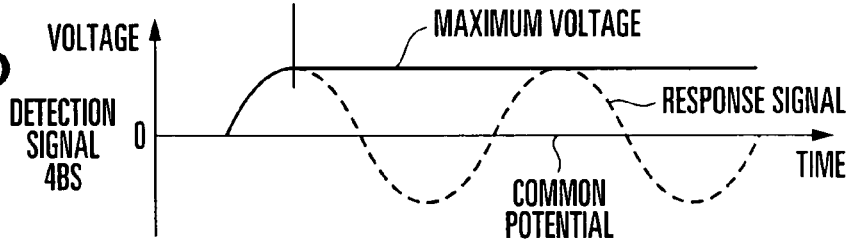

A biometric recognition apparatus according to the eighth embodiment of the present invention will be described next with reference to FIG. 13. FIG. 13 is a block diagram showing the biometric recognition apparatus according to the eighth embodiment of the present invention.

In this biometric recognition apparatus, a waveform information detection unit 4B detects the amplitude of a response signal 3S as the above waveform information, and outputs a detection signal 4BS containing the waveform information. This embodiment differs from the fifth embodiment (see FIG. 7) in that the waveform information detection unit 4B includes a maximum voltage detection circuit 45. Note that the same reference numerals as in FIG. 7 denote the same or equivalent parts in FIG. 13.

The maximum voltage detection circuit 45 detects an intrinsic impedance characteristic of an object 10, an amplitude change corresponding to a resistive component, from the response signal 3S whose central potential coincides with a common potential such as ground potential, and outputs the resultant information as the detection signal 4BS. Practical examples of the maximum voltage detection circuit 45 include a sample/hold circuit and the like. Note that the arrangement of the biometric recognition apparatus in FIG. 13 is the same as that shown in FIG. 7 except for the waveform information detection unit 4B, and a detailed description thereof will be omitted.

The operation of the biometric recognition apparatus in FIG. 13 will be described. The object 10 is connected to the output stage of a current-voltage conversion circuit 31 through detection electrodes 11 and 12 of a detection element 1. In this case, the intrinsic impedance of the object 10 can be represented by a capacitive component Cf and resistive component Rf connected between the detection electrodes 11 and 12 of the detection element 1. Therefore, a supply signal 2S applied from the current-voltage conversion circuit 31 with a predetermined output impedance is voltage-divided by the output impedance of the current-voltage conversion circuit 31 and the intrinsic impedance of the object 10. The current flowing in the object 10 then changes in phase or amplitude in accordance with the intrinsic impedance of the object 10. Such a change is converted into a voltage and output as the response signal 3S.

In this embodiment, the maximum voltage detection circuit 45 of the waveform information detection unit 4B outputs the detection signal 4BS containing the amplitude peak value of the response signal 3S.

FIGS. 14A to 14D show signal waveform examples at the respective components in FIG. 13. A waveform shaping circuit 22 of a supply signal generating unit 2 generates a shaping signal 22S whose central potential coincides with a potential VA almost intermediate between an operating power supply potential VDD for the circuit and ground potential (0 V=GND). An offset removing circuit 23 then outputs the supply signal 2S whose central potential coincides with the common potential.

With this operation, the response signal 3S becomes a signal whose central potential coincides with the common potential, and the amplitude changes in accordance with the impedance of the object 10. The maximum voltage detection circuit 45 detects the maximum voltage value of the response signal 3S, and outputs the detection signal 4BS representing a DC potential proportional to an amplitude A of the response signal 3S.

In this manner, the waveform information detection unit 4B is provided with maximum voltage detection circuit 45 to detect an amplitude which changes in accordance with the intrinsic resistive component of the object 10 as waveform information representing the waveform of the response signal 3S. This makes it possible to minutely detect an electrical characteristic of an object, information representing the real component of the intrinsic impedance of the object 10 in this case, by using a peak voltage detection circuit such as a general sample/hold circuit, which is a very simple circuit arrangement as compared with the prior art, without requiring a resistive element or capacitive element which requires a large area. This in turn can easily realize a reduction in the size of the biometric recognition apparatus and the formation of a chip.

In addition, since the supply signal 2S whose central potential coincides with the common potential is generated by the offset removing circuit 23 and applied to the object 10, when ground potential is used as the common potential, the amplitude of the response signal 3S corresponding to the object 10 can be obtained by only making the maximum voltage detection circuit 45 detect the maximum voltage of the response signal 3S. Therefore, for example, using ground potential as a common potential can improve noise resistance and allows the use of a single power supply as an operating power supply for the signal processing circuit. This makes it possible to reduce the layout area of the circuit as compared with a case wherein positive and negative power supplies are used. This in turn can reduce the manufacturing cost of the biometric recognition apparatus.

Ninth Embodiment

Figure 15:
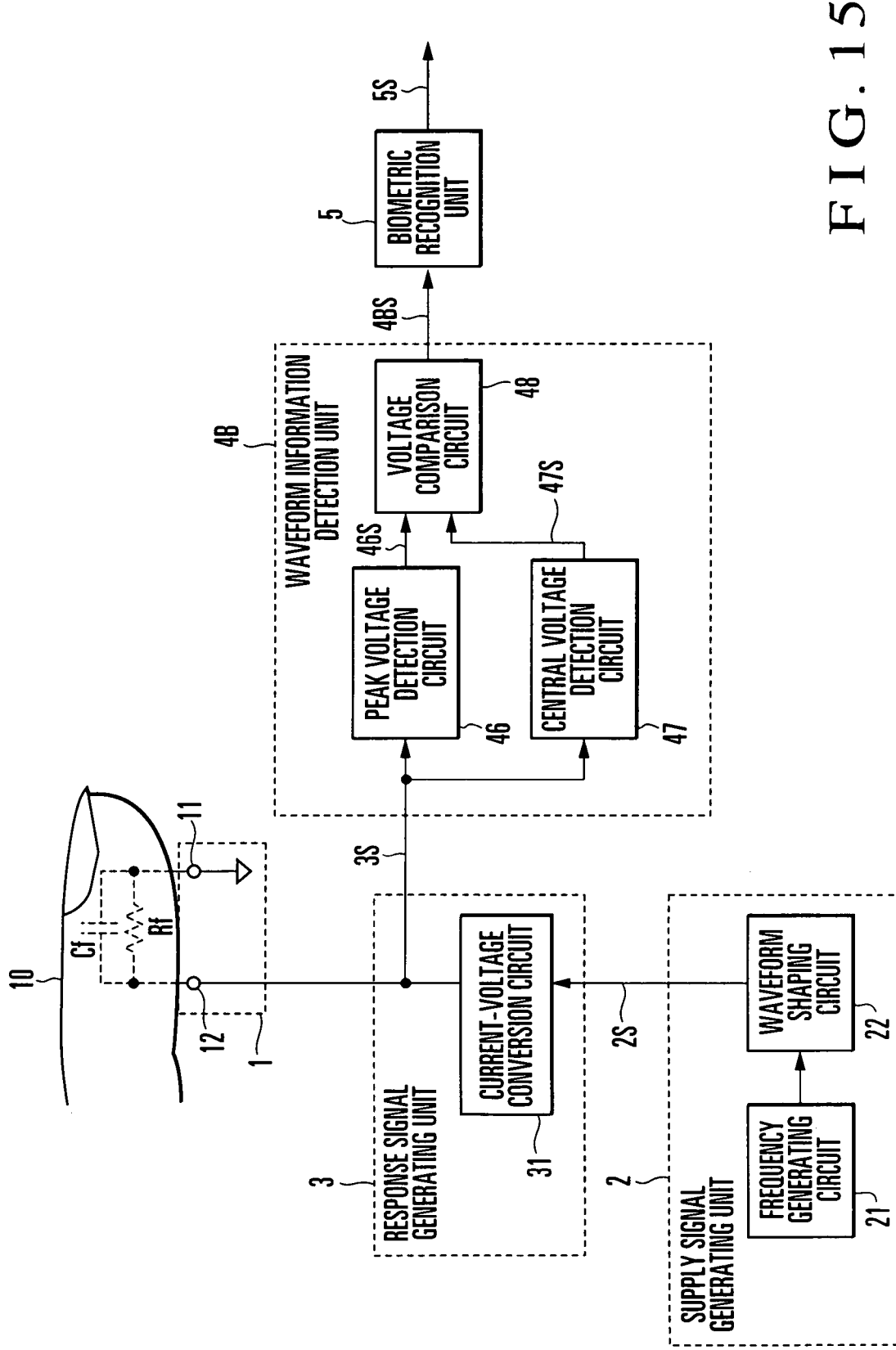
FIG. 15 is a block diagram showing the arrangement of a biometric recognition apparatus according to the ninth embodiment of the present invention.

A biometric recognition apparatus according to the ninth embodiment of the present invention will be described next with reference to FIG. 15. FIG. 15 is a block diagram showing the biometric recognition apparatus according to the ninth embodiment of the present invention.

In this embodiment, the amplitude of a response signal 3S as waveform information is detected as in the eighth embodiment described above (see FIG. 13). The ninth embodiment differs from the eighth embodiment in that a waveform information detection unit 4B detects the amplitude of the response signal 3S by comparing the peak voltage value of the response signal 3S with the central potential value. Note that the same reference numerals as in FIG. 7 denote the same or equivalent parts in FIG. 15.

The waveform information detection unit 4B is comprised of a peak voltage detection circuit 46, central voltage detection circuit 47, and voltage comparison circuit 48. The peak voltage detection circuit 46 detects a peak voltage value 46S of the response signal 3S. The central voltage detection circuit 47 detects a central voltage value 47S of the response signal 3S. The voltage comparison circuit 48 compares the peak voltage value 46S with the central voltage value 47S and detects the amplitude of the response signal 3S from the voltage difference between them. The voltage comparison circuit 48 then outputs a detection signal 4BS containing the detected amplitude as waveform information.

Note that a supply signal generating unit 2 is comprised of a frequency generating circuit 21 and waveform shaping circuit 22 but is not provided with the above offset removing circuit 23.

The operation of the biometric recognition apparatus according to this embodiment will be described next with reference to FIGS. 16A to 16C. FIGS. 16A to 16C show signal waveform examples at the respective components of the biometric recognition apparatus in FIG. 15.

A waveform shaping circuit 22 of the supply signal generating unit 2 outputs a supply signal 2S whose central potential coincides with a voltage VA almost intermediate between an operating power supply potential VDD for the circuit and ground potential (0 V=GND). As a consequence, a DC current is applied to the object 10, and the response signal 3S becomes a signal containing an offset caused by the resistive component Rf of the object 10.

In this embodiment, the waveform information detection unit 4B is provided with the peak voltage detection circuit 46 and central voltage detection circuit 47 to detect the peak voltage value 46S and central voltage value 47S of the response signal 3S, and the voltage comparison circuit 48 detects the amplitude of the response signal 3S by comparing them. In this case, the peak voltage value may be the maximum or minimum voltage value of the response signal 3S.

In this manner, the waveform information detection unit 4B detects an amplitude which changes in accordance with the intrinsic resistive component of the object 10 as waveform information representing the waveform of the response signal 3S. This makes it possible to minutely detect an electrical characteristic of an object, information representing the real component of the intrinsic impedance of the object 10 in this case, by using a peak voltage detection circuit such as a general sample/hold circuit, which is a very simple circuit arrangement as compared with the prior art, without requiring a resistive element or capacitive element which requires a large area. This in turn can easily realize a reduction in the size of the biometric recognition apparatus and the formation of a chip.

In addition, since the peak voltage detection circuit 46 and central voltage detection circuit 47 detect the peak voltage value 46S and central voltage value 47S of the response signal 3S, and the voltage comparison circuit 48 detects the amplitude of the response signal 3S by comparing them, the amplitude of the response signal 3S can be detected regardless of the central potential of the response signal 3S. Therefore, for example, using ground potential as a common potential can improve noise resistance and allows the use of a single power supply as an operating power supply for the signal processing circuit. This makes it possible to reduce the layout area of the circuit as compared with a case wherein positive and negative power supplies are used. This in turn can reduce the manufacturing cost of the biometric recognition apparatus.

In this embodiment, a maximum voltage detection circuit and minimum voltage detection circuit may be used in place of the peak voltage detection circuit 46 and central voltage detection circuit 47, and the voltage comparison circuit 48 may detect an amplitude B of the response signal 3S by using the maximum voltage value and minimum voltage value of the response signal 3S which are obtained from these circuits, as shown in FIGS. 17A and 17B. With this arrangement, the same functions and effects as those described above can be obtained.

Each of the fifth to ninth embodiments described above has exemplified the case wherein either a phase difference or an amplitude is detected by the waveform information detection unit 4 (4A, 4B). However, both a phase difference and an amplitude may be concurrently detected, and the biometric recognition unit 5 may determine on the basis of the respective detection signals whether the object 10 is a living body. This makes it very difficult to separately adjust the real component and imaginary component of an object by selecting a material and quality for the object, thereby obtaining high security against fraudulent recognition activities using an artificial finger and the like.

In this case, if one of the fifth to seventh embodiments is combined with the eight or ninth embodiment, for example, the noise resistance can be improved by using ground potential as a common potential. In addition, a single power supply can be used as an operating power supply for the signal processing circuit. This makes it possible to reduce the layout area of the circuit as compared with a case wherein positive and negative power supplies are used. This in turn can reduce the manufacturing cost of the biometric recognition apparatus.

In this case, in the eighth embodiment (see FIG. 13), the central potential of the response signal 3S preferably coincides with ground potential, and hence the eighth embodiment can be easily combined with the fifth embodiment (see FIG. 7) which uses ground potential as a common potential. In the ninth embodiment (see FIG. 15), the response signal 3S is preferably present between the operating power supply potential and ground potential, and hence the ninth embodiment can be easily combined with the sixth embodiment (see FIG. 9) or the seventh embodiment (see FIG. 11).

10th Embodiment

Figure 18:
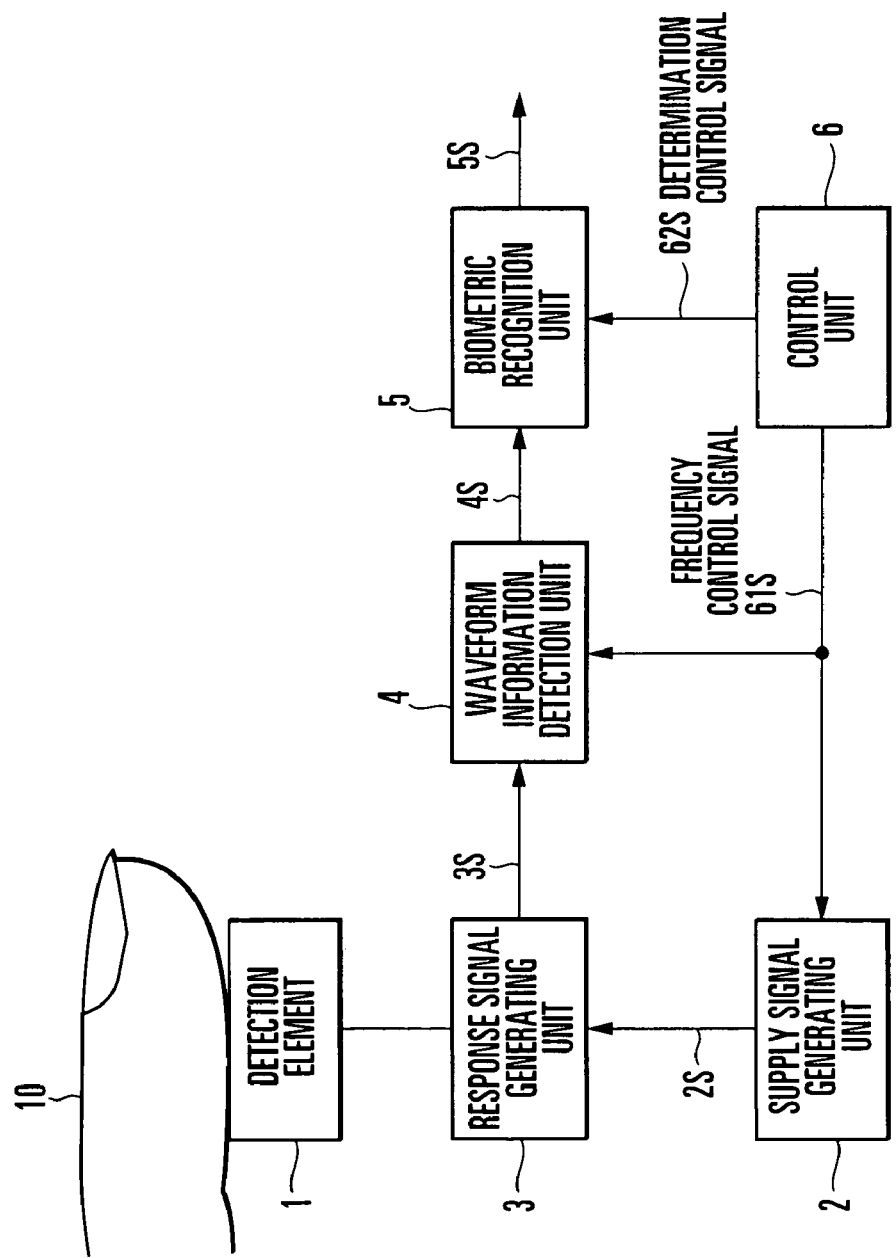
FIG. 18 is a block diagram showing the arrangement of a biometric recognition apparatus according to the 10th embodiment of the present invention.
Figure 21A:
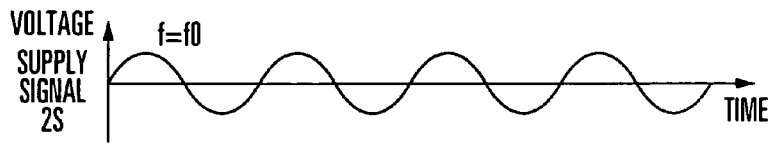
FIGS. 21A to 21D are signal waveform charts showing changes in phase difference with changes in frequency.
Figure 21B:
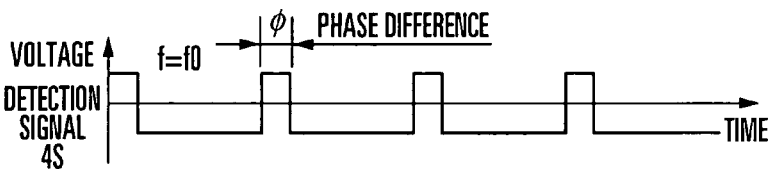
Figure 21C:
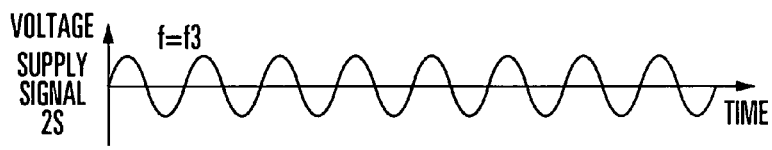
Figure 21D:
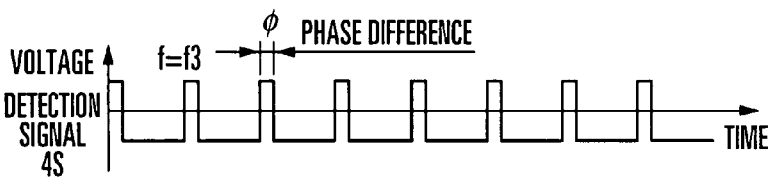
Figure 22A:
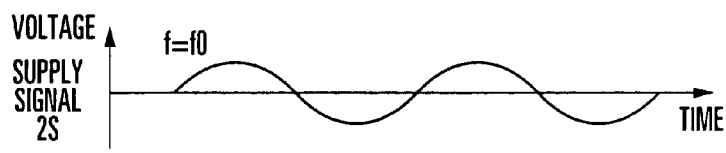
FIGS. 22A to 22D are signal waveform charts showing changes in amplitude with changes in frequency.
Figure 22B:
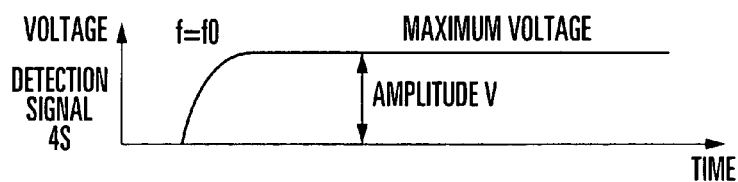
Figure 22C:
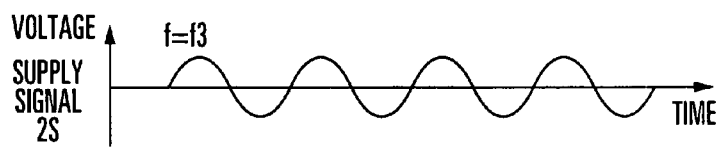
Figure 22D:
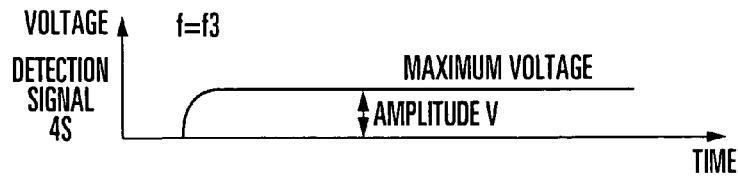

A biometric recognition apparatus according to the 10th embodiment of the present invention will be described next with reference to FIG. 18. FIG. 18 is a block diagram showing the biometric recognition apparatus according to the 10th embodiment of the present invention.

This biometric recognition apparatus is provided with a detection element 1, supply signal generating unit 2, response signal generating unit 3, waveform information detection unit 4, biometric recognition unit 5, and control unit 6.

In this embodiment, when biometric recognition is to be performed on the basis of the impedance of an object, biometric recognition is performed on the basis of waveform information representing the impedance, and biometric recognition is also performed on the basis of a plurality of pieces of biometric information detected at different frequencies. Note that the same reference numerals as in the first embodiment (see FIG. 1) denote the same or equivalent parts in the 10th embodiment.

The detection element 1 electrically contacts an object 10 through a detection electrode, and connects the capacitive and resistive components of the impedance of the object 10 to the response signal generating unit 3. The supply signal generating unit 2 generates a supply signal 2S formed from a sine wave having a predetermined frequency on the basis of a frequency control signal 61S from the control unit 6, and outputs the signal to the response signal generating unit 3. The response signal generating unit 3 applies the supply signal 2S from the supply signal generating unit 2 to the detection element 1, and outputs, to the waveform information detection unit 4, a response signal 3S which changes in accordance with the output impedance of the detection element 1, i.e., the capacitive and resistive components of the impedance of the object 10.

The waveform information detection unit 4 detects a phase difference or an amplitude of the supply signal 2S from the waveform represented by the response signal 3S from the response signal generating unit 3, and outputs a detection signal 4S containing waveform information representing such a phase difference or amplitude to the biometric recognition unit 5. The biometric recognition unit 5 recognizes/determines, on the basis of the waveform information contained in the detection signal 4S from the waveform information detection unit 4 which is obtained for each of the supply signals 2S having different frequencies, whether or not the object 10 is a living body, and outputs a recognition result 5S. The control unit 6 is comprised of a CPU, a logic circuit, and the like, and outputs the frequency control signal 61S and a determination control signal 62S at a predetermined timing.

The operation of the biometric recognition apparatus according to this embodiment will be described next. The object 10 is connected to the output stage of the response signal generating unit 3 through the detection element 1. In this case, the intrinsic impedance of the object 10 can be represented by the capacitive and resistive components connected between the output stage of the response signal generating unit 3 and a common potential (low impedance) such as ground potential through the detection element 1.

The supply signal 2S applied from the response signal generating unit 3 with a predetermined output impedance is therefore voltage-divided by the output impedance and the intrinsic impedance of the object 10. The current flowing in the object 10 then changes in phase or amplitude in accordance with the intrinsic impedance of the object 10. Such a change is converted into a voltage and output as the response signal 3S.

The response signal 3S is input to the waveform information detection unit 4, in which the above change in phase or amplitude is detected as the information of a waveform, i.e., waveform information. In this case, as indicated by the signal waveform charts of FIGS. 19A to 19D, a phase difference $\phi$ between the supply signal 2S and the response signal 3S can be detected by comparing the phase of a reference signal synchronized with the supply signal 2S with the response signal 3S using, for example, a phase comparison circuit. In addition, as shown in FIGS. 20A to 20C, by measuring the maximum voltage value of the response signal 3S using, for example, a sample/hold circuit, an amplitude V of the response signal 3S can be detected.

The detection signal 4S containing the waveform information detected in this manner is output from the waveform information detection unit 4.

The biometric recognition unit 5 compares the recognition index value obtained from the waveform information contained in the detection signal 4S from the waveform information detection unit 4 with a reference range indicating the recognition index values of the authentic living body to recognize/determine whether or not the object 10 is a living body. The biometric recognition unit 5 then outputs the recognition result 5S to the object 10.

In this case, the biometric recognition unit 5 determines whether or not the object 10 is a living body, on the basis of the determination control signal 62S from the control unit 6, by using the recognition index value obtained from each of the supply signals 2S having different frequencies. If all the recognition index values fall within the reference range, the biometric recognition unit 5 outputs the recognition result 5S indicating that the object 10 is the authentic living body. If any one of the recognition index values falls outside the reference range, the biometric recognition unit 5 outputs the recognition result 5S indicating that the object 10 is not the authentic living body.

As described above, the impedance of the authentic living body can be represented by capacitive and resistive components. The magnitude of the impedance therefore changes with a change in frequency due to the capacitive component, i.e., the imaginary component. As shown in FIGS. 21A to 21D, therefore, at predetermined frequency f=f0 and higher frequency f=f3 (f0<f3), the phase difference $\phi$ with respect to the supply signal 2S which is obtained as the waveform information of the response signal 3S changes. In addition, as shown in FIGS. 22A to 22D, at frequency f=f0 and frequency f=f3, the amplitude V obtained as the waveform information of the response signal 3S changes.

Figure 23:
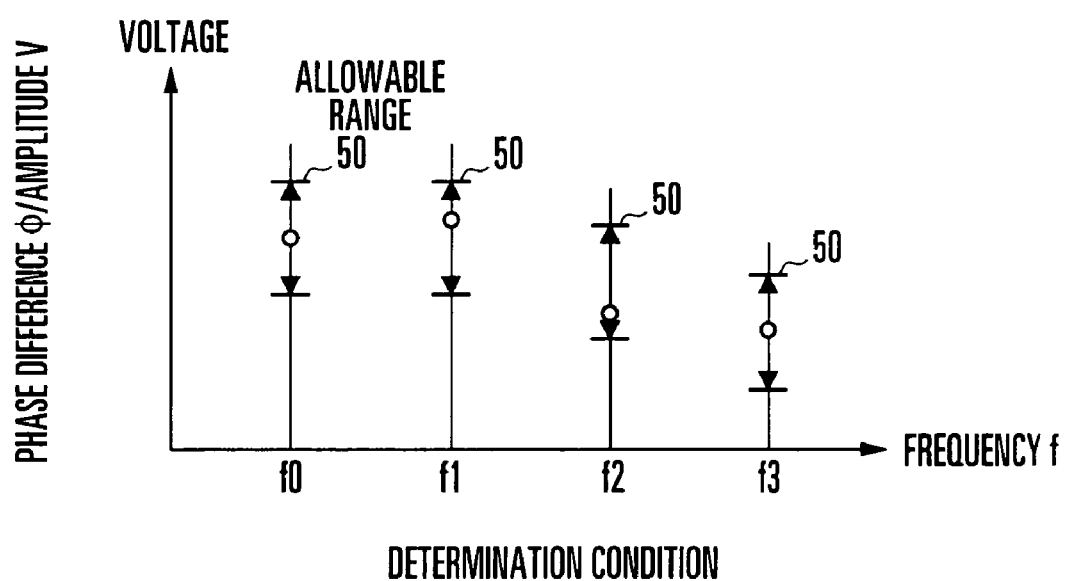
FIG. 23 is a view for explaining reference ranges corresponding to recognition index values.

In comparing each recognition index value with a reference range, the biometric recognition unit 5 uses a reference range 50 indicating the recognition index values of the authentic living body for a measurement condition under which each recognition index value is obtained, i.e., each frequency f of the supply signal 2S, as shown in FIG. 23. This can realize high-precision recognition/determination using different measurement conditions for the object 10, thereby obtaining high security against fraudulent activities using an artificial finger and the like. Note that reference ranges for the respective measurement conditions may be set in the biometric recognition unit 5 in advance or information notified from the control unit 6 may be used.

In this manner, the waveform information detection unit 4 detects waveform information such as a phase difference or amplitude representing the waveform of the response signal 3S from the response signal 3S which has changed in accordance with the impedance of the object 10, and biometric recognition for the object 10 is performed on the basis of the recognition index value obtained from the waveform information. This makes it possible to minutely detect information representing an electrical characteristic of the object by using a phase comparison circuit such as a general comparator or logic circuit, which is a very simple circuit arrangement as compared with the prior art, without requiring a resistive element or capacitive element which requires a large area. This in turn can easily realize a reduction in the size of the biometric recognition apparatus and the formation of a chip.

Since biometric recognition for the object 10 is performed by using a plurality of recognition index values obtained from the supply signals 2S having different frequencies, it is difficult to fake the impedances at the respective frequencies. This can realize high-precision recognition/determination using different measurement conditions for the object 10, thereby obtaining high security against fraudulent activities using an artificial finger and the like.

In this case, biometric recognition is performed by using recognition index values at a plurality of discretely selected frequencies as measurement conditions for the acquisition of recognition index values, frequencies in this case. For this reason, there is no need to perform determination by detecting continuous frequency characteristics in a frequency region having a width. This makes it possible to shorten the time required for recognition/determination operation and obtain sufficient determination precision with a simple circuit arrangement.

11th Embodiment

Figure 24:
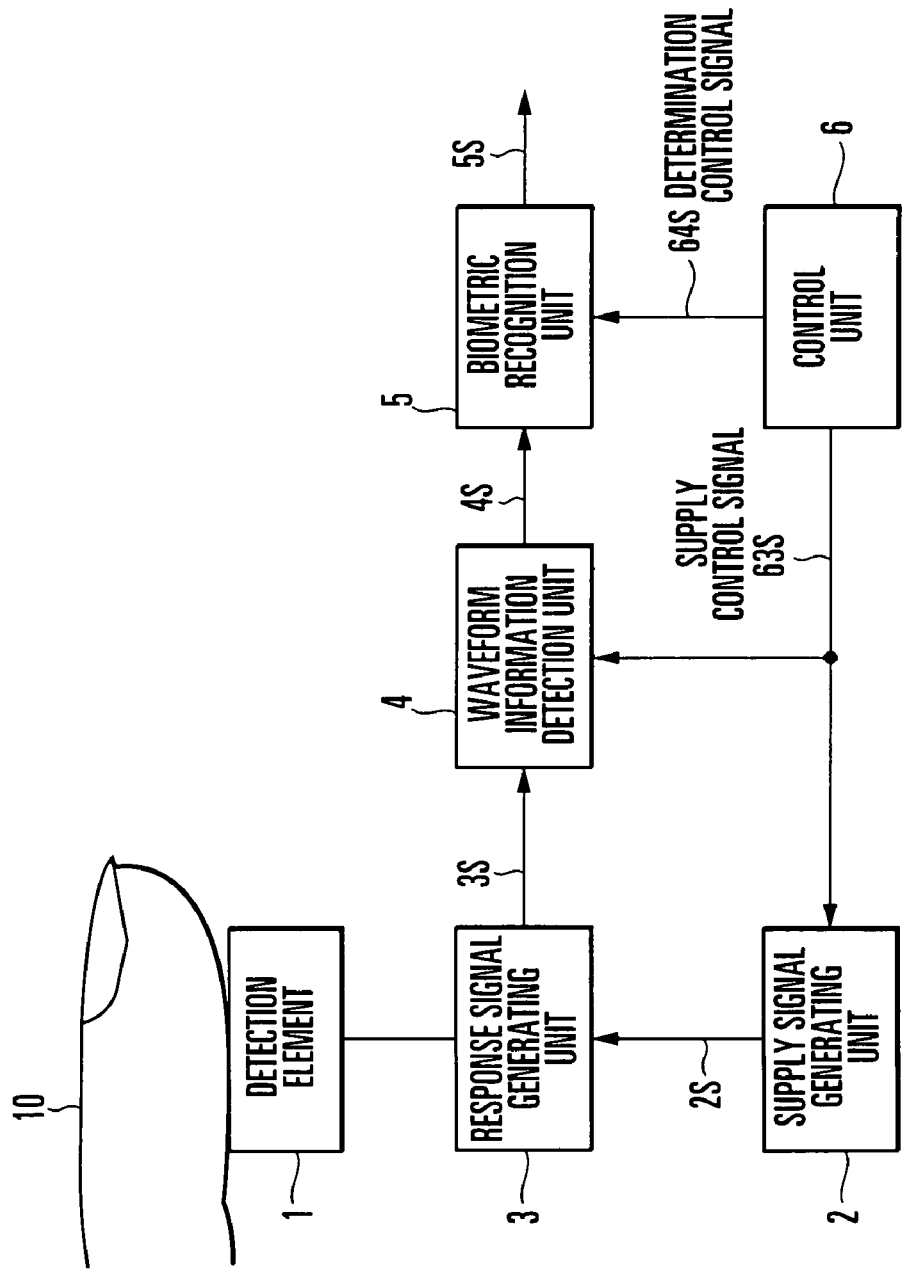
FIG. 24 is a block diagram showing the arrangement of a biometric recognition apparatus according to the 11th embodiment of the present invention.

A biometric recognition apparatus according to the 11th embodiment of the present invention will be described next with reference to FIG. 24. FIG. 24 is a block diagram showing the biometric recognition apparatus according to the 11th embodiment of the present invention.

The 10th embodiment (see FIG. 18) has exemplified the case wherein measurement conditions for the acquisition of recognition index values from the object 10 are set by changing the frequency of the supply signal 2S. In the 11th embodiment, measurement conditions for the acquisition of recognition index values from the object 10 are set by changing the elapsed time from the start of the application of the supply signal 2S. Note that the same reference numerals as in FIG. 18 denote the same or equivalent parts in FIG. 24.

A control unit 6 is comprised of a CPU, a logic circuit, and the like, and outputs a supply control signal 63S and determination control signal 64S at a predetermined timing. A supply signal generating unit 2 starts supplying the supply signal 2S having a predetermined frequency on the basis of the supply control signal 63S from the control unit 6. In response to this operation, a response signal generating unit 3 starts applying the supply signal 2S to the object 10 through a detection element 1, and outputs a response signal 3S which has changed in phase and amplitude in accordance with the impedance of the object 10 to a waveform information detection unit 4. The waveform information detection unit 4 detects waveform information representing a phase difference or an amplitude of the supply signal 2S from the response signal 3S on the basis of the supply control signal 63S from the control unit 6, and outputs the information as a detection signal 4S. Note that the operation of the waveform information detection unit 4 is the same as that described above, and hence a description thereof will be omitted.

A biometric recognition unit 5 compares the recognition index value obtained by the waveform information detection unit 4 from the detection signal 4S with a reference range indicating the recognition index values of the authentic living body at the timing designated by the determination control signal 64S from the control unit 6, i.e., at each of different elapsed times from the start of the application of the supply signal 2S. If all the recognition index values fall within the reference range, a recognition result 5S indicating that the object 10 is the authentic living body is output. If any one of the recognition index values falls outside the reference range, the recognition result 5S indicating that the object 10 is not the authentic living body is output.

As described above, the impedance of the authentic living body can be represented by capacitive and resistive components. In this case, the contact resistance between the detection element 1 and the living body changes with time due to perspiration from the skin of the living body and the like. As a consequence, the impedance of the object 10 changes when viewed from the detection element 1. As shown in FIGS. 25A to 25C, therefore, a phase difference $\phi$ with respect to the supply signal 2S which is obtained as the waveform information of the response signal 3S changes between elapsed time $T=T0$ from the start of the application of the supply signal 2S after the contact of the object 10 with the detection element 1 and elapsed time $T=T3$ ($T0<T3$) longer than elapsed time $T=T0$. In addition, as shown in FIGS. 26A to 26C, the amplitude V obtained as waveform information of the response signal 3S also changes between elapsed time $T=T0$ and elapsed time $T=T3$.

Figure 27:
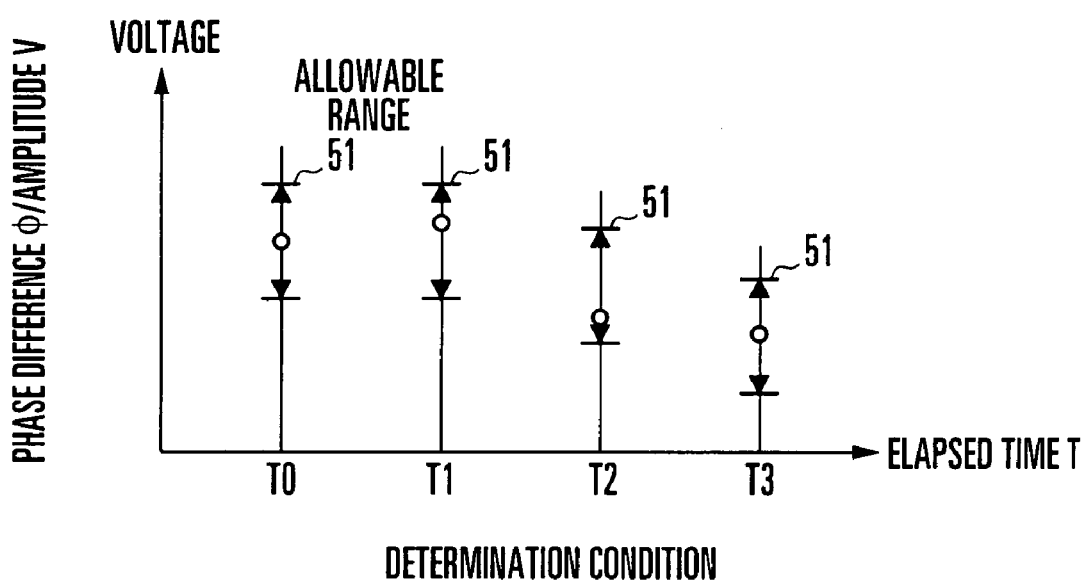
FIG. 27 is a view for explaining reference ranges corresponding to recognition index values.

In comparing each recognition index value with a reference range, the biometric recognition unit 5 uses a reference range 51 indicating the recognition index values of the authentic living body for a measurement condition under which each recognition index value is obtained, i.e., each elapsed time T from the start of the application of the supply signal 2S, as shown in FIG. 27. This can realize high-precision recognition/determination using different measurement conditions for the object 10, thereby obtaining high security against fraudulent activities using an artificial finger and the like. Note that reference ranges for the respective measurement conditions may be set in the biometric recognition unit 5 in advance or information notified from the control unit 6 may be used.

In this manner, the waveform information detection unit 4 detects waveform information such as a phase difference or amplitude representing the waveform of the response signal 3S from the response signal 3S which has changed in accordance with the impedance of the object 10, and biometric recognition for the object 10 is performed on the basis of the recognition index value obtained from the waveform information. This makes it possible to minutely detect information representing an electrical characteristic of the object by using a phase comparison circuit such as a general comparator or logic circuit, which is a very simple circuit arrangement as compared with the prior art, without requiring a resistive element or capacitive element which requires a large area. This in turn can easily realize a reduction in the size of the biometric recognition apparatus and the formation of a chip.

Since biometric recognition for the object 10 is performed by using a plurality of recognition index values obtained at the respective elapsed times from the start of the application of the supply signal 2S, high-precision recognition/determination using different measurement conditions for the object 10 can be realized, thereby obtaining high security against fraudulent activities using an artificial finger and the like.

In this case, biometric recognition is performed by using recognition index values at a plurality of discretely selected elapsed times as measurement conditions for the acquisition of recognition index values, elapsed times in this case. For this reason, there is no need to perform determination by detecting continuous elapsed time characteristics in an elapsed time region having a width. This makes it possible to shorten the time required for recognition/determination operation and obtain sufficient determination precision with a simple circuit arrangement.

Each of the 10th and 11th embodiments described above has exemplified the case wherein in performing comprehensive determination/recognition by using a plurality of recognition index values, the biometric recognition unit 5 determines that the object 10 is the authentic living body, only when all the recognition index values fall within the reference range. However, the present invention is not limited to this. For example, comprehensive recognition/determination may be performed on the basis of a condition about the number of recognition index values, of the respective recognition index values, which are determined to fall within the reference range, for example, one, a predetermined number or more, or a majority. This can perform stable recognition/determination against accidental noise and the like.

Each of the 10th and 11th embodiments described above has exemplified the case wherein when each recognition index value is to be compared with a reference range, a reference range corresponding to each measurement condition is used. However, the present invention is not limited to this. For example, a common reference range covering the recognition index values of an authentic living body which are obtained in the respective measurement conditions may be used. This makes it possible to simplify the circuit arrangement as compared with the case wherein determination is performed by using a plurality of reference ranges.

According to another method of making the biometric recognition unit 5 perform comprehensive determination/recognition by using a plurality of recognition index values, a representative value of the respective recognition index values may be obtained by statistical processing, and determination recognition may be performed by comparing the representative value with a reference range indicating the recognition index values of the authentic living body. As this representative value, various kinds of statistical values such as a mean value, median value, maximum value, and minimum value can be used. This makes it possible to perform determination by using one reference range and hence simplify the circuit arrangement as compared with the case wherein determination is performed by using a plurality of reference ranges. In addition, using a statistical value, e.g., a mean value or median value, obtained from a plurality of recognition index values can realize stable recognition/determination against accidental noise.

Each of the 10th and 11th embodiments has exemplified the case wherein measurement conditions are set by changing the frequency of the supply signal 2S or the elapsed time from the start of the application of the supply signal. However, biometric recognition may be performed on the basis of a plurality of recognition index values obtained by combining these measurement conditions. This can realize biometric recognition with higher precision and security. Note that measurement conditions are not limited to the frequency of the supply signal 2S and elapsed times, and other measurement conditions may be used.

Furthermore, each of the 10th and 11th embodiments has exemplified the case wherein as waveform information of the response signal 3S, a phase difference or amplitude is used. However, the waveform information detection unit 4 may detect both pieces of waveform information, and the biometric recognition unit 5 may perform recognition/determination with respect to the respective recognition index values obtained from the two pieces of waveform information. This can realize biometric recognition with higher precision and security.

12th Embodiment

Figure 28:
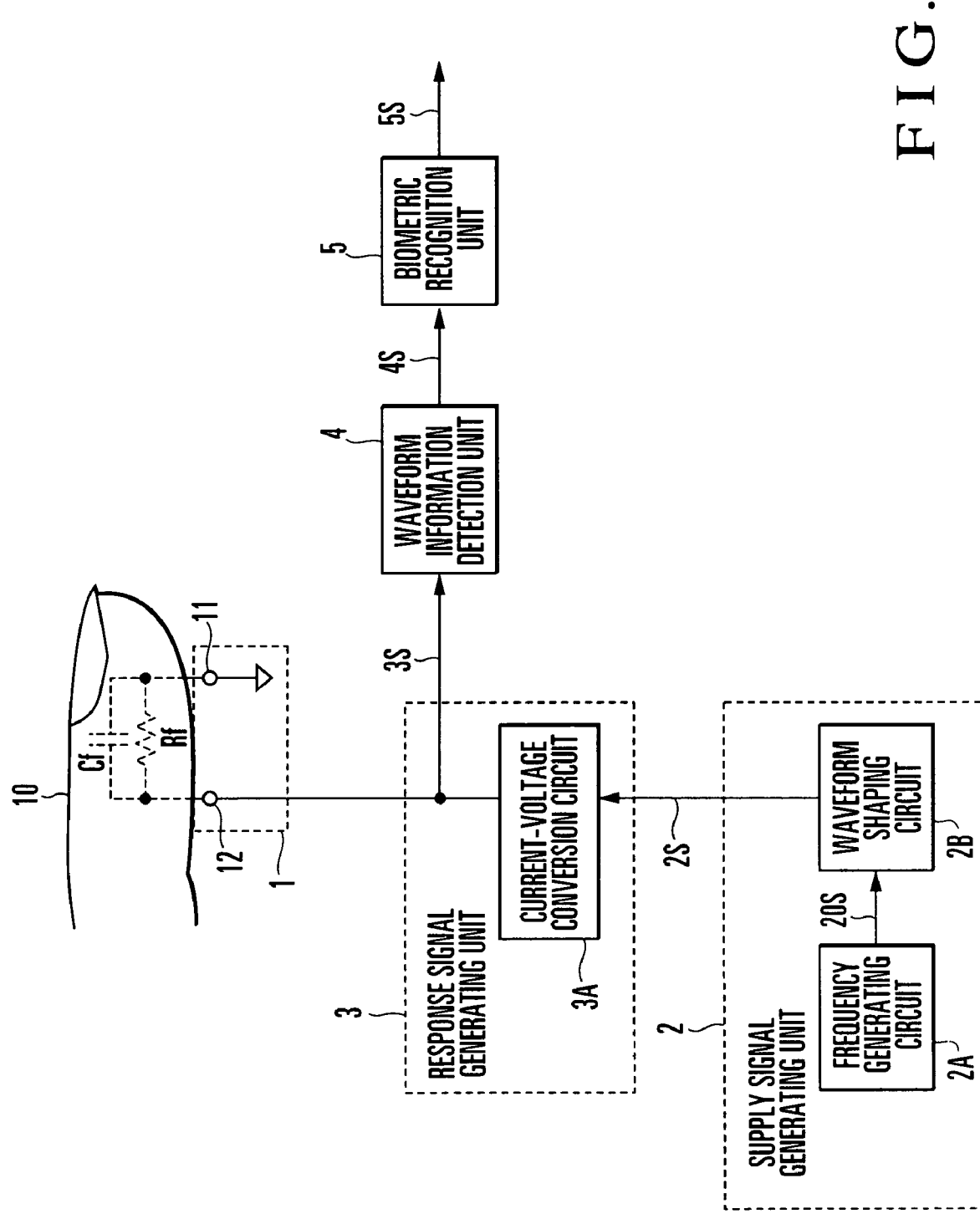
FIG. 28 is a block diagram showing the arrangement of a biometric recognition apparatus according to the 12th embodiment of the present invention.

A biometric recognition apparatus according to the 12th embodiment of the present invention will be described next with reference to FIG. 28. FIG. 28 is a block diagram showing the biometric recognition apparatus according to the 12th embodiment of the present invention.

This biometric recognition apparatus is provided with a detection element 1, supply signal generating unit 2, response signal generating unit 3, waveform information detection unit 4, and biometric recognition unit 5.

The detection element 1 electrically contacts an object 10 through a detection electrode, and connects the capacitive and resistive components of the impedance of the object 10 to the response signal generating unit 3. The supply signal generating unit 2 is comprised of a frequency generating circuit 2A and waveform shaping circuit 2B. The supply signal generating unit 2 generates an AC supply signal 2S by making the waveform shaping circuit 2B extract a desired frequency component from a rectangular wave signal 20S having a predetermined frequency which is generated by the frequency generating circuit 2A, and outputs the signal to the response signal generating unit 3. The response signal generating unit 3 applies the supply signal 2S from the supply signal generating unit 2 to the detection element 1 through a current-voltage conversion circuit 3A, and outputs, to the waveform information detection unit 4, a response signal 3S which changes in accordance with the output impedance of the detection element 1, i.e., a capacitive component Cf and resistive component Rf of the impedance of the object 10.

The waveform information detection unit 4 detects a phase difference or amplitude of the supply signal 2S from the waveform represented by the response signal 3S from the response signal generating unit 3, and outputs a detection signal 4S containing waveform information representing the phase difference or an amplitude to the biometric recognition unit 5. In this case, the waveform information detection unit 4 may detect a phase which changes in accordance with the intrinsic capacitive component of the object 10 as waveform information representing the waveform of the response signal 3S by making a phase comparator or the like compare the phase of the response signal 3S with, for example, that of a predetermined reference signal such as the supply signal 2S. Alternatively, the waveform information detection unit 4 may detect an amplitude which changes in accordance with the intrinsic resistive component of the object 10 as waveform information representing the waveform of the response signal 3S by using a comparator and the like.

The biometric recognition unit 5 recognizes/determines on the basis of the waveform information contained in the detection signal 4S from the waveform information detection unit 4 whether or not the object 10 is a living body, and outputs a recognition result 5S.

The operation of the biometric recognition apparatus according to this embodiment will be described next. When the object 10 contacts terminals 11 and 12 of the detection element 1, the supply signal 2S applied from the supply signal generating unit 2 to the detection element 1 changes in accordance with the intrinsic impedance of the object 10, i.e., the capacitive component Cf and resistive component Rf, and the resultant signal is output as the response signal 3S from the response signal generating unit 3. The waveform information detection unit 4 detects a phase difference or amplitude from the response signal 3S, and outputs a detection signal 4S containing information indicating the detection result to the biometric recognition unit 5.

The biometric recognition unit 5 recognizes/determines whether or not the object 10 is a living body, on the basis of whether or not the waveform information contained in the detection signal 4S falls within the reference range of the waveform information of the authentic living body, and outputs the recognition result 5S.

As described above, in this embodiment, the waveform information detection unit 4 is provided to detect waveform impedance representing a phase difference or an amplitude of the response signal 3S so as to detect information representing the real or imaginary component of the intrinsic impedance of the object 10. The biometric recognition unit 5 then determines on the basis of the detected information whether or not the object 10 is a living body. This makes it possible to closely examine an electrical characteristic of an object with a relatively simple circuit arrangement which detects waveform information, as compared with the prior art, without requiring any external components such as transistors, inductances, and capacitances. This in turn can realize a reduction in the size of the biometric recognition apparatus and the formation of a chip.

In addition, since the waveform information detection unit 4 detects waveform information representing a phase difference with respect to the response signal 3S or an amplitude without using any impedance matching with the object 10, there is no need to use a high-precision sine wave signal without any distortion as the supply signal 2S. In this embodiment, therefore, the supply signal generating unit 2 generates the supply signal 2S formed from a pseudo sine wave by making the waveform shaping circuit 2B extract a desired frequency component from the rectangular wave signal 20S generated by the frequency generating circuit 2A. This makes it possible to greatly reduce the circuit arrangement size as compared with a circuit which generates a high-precision sine wave signal. This in turn can realize a reduction in the size of the biometric recognition apparatus and the formation of a chip.

Figure 29:
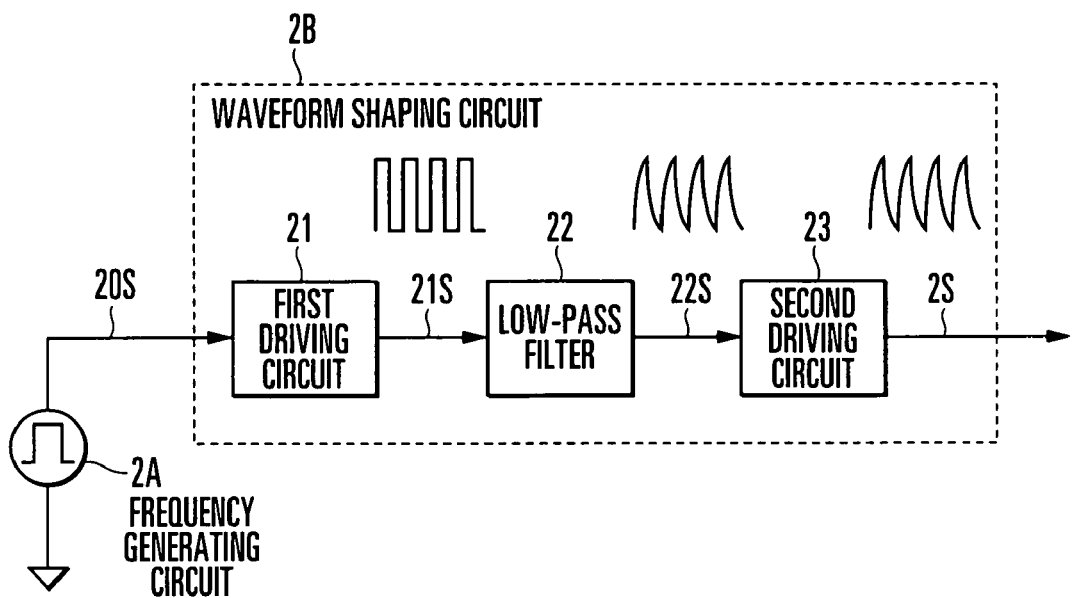
FIG. 29 is a view showing an example of the arrangement of a waveform shaping circuit used in FIG. 28.

FIG. 29 shows an example of the circuit arrangement of the waveform shaping circuit 2B. The waveform shaping circuit 2B is comprised of a first driving circuit 21, low-pass filter 22, and second driving circuit 23.

The first driving circuit 21 is formed from a buffer circuit such as an inverter circuit which serves to drive the subsequent circuit. The first driving circuit 21 receives the rectangular wave signal 20S output from the frequency generating circuit 2A and outputs a rectangular wave signal 21S with a low impedance. Note that as the frequency generating circuit 2A, for example, a known pulse generating circuit using a quartz oscillator may be used.

Figure 30:
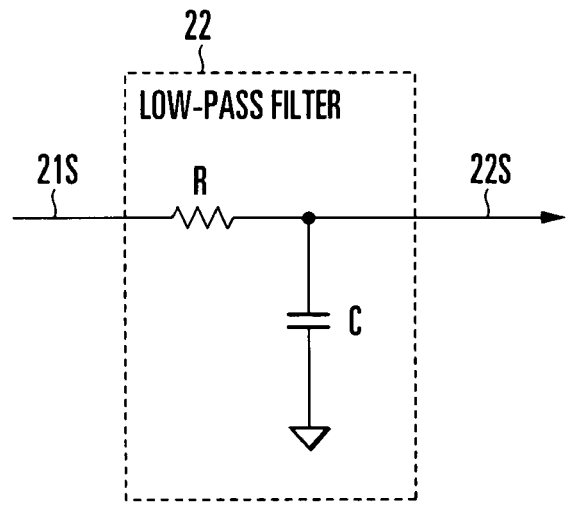
FIG. 30 is a view showing an example of the arrangement of a low-pass filter used in FIG. 29.

As the low-pass filter 22, an RC low-pass filter like the one shown in FIG. 30 may be used. Although this circuit example is comprised of a resistive element R and capacitive element C, the low-pass filter may have an arrangement using only capacitance or resistance which is latent in the circuit. The low-pass filter 22 extracts a desired frequency component from the rectangular wave signal 21S and obtains a low-frequency signal 22S having a waveform obtained by rounding the rectangular pulse.

The second driving circuit 23 is formed from a circuit for driving the subsequent circuit as in the case with the first driving circuit 21, and outputs the signal output from the low-pass filter 22 as the supply signal 2S with a low impedance. As the second driving circuit 23, for example, an impedance conversion circuit having an arrangement in which the inverting input of a differential amplification circuit is connected to the output.

As described above, since the low-pass filter 22 which extracts a desired low-frequency component from the rectangular wave signal 20S from the frequency generating circuit 2A is used as the waveform shaping circuit 2B, for example, the desired supply signal 2S can be obtained with a very simple circuit arrangement like that is constituted by the resistive element R and capacitive element C. This can realize a reduction in the biometric recognition apparatus and the formation of a chip.

In addition, the conventional digital waveform generating circuit needs to use an A/D converter and memory each requiring a mount area of several mm square. In contrast, according to this embodiment, the circuit can be mounted in an area of several 10 μm square.

13th Embodiment

Figure 31:
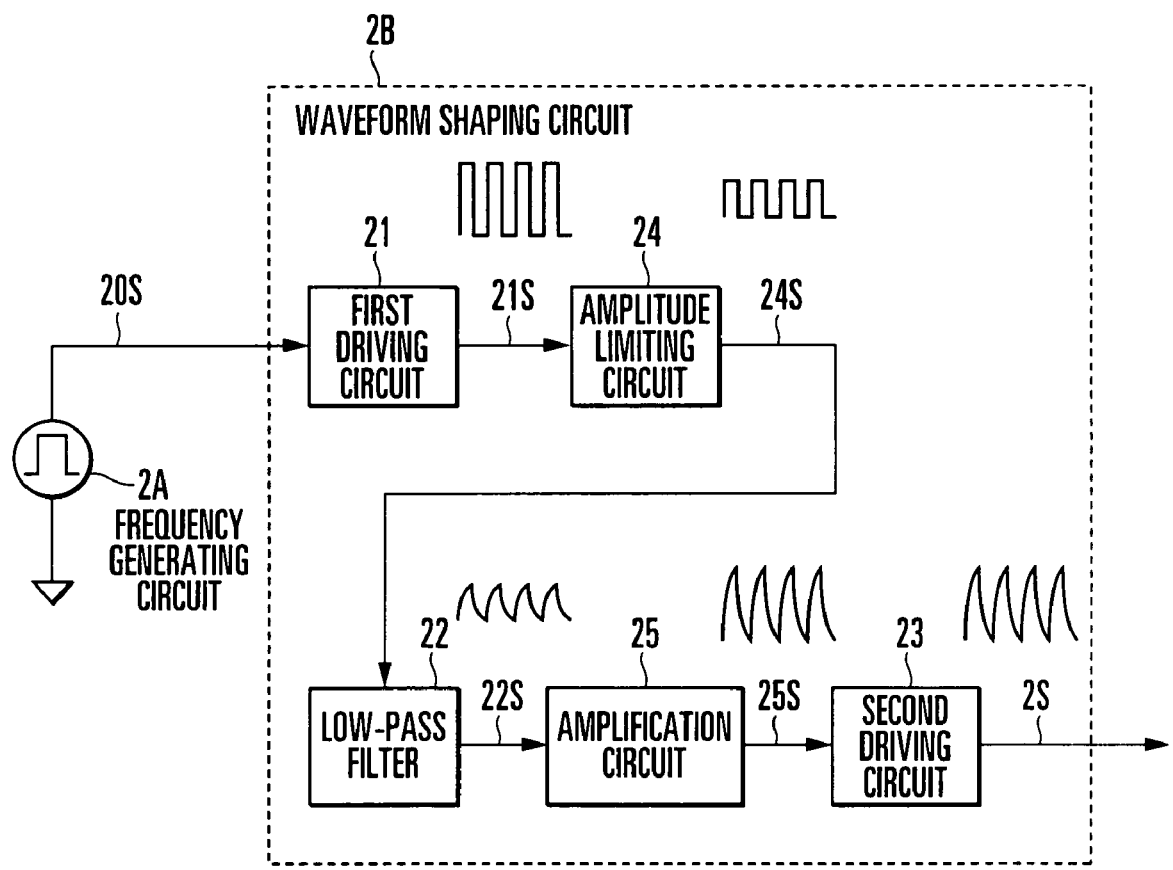
FIG. 31 is a view showing an example of the arrangement of a waveform shaping circuit used in a biometric recognition apparatus according to the 13th embodiment of the present invention.

A biometric recognition apparatus according to the 13th embodiment of the present invention will be described next with reference to FIG. 31. FIG. 31 shows an example of the circuit arrangement of a waveform shaping circuit 2B used in the biometric recognition apparatus according to the 13th embodiment. The biometric recognition apparatus according to this embodiment is equivalent to the above biometric recognition apparatus shown in FIG. 28 which uses the waveform shaping circuit 2B in FIG. 31. The arrangement of this embodiment is the same as that described above except for the waveform shaping circuit 2B, and hence a description thereof will be omitted.

The arrangement of the waveform shaping circuit 2B is the same as that of the above biometric recognition apparatus in FIG. 29 except that an amplitude limiting circuit 24 and amplification circuit 25 are added. The same reference numerals as in FIG. 29 denote the same or equivalent parts in FIG. 31.

The amplitude limiting circuit 24 is a circuit which limits the amplitude of a rectangular wave signal 21S and outputs a rectangular wave limited signal 24S. The amplification circuit 25 is a circuit which amplifies a signal obtained from a low-pass filter 22 and outputs the resultant signal as an amplified signal 25S to a second driving circuit 23.

With this operation, the limited signal 24S smaller in amplitude than the rectangular wave signal 21S passes through the low-pass filter 22. This makes it possible to reduce the resistance value of a resistive element or the capacitance value of a capacitive element which is used in the low-pass filter 22, thus reducing the layout area required to form such circuit elements on a chip.

FIG. 32 shows an example of the circuit arrangement of the amplitude limiting circuit. The amplitude limiting circuit 24 is comprised of an inverter circuit 200, first reference voltage generating circuit 201, second reference voltage generating circuit 202, first switch element 211, and second switch element 212.

The inverter circuit 200 outputs the rectangular wave signal 21S upon inverting its logical value. The first switch element 211 performs switching (ON/OFF) operation in accordance with an inverted output from the inverter circuit 200, and intermittently outputs a first reference voltage Vref1 as the limited signal 24S from the first reference voltage generating circuit 201. The second switch element 212 performs switching (ON/OFF) operation in accordance with the rectangular wave signal 21S, and intermittently outputs a second reference voltage Vref2 as the limited signal 24S from the second reference voltage generating circuit 202.

As shown in FIG. 33, the first reference voltage Vref1 is set at a potential between a central potential V3 of the input rectangular wave signal 21S and a first common potential V1 (LOW level potential), and the second reference voltage Vref2 is set at a potential between the central potential V3 of the rectangular wave signal 21S and a second common potential V2 (HIGH level potential: V2>V1). Note that as these common potentials, low impedance potentials such as various kinds of power supply potentials are used.

In this case, since the first switch element 211 and second switch element 212 are controlled by opposite logic signals, they perform switching operation in opposite phases. As a consequence, as shown in FIG. 33, the first reference voltage Vref1 and second reference voltage Vref2 are alternately output at opposite timings. The amplitude of the rectangular wave signal 21S is limited to a value between the first reference voltage Vref1 and the second reference voltage Vref2, and the resultant signal is output as the limited signal 24S.

In this manner, in the inverter circuit 200, the two switching elements 211 and 212 are made to alternately perform switching operation to alternately output the first reference voltage Vref1 and the second reference voltage Vref2. This makes it possible to limit the amplitude of the rectangular wave signal 21S with a very simple circuit arrangement, thus reducing the layout area of the circuit.

Note that as the switching elements 211 and 212, semiconductor elements such as MOSFETs may be used.

14th Embodiment

Figure 34:
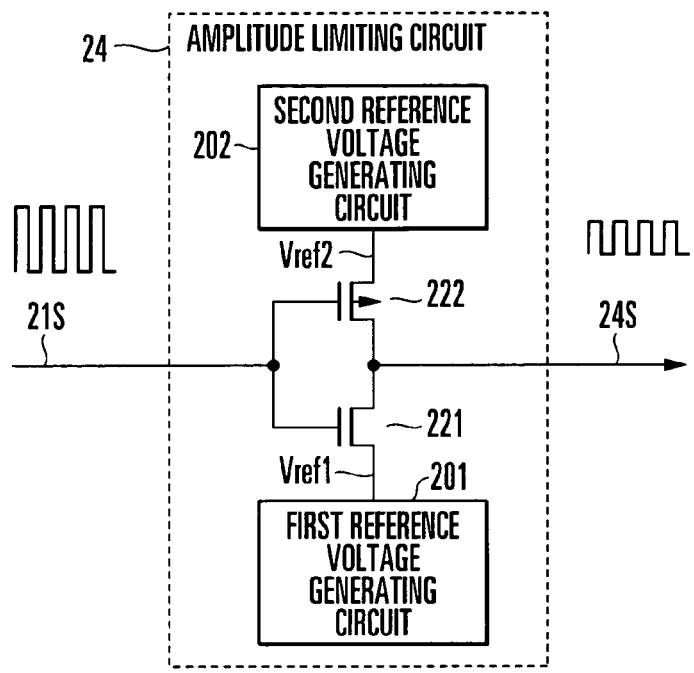
FIG. 34 is a view showing an example of the arrangement of an amplitude limiting circuit used in a biometric recognition apparatus according to the 14th embodiment of the present invention.

A biometric recognition apparatus according to the 14th embodiment of the present invention will be described next with reference to FIG. 34. FIG. 34 shows an example of the circuit arrangement of an amplitude limiting circuit 24 used in the biometric recognition apparatus according to the 14th embodiment. The biometric recognition apparatus according to this embodiment is equivalent to the above biometric recognition apparatus in FIG. 28 which has a waveform shaping circuit 2B in FIG. 31 and further uses the amplitude limiting circuit 24 in FIG. 34 as the amplitude limiting circuit 24. Note that the arrangement of this embodiment is the same as that described above except for the amplitude limiting circuit 24, and a description thereof will be omitted.

The amplitude limiting circuit 24 differs from the above amplitude limiting circuit in FIG. 32 in that it makes two switch elements having different polarities (control logics) alternately perform switching operation at opposite timings instead of making the two switch elements 211 and 212 perform switching operation in the inverter circuit 200.

The amplitude limiting circuit 24 is comprised of a first reference voltage generating circuit 201, second reference voltage generating circuit 202, first switch element 221, and second switch element 222. Referring to FIG. 34, an n-type MOSFET is used as the first switch element 221, and a p-type MOSFET is used as the second switch element 222, which have different polarities (control logics).

A rectangular wave signal 21S is commonly input to the control terminals (gate terminals) of the first switch element 221 and second switch element 222. Their output terminals (drain terminals) are commonly connected and output a limited signal 24S. The first reference voltage generating circuit 201 and second reference voltage generating circuit 202 are respectively connected to the input terminals (source terminals) of the switch elements.

Since the two switch elements 221 and 222 have different polarities, when the rectangular wave signal 21S is at LOW level (V1), the first switch element 221 is set to a high impedance, and the second switch element 222 is set to a low impedance. Consequently, a second reference voltage Vref2 is output as the limited signal 24S. When the rectangular wave signal 21S is set at HIGH level (V2), since the first switch element 221 is set to a low impedance, and the second switch element 222 is set to a high impedance, a first reference voltage Vref1 is output as the limited signal 24S.

With this operation, the amplitude of the rectangular wave signal 21S is limited to obtain the limited signal 24S like the one shown in FIG. 33.

Alternately performing switching operation at opposite timings in accordance with the rectangular wave signal 21S by using the two switch elements with different polarities in this manner makes it possible to further simplify the circuit arrangement of the amplitude limiting circuit as compared with the circuit arrangement in FIG. 32, thereby reducing the layout area of the circuit.

15th Embodiment

Figure 35:
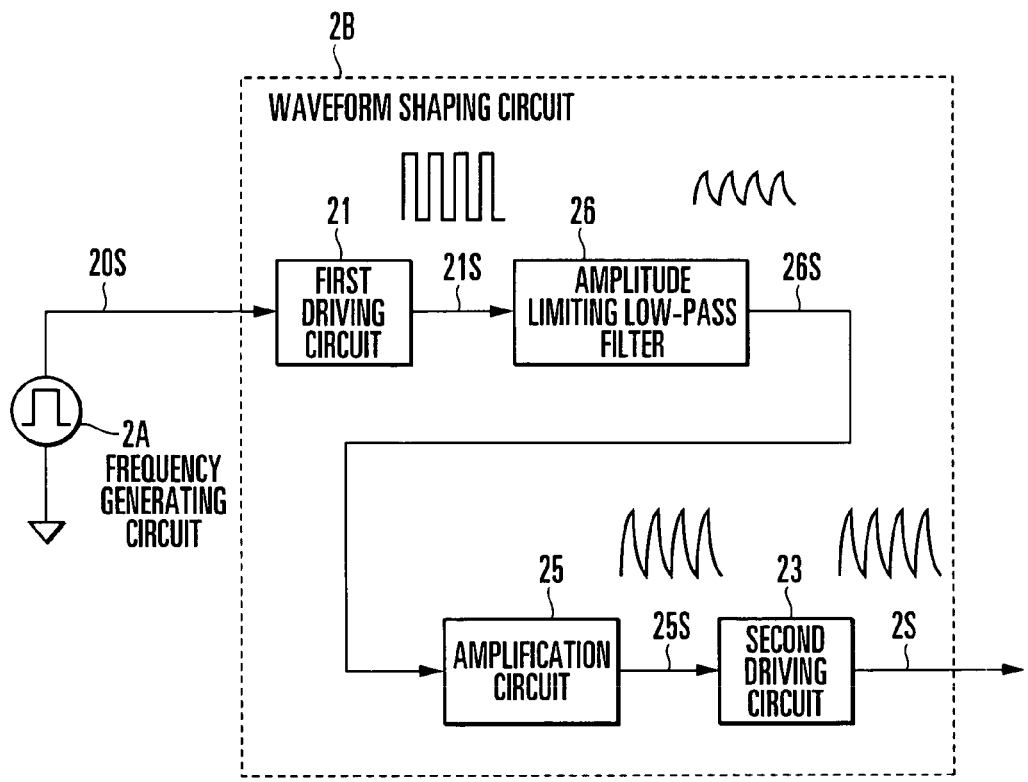
FIG. 35 is a view showing an example of the arrangement of a waveform shaping circuit used in a biometric recognition apparatus according to the 15th embodiment of the present invention.

A biometric recognition apparatus according to the 15th embodiment of the present invention will be described next with reference to FIG. 35. FIG. 35 shows an example of the circuit arrangement of a waveform shaping circuit 2B used in the biometric recognition apparatus according to the 15th embodiment. The biometric recognition apparatus according to this embodiment is equivalent to the above biometric recognition apparatus in FIG. 28 which uses the waveform shaping circuit 2B in FIG. 35. Note that the arrangement of this embodiment is the same as that described above except for the waveform shaping circuit 2B, and hence a description thereof will be omitted.

The arrangement of the waveform shaping circuit 2B is the same as that of the above waveform shaping circuit in FIG. 29 except that a amplitude limiting low-pass filter 26 is used in place of the low-pass filter 22, and an amplification circuit 25 is added. The same reference numerals as in FIG. 29 denote the same or equivalent parts in FIG. 35.

The amplitude limiting low-pass filter 26 is a circuit having both the function of an amplitude limiting circuit 24 which limits the amplitude of a rectangular wave signal 21S and the function of the low-pass filter 22 which extract a desired frequency component.

Figure 36:
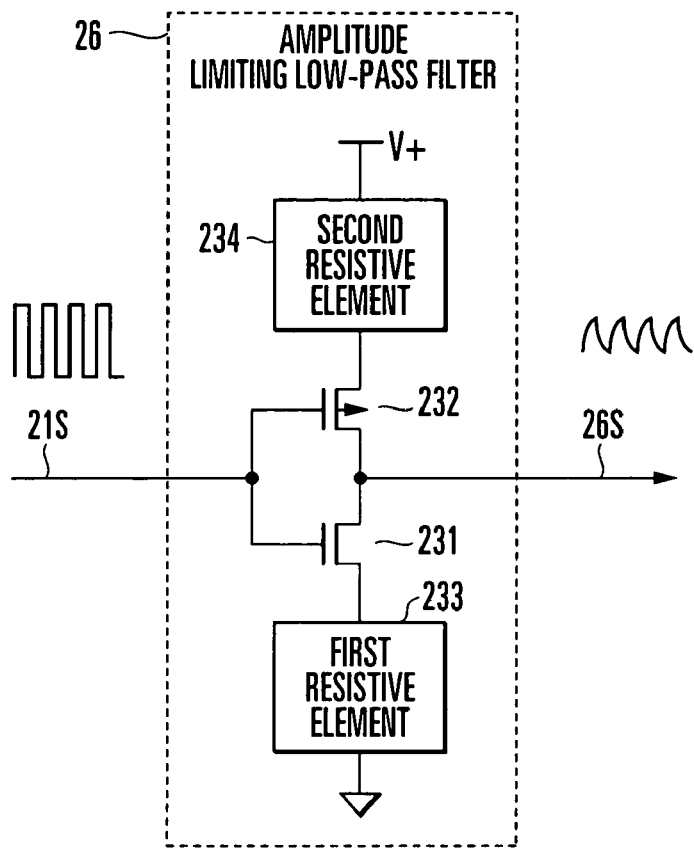
FIG. 36 is a view showing an example of the arrangement of an amplitude limiting low-pass filter used in FIG. 35.

FIG. 36 shows an example of the circuit arrangement of the amplitude limiting low-pass filter 26. The amplitude limiting low-pass filter 26 is comprised of a first switch element 231, second switch element 232, first resistive element 233, and second resistive element 234.

Referring to FIG. 36, an n-type MOSFET is used as the first switch element 231, and a p-type MOSFET is used as the second switch element 232, which have different polarities (control logics). As the first resistive element 233 and second resistive element 234, polysilicon resistors or MOSFETs may be used.

The rectangular wave signal 21S is commonly input to the control terminals (gate terminals) of the first switch element 231 and second switch element 232. Their output terminals (drain terminals) are connected to each other, and a limiting signal 26S is output from them. The input terminal (source terminal) of the first switch element 231 is connected to a first common potential V1 through the first resistive element 233. The input terminal (source terminal) of the second switch element 232 is connected to a second common potential V2 through the second resistive element 234.

Figure 37:
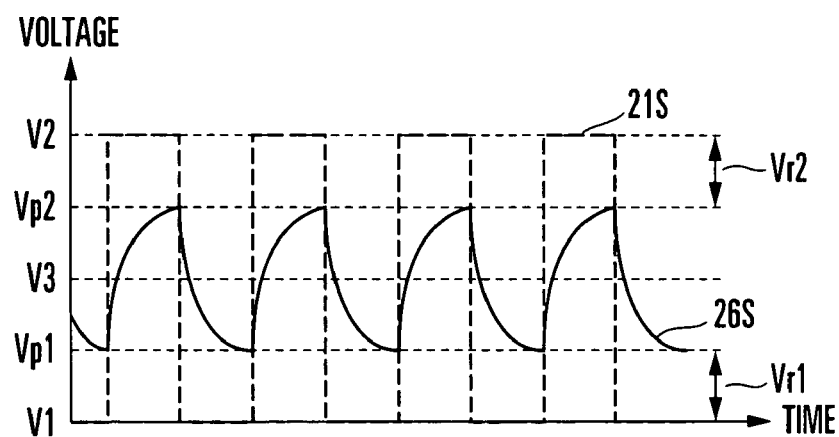
FIG. 37 is a signal waveform chart showing the operation of the amplitude limiting low-pass filter in FIG. 36.

The two switch elements 231 and 232 have different polarities. When, therefore, the rectangular wave signal 21S is set at LOW level (V1), the first switch element 231 is set to a high impedance, and the second switch element 232 is set to a low impedance. Consequently, as shown in FIG. 37, a limited potential Vp2 obtained by subtracting a voltage drop Vr2 due to the second resistive element 234 from the second common potential V2 is output as the limited signal 26S.

In this case, since the second switch element 232 is set to a low impedance through the second resistive element 234 with respect to the second common potential V2, the potential of the output terminal gradually changes. As a result, high-frequency components are cut, and the waveform of the rectangular wave signal 21S is rounded to obtain the limited signal 26S.

When the rectangular wave signal 21S is set at HIGH level (V2), the first switch element 231 is set to a low impedance, and the second switch element 232 is set to a high impedance. As a consequence, as shown in FIG. 37, a limited potential Vp1 obtained by adding a voltage drop Vr1 due to the first resistive element 233 to the first common potential V1 is output as the limited signal 26S.

In this case as well, since the first switch element 231 is set to a low impedance through the first resistive element 233 with respect to the first common potential V1, the potential of the output terminal gradually changes. As a result, high-frequency components are cut, and the waveform of the rectangular wave signal 21S is rounded to obtain the limited signal 26S.

Making the two switch elements having different polarities alternately perform switching operation at opposite timings in accordance with the rectangular wave signal 21S and alternately outputting two potentials through the resistors in this manner can realize both the function of limiting the function of the rectangular wave signal 21S and the function of extracting a desired low-frequency component from the rectangular wave signal 21S. This makes it possible to further simplify the circuit arrangement of the waveform shaping circuit as compared with the above circuit arrangement in FIG. 31, thereby reducing the layout area of the circuit.

16th Embodiment

Figure 38:
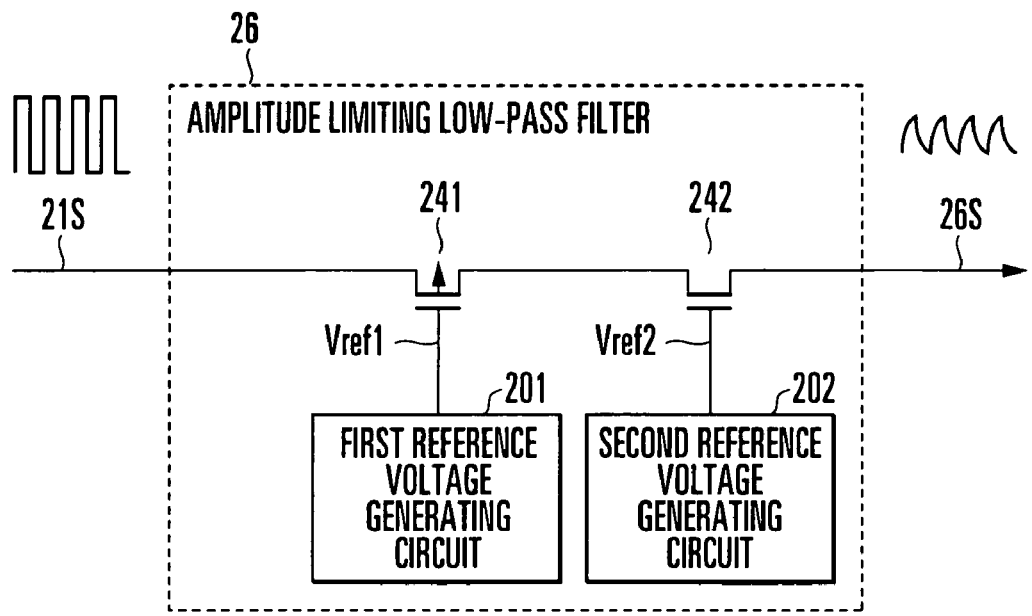
FIG. 38 is a view showing another example of the arrangement of the amplitude limiting low-pass filter used in a biometric recognition apparatus according to the 16th embodiment of the present invention.

A biometric recognition apparatus according to the 16th embodiment of the present invention will be described next with reference to FIG. 38. FIG. 38 shows an example of the circuit arrangement of an amplitude liming circuit low-pass filter used in the biometric recognition apparatus according to the 16th embodiment. The biometric recognition apparatus according to this embodiment is equivalent to the above biometric recognition apparatus in FIG. 28 which uses a waveform shaping circuit 2B in FIG. 35 and also uses an amplitude limiting low-pass filter as the amplitude limiting low-pass filter 26. Note that the arrangement of this embodiment is the same as that described above except for the amplitude limiting low-pass filter 26, and a description thereof will be omitted.

The amplitude limiting low-pass filter 26 is comprised of a first reference voltage generating circuit 201, second reference voltage generating circuit 202, first switch element 241, and second switch element 242.

A first reference voltage Vref1 is supplied to the control terminal (gate terminal) of the first switch element 241. A rectangular wave signal 21S is input to the input terminal (source terminal) of the first switch element 241. A second reference voltage Vref2 is supplied to the control terminal (gate terminal) of the second switch element 242. The output terminal (drain terminal) of the first switch element 241 is connected to the input terminal (source terminal) of the second switch element 242.

Referring to FIG. 38, a p-type MOSFET is used as the first switch element 241, and an n-type MOSFET is used as the second switch element 242, which have different polarities (control logics).

Figure 39:
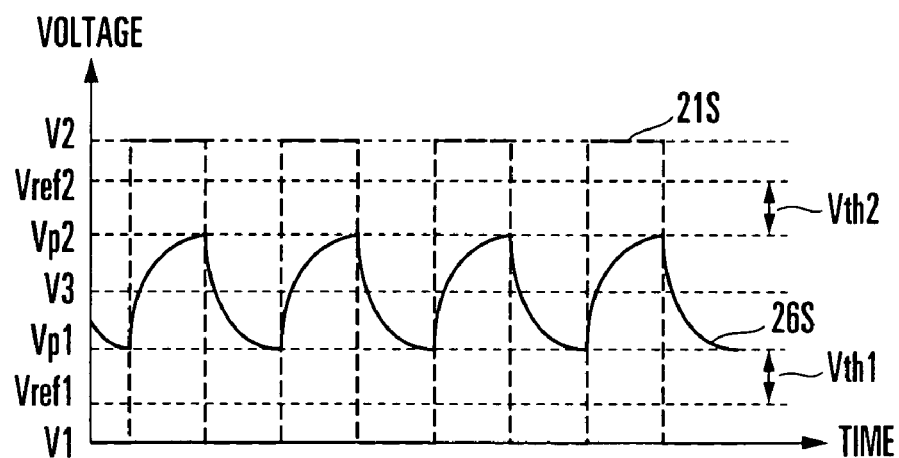
FIG. 39 is a signal waveform chart showing the operation of the amplitude limiting low-pass filter in FIG. 38.

As shown in FIG. 39, the first reference voltage Vref1 is set at a potential between a central potential V3 of the input rectangular wave signal 21S and a first common potential V1 (LOW level potential), and the second reference voltage Vref2 is set at a potential between the central potential V3 of the rectangular wave signal 21S and a second common potential V2 (HIGH level potential: V2>V1). Note that as a common potential for these components, a low impedance potential, e.g., one of various kinds of power supply potentials is used.

When, therefore, the rectangular wave signal 21S is set at LOW level (V1), the input terminal (source terminal) of the first switch element 241 is set at the first common potential V1. Since the control terminal (gate terminal) of the first switch element 241 is at the first reference voltage Vref1, the first switch element 241 is set in a high impedance state. As a consequence, the output terminal (drain terminal) of the first switch element 241 is set at a limited potential Vp1 obtained by adding a threshold voltage Vth1 of the first switch element 241 to the first reference voltage Vref1.

In addition, since the control terminal (gate terminal) of the second switch element 242 is at the second reference voltage Vref2 closer to the second common potential V2 and higher than the limited potential Vp1, the second switch element 242 is set in a low impedance state. As a consequence, a limited signal 26S output from the output terminal (drain terminal) of the second switch element 242 is set at the limited potential Vp1 of the output terminal (drain terminal) of the first switch element 241.

When the rectangular wave signal 21S is set at HIGH level (V2), the input terminal (source terminal) of the first switch element 241 is set at the second common potential V2. Since the control terminal (gate terminal) of the first switch element 241 is at the first reference voltage Vref1, the first switch element 241 is set in a low impedance state. As a consequence, the output terminal (drain terminal) of the first switch element 241 is set at the second common potential V2.

Consequently, the input terminal (source terminal) of the second switch element 242 is set at the second common potential V2. Since the control terminal (gate terminal) of the second switch element 242 is at the second reference voltage Vref2, the second switch element 242 is set in a high impedance state. The output terminal (drain terminal) of the second switch element 242 is therefore set at a limited potential Vp2 obtained by subtracting a threshold voltage Vth2 of the second switch element 242 from the second reference voltage Vref2.

The amplitude of the input rectangular wave signal 21S is therefore limited to a value between the limited potential Vp1 and the limited potential Vp2, and the resultant signal is output as the limited signal 26S.

In this case, when the rectangular wave signal 21S shifts from LOW level (V1) to HIGH level (V2), the first switch element 241 changes from a high impedance state to a low impedance state in a relatively short period of time. On the other hand, since the control terminal (gate terminal) of the second switch element 242 is at the second reference voltage Vref2 lower than the second common potential V2 of the input terminal (source terminal), the driving force of the switch element decreases. As a consequence, it takes time for the second switch element 242 to change from a low impedance state to a high impedance state.

On the contrary, when the rectangular wave signal 21S shifts from HIGH level-(V2) to LOW level (V1), since the control terminal (gate terminal) of the first switch element 241 is at the first reference voltage Vref1 higher than the first common potential V1 of the input terminal (source terminal), the driving force of the switch element decreases. As a consequence, it takes time for the first switch element 241 to change from a low impedance state to a high impedance state.

The potential of the limited signal 26S therefore gradually changes as the impedance of the rectangular wave signal 21S shifts. As a consequence, high-frequency components are cut, and the waveform of the rectangular wave signal 21S is rounded to obtain the limited signal 26S.

In this manner, the switch elements having different polarities are connected in series, and the first and second reference voltages are separately supplied to the control terminals of the respective elements to alternately perform switching operation at opposite timings in accordance with the rectangular wave signal 21S. This makes it possible to realize both the function of limiting the amplitude of the rectangular wave signal 21S and the function of extracting a desired low-frequency component from the rectangular wave signal 21S.

This in turn can simplify the circuit arrangement of the waveform shaping circuit and reduce the layout area of the circuit.

17th Embodiment

Figure 40:
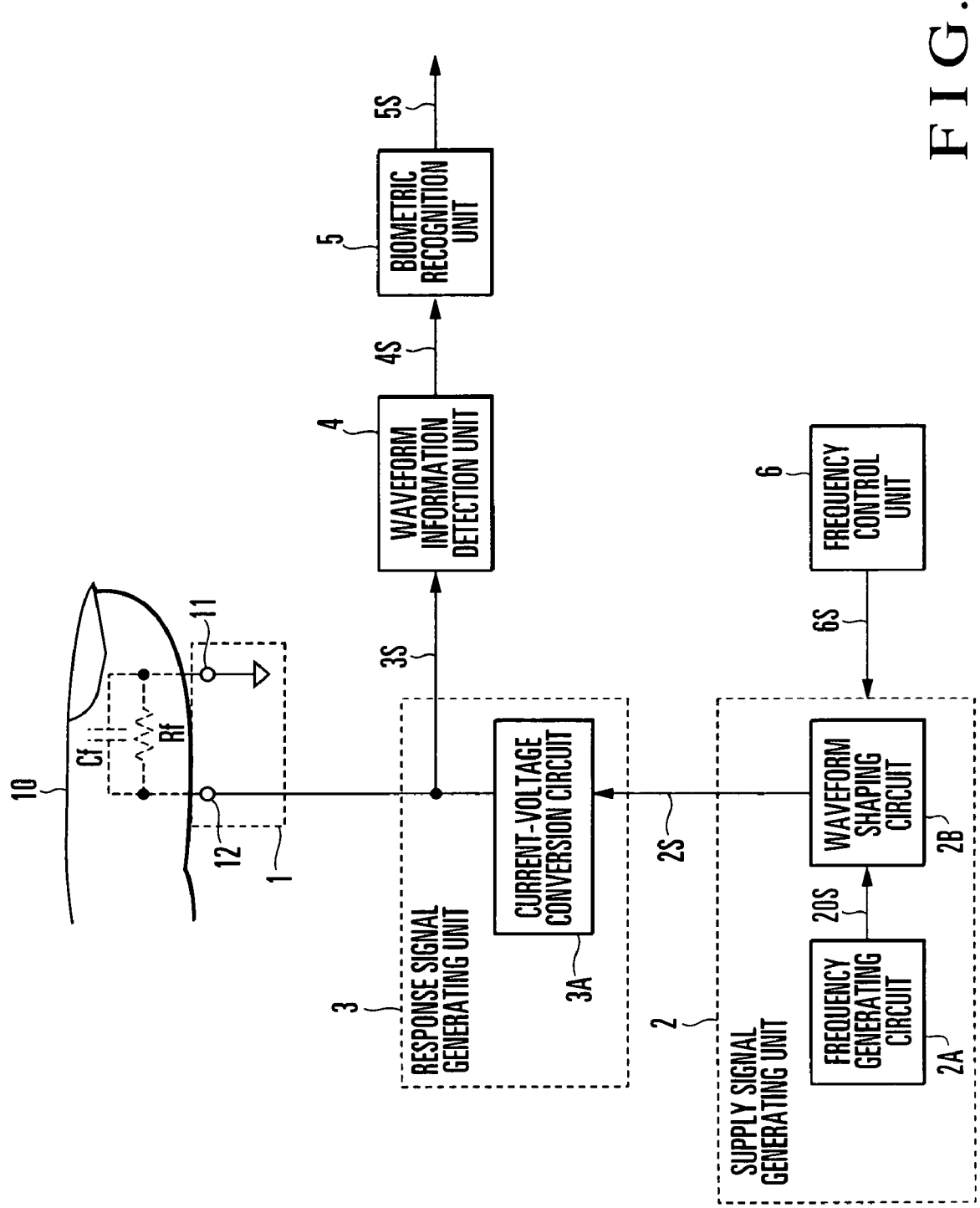
FIG. 40 is a block diagram showing the arrangement of a biometric recognition apparatus according to the 17th embodiment of the present invention.

A biometric recognition apparatus according to the 17th embodiment of the present invention will be described next with reference to FIG. 40. FIG. 40 is a block diagram showing the arrangement of the biometric recognition apparatus according to the 17th embodiment of the present invention. The same reference numerals as in FIG. 28 denote the same or equivalent parts in FIG. 40.

This biometric recognition apparatus has the same arrangement as that of the biometric recognition apparatus according to the 12th embodiment described above except that the apparatus is provided with a frequency control unit 6 which indicates a supply signal 2S to be generated by a supply signal generating unit 2. Note that other arrangements are the same as those in the 12th embodiment, and hence a description thereof will be omitted.

The frequency control unit 6 is comprised of a CPU and logic circuit, and outputs a frequency control signal 6S at a predetermined timing. The supply signal generating unit 2 generates and outputs the supply signal 2S having the frequency designated by the frequency control signal 6S.

With this operation, a biometric recognition unit 5 determines, by using the recognition index value obtained for each of supply signals 2S having different frequencies, whether or not an object 10 is a living body. If all the recognition index values fall within a reference range, the biometric recognition unit 5 outputs a recognition result 5S indicating that the object 10 is the authentic living body. If any one of the recognition index values falls outside the reference range, the biometric recognition unit 5 outputs the recognition result 5S indicating that the object 10 is not the authentic living body.

Since biometric recognition for the object 10 is performed by using a plurality of recognition index values obtained from the supply signals 2S having different frequencies, it is difficult to fake the impedances at the respective frequencies. This can realize high-precision recognition/determination using different measurement conditions for the object 10, thereby obtaining high security against fraudulent activities using an artificial finger and the like.

In this case, biometric recognition is performed by using recognition index values at a plurality of discretely selected frequencies as measurement conditions for the acquisition of recognition index values, frequencies in this case. For this reason, there is no need to perform determination by detecting continuous frequency characteristics in a frequency region having a width. This makes it possible to shorten the time required for recognition/determination operation and obtain sufficient determination precision with a simple circuit arrangement.

A waveform shaping circuit 2B will be described next with reference to FIG. 41. The frequency generating circuit 2A outputs a rectangular wave signal 20S having the frequency indicated by the frequency control signal 6S. For this reason, the waveform shaping circuit 2B must perform waveform shaping processing to keep the amplitude of the supply signal 2S constant even if the frequency of the rectangular wave signal 20S input in accordance with the frequency control signal 6S changes.

Figure 41:
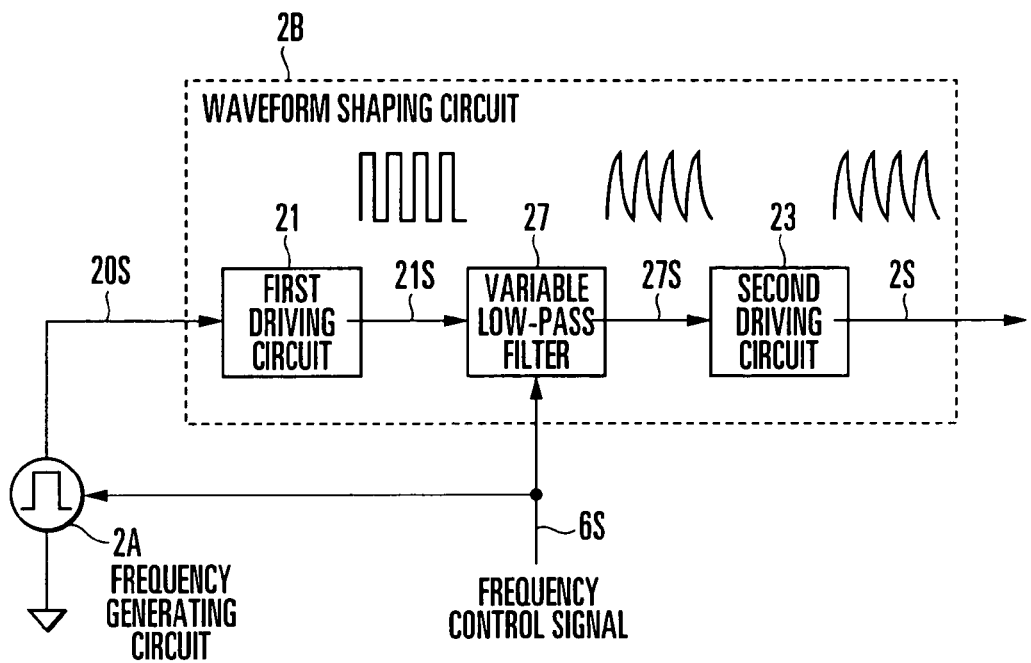
FIG. 41 is a view showing an example of the arrangement of a waveform shaping circuit used in FIG. 40.

The waveform shaping circuit 2B in FIG. 41 copes with each frequency by using a variable low-pass filter 27 in place of the low-pass filter of the waveform shaping circuit in FIG. 29 described above.

Figure 42:
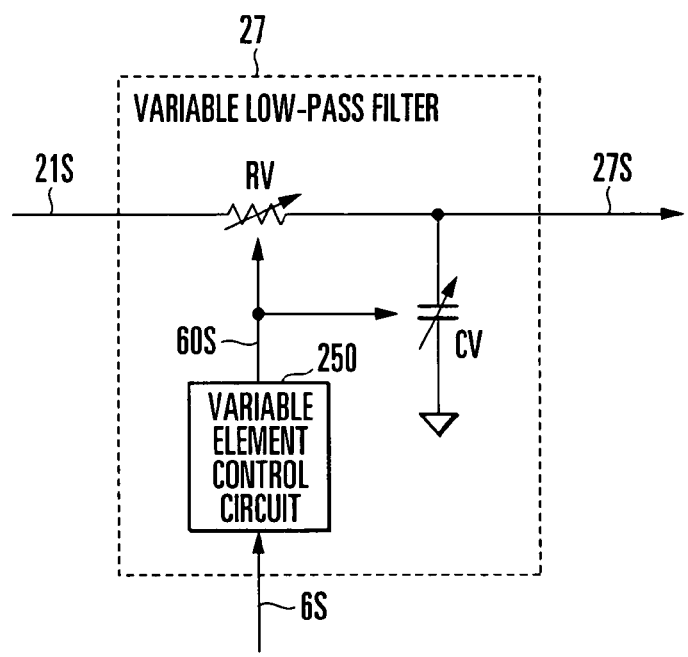
FIG. 42 is a view showing an example of the arrangement of a variable low-pass filter used in FIG. 41.

FIG. 42 shows an example of the arrangement of the variable low-pass filter 27. The variable low-pass filter 27 uses a variable resistance circuit RV and variable capacitance circuit CV in place of the resistive element R and capacitive element C of the low-pass filter in FIG. 30, respectively, and outputs a selection signal 60S from a variable element control circuit 250 in accordance with the frequency control signal 6S, thereby controlling the variable resistance circuit RV and variable capacitance circuit CV.

This allows the user of a low-pass filter with a time constant corresponding to each of the rectangular wave signals 20S having different frequencies. Even if, therefore, the frequency of the input rectangular wave signal 20S changes, a low-frequency signal 27S with a constant amplitude can be obtained. As a consequence, the supply signal 2S can be output while its amplitude is held constant.

Figure 43:
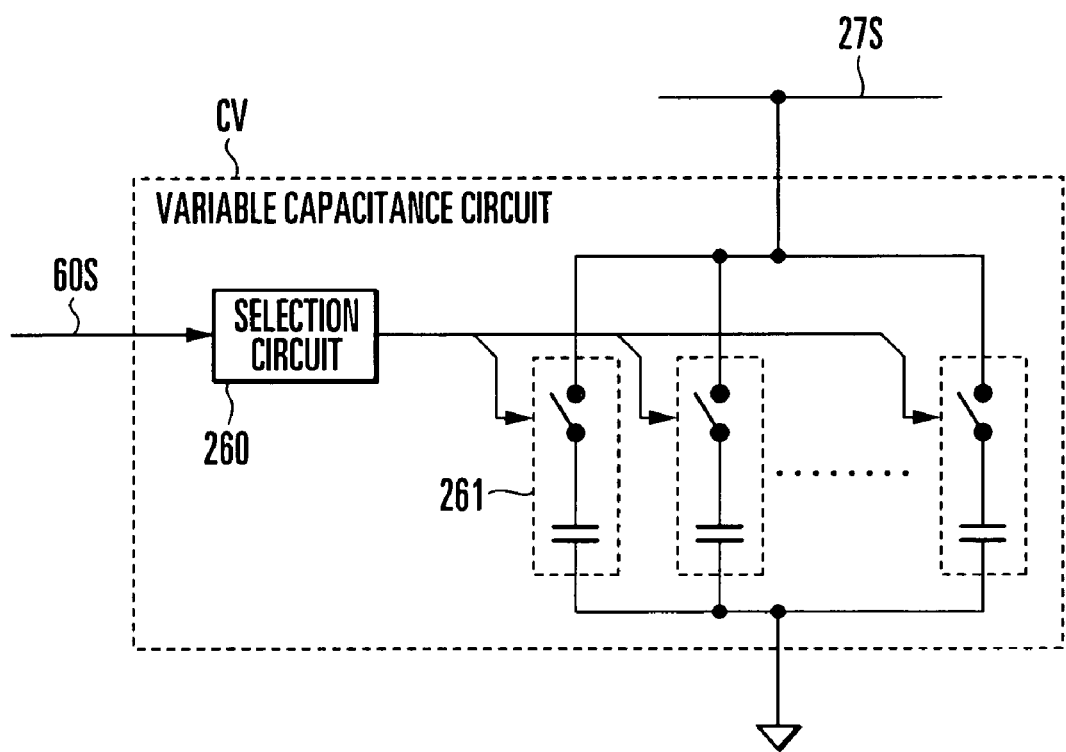
FIG. 43 is a view showing an example of the arrangement of a variable capacitance circuit used in FIG. 42.

FIG. 43 shows an example of the arrangement of the variable capacitance circuit CV. The variable capacitance circuit CV is provided with a plurality of capacitance circuits 261 each constituted by a capacitive element and switch which are connected in series with each other. At least one of the capacitance circuits 261 is selected by a selection circuit 260 on the basis of the selection signal 60S.

Note that the variable resistance circuit RV can be realized by replacing the capacitive element of the variable capacitance circuit CV with a resistive element. Although this circuit example is comprised of the variable resistance circuit RV and variable capacitance circuit CV, the circuit may have an arrangement using only capacitance or resistance which is latent in the circuit.

Figure 44A:
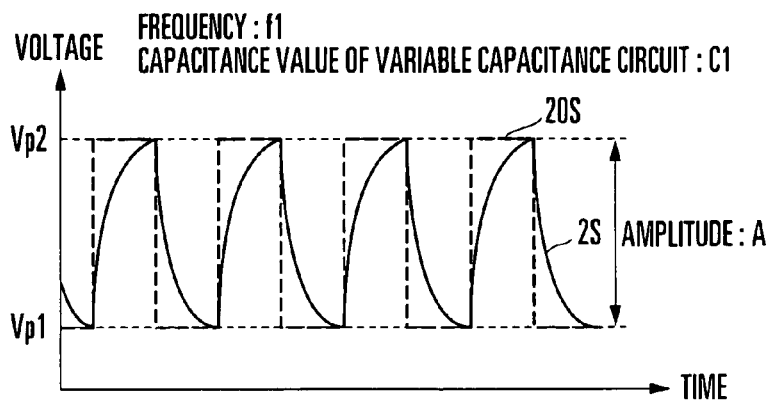
FIGS. 44A to 44C are signal waveform charts showing the operation of a supply signal generating unit in FIG. 40.
Figure 44B:
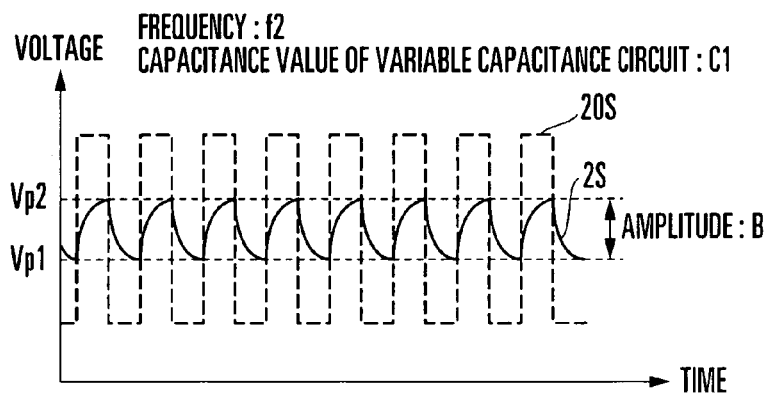
Figure 44C:
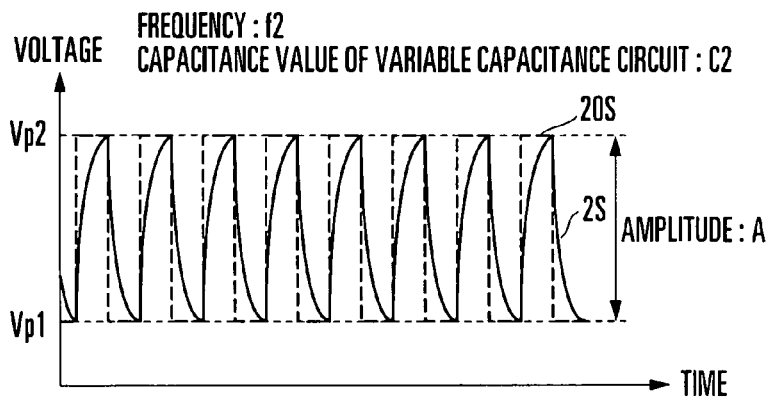

FIGS. 44A to 44C are signal waveform charts showing the operation of the waveform shaping circuit 2B. In this case, for the sake of easy understanding, assume that the resistance value of the variable resistance circuit RV is constant.

FIG. 44A shows a case wherein the rectangular wave signal 20S is a first frequency f1, and the capacitance value of the variable capacitance circuit CV is C1. Let A be the amplitude of the supply signal 2S used in this case.

FIG. 44B shows a case wherein the rectangular wave signal 20S is a second frequency f2 (f2>f1). In this case, the second frequency f2 is higher than the first frequency f1. If, therefore, the capacitance value of the variable capacitance circuit CV is kept C1, the time constant of the low-pass filter is not changed. As the frequency increases, the attenuation of the signal increases. The amplitude of the obtained supply signal 2S becomes B smaller than A.

If, therefore, the supply signal 2S changes in accordance with a change in frequency, the frequency dependence of the object 10 cannot be accurately detected by the biometric recognition unit 5.

For this reason, when the capacitance value of the variable capacitance circuit CV is changed to C2 (C2<C1) in accordance with the frequency f2, the time constant of the low-pass filter is changed. As a consequence, as shown in FIG. 44C, the supply signal 2S having the same amplitude A as that set at the first frequency f1 is obtained.

In this manner, the waveform shaping circuit 2B is provided with the variable low-pass filter 27 to adjust the time constant of the low-pass filter in accordance with the frequency control signal 6S representing the frequency of the rectangular wave signal 20S. Even if, therefore, the frequency of the rectangular wave signal 20S is changed, the supply signal 2S having a desired amplitude can be generated. This makes it possible to accurately detect the frequency dependence of the object 10 by using the biometric recognition unit 5. This in turn makes it possible to realize high-precision recognition/determination by using different measurement conditions for the object 10, thereby obtaining high security against fraudulent recognition activities using an artificial finger and the like.

The above description has exemplified the case wherein the abstracted first common potential V1 and second common potential V2 are used as operating potentials for the circuit. However, as these common potentials, arbitrary potentials can be used as long as they satisfy V2>V1. More specifically, ground potential may be used as the first common potential V1, and a power supply potential higher than ground potential may be used as the second common potential V2.

The invention claimed is:

1. A biometric recognition apparatus comprising:
a detection element which electrically contacts an object;
a supply signal generating unit which generates an AC supply signal;
a response signal generating unit which includes a resistive element connected between said supply signal generating unit and said detection element, applies the supply signal to said detection element through the resistive element, extracts, from one terminal of the resistive element, a response signal containing not less than one individual parameter which changes depending on whether or not the object is a living body, and outputs the signal;
a waveform information detection unit which detects from said response signal at least one of the individual parameters as waveform information from the response signal, and outputs a detection signal representing the waveform information; and
a biometric recognition unit which determines on the basis of the detection signal whether or not the object is a living body,
wherein the individual parameters comprise a phase and amplitude of the response signal which change in accordance with an impedance of the object with which the apparatus is in contact through said detection element,
said waveform information detection unit detects a phase difference between the supply signal and the response signal as the waveform information, and
said detection element includes a first detection electrode which electrically contacts the object and is connected to a predetermined common potential, and a second detection electrode which electrically contacts the object, said supply signal generating unit includes an offset removing circuit which outputs an AC supply signal as the supply signal from which an offset is removed to make a central potential coincide with the common potential, said response signal generating unit applies the supply signal to the second detection electrode of said detection element, and outputs a signal as a response signal which changes in phase in accordance with the impedance of the object, said waveform information detection unit includes a level shift circuit which level-shifts the response signal to make a central potential of the response signal coincide with a central potential of a reference signal synchronized with the supply signal, detects, as waveform information of the response signal, a phase difference obtained by comparing a phase of the reference signal with the response signal level-shifted by the level shift circuit, and outputs a detection signal representing the waveform information, and said biometric recognition unit determines on the basis of the waveform information of the detection signal whether or not the object is a living body.

2. A biometric recognition apparatus comprising:
a detection element which electrically contacts an object;
a supply signal generating unit which generates an AC supply signal;
a response signal generating unit which includes a resistive element connected between said supply signal generating unit and said detection element, applies the supply signal to said detection element through the resistive element, extracts, from one terminal of the resistive element, a response signal containing not less than one individual parameter which changes depending on whether or not the object is a living body, and outputs the signal;
a waveform information detection unit which detects from said response signal at least one of the individual parameters as waveform information from the response signal, and outputs a detection signal representing the waveform information; and
a biometric recognition unit which determines on the basis of the detection signal whether or not the object is a living body,
wherein the individual parameters comprise a phase and amplitude of the response signal which change in accordance with an impedance of the object with which the apparatus is in contact through said detection element,
said waveform information detection unit detects a phase difference between the supply signal and the response signal as the waveform information, and
said detection element includes a first detection electrode which electrically contacts the object and is connected to a predetermined common potential, and a second detection electrode which electrically contacts the object, said response signal generating unit applies the supply signal to the second detection electrode of said detection element, and outputs, as a response signal, a signal whose phase has changed in accordance with the impedance of the object with which the apparatus is in contact through said detection element, said waveform information detection unit includes an offset correction circuit which corrects an offset in the response signal so as to make a central potential of the response signal coincide with a predetermined reference potential used for the phase comparison, and detects, as waveform information of the response signal, a phase difference obtained by comparing a phase of a reference signal synchronized with the supply signal with a phase of the response signal corrected by the offset correction circuit, and said biometric recognition unit determines on the basis of the waveform information of the detection signal whether or not the object is a living body.

3. A biometric recognition apparatus comprising:
a detection element which electrically contacts an object;
a supply signal generating unit which generates an AC supply signal;
a response signal generating unit which includes a resistive element connected between said supply signal generating unit and said detection element, applies the supply signal to said detection element through the resistive element, extracts, from one terminal of the resistive element, a response signal containing not less than one individual parameter which changes depending on whether or not the object is a living body, and outputs the signal;
a waveform information detection unit which detects from said response signal at least one of the individual parameters as waveform information from the response signal, and outputs a detection signal representing the waveform information; and a biometric recognition unit which determines on the basis of the detection signal whether or not the object is a living body, wherein the individual parameters comprise a phase and amplitude of the response signal which change in accordance with an impedance of the object with which the apparatus is in contact through said detection element, said waveform information detection unit detects a phase difference between the supply signal and the response signal as the waveform information, said apparatus further comprising a reference potential supply unit which supplies a reference potential equal to a central potential of the supply signal to the first detection electrode of said detection element, wherein said detection element includes a first detection electrode which electrically contacts the object and is connected to a predetermined common potential, and a second detection electrode which electrically contacts the object, said response signal generating unit applies the supply signal to the second detection electrode of said detection element, and outputs, as a response signal, a signal whose phase has changed in accordance with the impedance of the object with which the apparatus is in contact through said detection element, said waveform information detection unit detects, as waveform information of the response signal, a phase difference obtained by comparing a phase of a reference signal synchronized with the supply signal with a phase of the response signal, and said biometric recognition unit determines on the basis of the waveform information of the detection signal whether or not the object is a living body.

4. A biometric recognition apparatus comprising:

a detection element which electrically contacts an object;

a supply signal generating unit which generates an AC supply signal;

a response signal generating unit which includes a resistive element connected between said supply signal generating unit and said detection element, applies the supply signal to said detection element through the resistive element, extracts, from one terminal of the resistive element, a response signal containing not less than one individual parameter which changes depending on whether or not the object is a living body, and outputs the signal;

a waveform information detection unit which detects from said response signal at least one of the individual parameters as waveform information from the response signal, and outputs a detection signal representing the waveform information; and a biometric recognition unit which determines on the basis of the detection signal whether or not the object is a living body, wherein the individual parameters comprise a phase and amplitude of the response signal which change in accordance with an impedance of the object with which the apparatus is in contact through said detection element, wherein said waveform information detection unit detects a phase difference between the supply signal and the response signal as the waveform information, and said detection element includes a first detection electrode which electrically contacts the object and is connected to a predetermined common potential, and a second detection electrode which electrically contacts the object, said supply signal generating unit includes an offset removing circuit which outputs an AC supply signal obtained by removing an offset from the supply signal so as to make a central potential of the supply signal coincide with the common potential, said response signal generating unit applies the supply signal to the second detection electrode of said detection element, and outputs, as a response signal, a signal whose amplitude has changed in accordance with the impedance of the object with which the apparatus is in contact through said detection element, said waveform information detection unit includes a maximum voltage detection circuit which detects a maximum voltage value of the response signal as the amplitude, and detects the amplitude obtained by the maximum voltage detection unit as waveform information of the response signal, and said biometric recognition unit determines on the basis of the waveform information of the detection signal whether or not the object is a living body.

5. A biometric recognition apparatus comprising:

a detection element which electrically contacts an object;

a supply signal generating unit which generates an AC supply signal;

a response signal generating unit which includes a resistive element connected between said supply signal generating unit and said detection element, applies the supply signal to said detection element through the resistive element, extracts, from one terminal of the resistive element, a response signal containing not less than one individual parameter which changes depending on whether or not the object is a living body, and outputs the signal;

a waveform information detection unit which detects from said response signal at least one of the individual parameters as waveform information from the response signal, and outputs a detection signal representing the waveform information; and a biometric recognition unit which determines on the basis of the detection signal whether or not the object is a living body, wherein the individual parameters comprise a phase and amplitude of the response signal which change in accordance with an impedance of the object with which the apparatus is in contact through said detection element, said waveform information detection unit detects a phase difference between the supply signal and the response signal as the waveform information, and said detection element includes a first detection electrode which electrically contacts the object and is connected to a predetermined common potential, and a second detection electrode which electrically contacts the object, said response signal generating unit applies the supply signal to the second detection electrode of said detection element, and outputs, as a response signal, a signal whose amplitude has changed in accordance with the impedance of the object with which the apparatus is in contact through said detection element, said waveform information detection unit includes a peak voltage detection circuit which detects a peak voltage value of the response signal, a central voltage detection circuit which detects a central voltage value of the response signal, and a voltage comparison circuit which detects an amplitude of the response signal by comparing the peak voltage value with the central voltage value, and detects the amplitude detected by the voltage comparison circuit as waveform information of the response signal, and said biometric recognition unit determines on the basis of the waveform information of the detection signal whether or not the object is a living body.

6. A biometric recognition apparatus comprising:

a detection element which electrically contacts an object;

a supply signal generating unit which generates an AC supply signal;

a response signal generating unit which includes a resistive element connected between said supply signal generating unit and said detection element, applies the supply signal to said detection element through the resistive element, extracts, from one terminal of the resistive element, a response signal containing not less than one individual parameter which changes depending on whether or not the object is a living body, and outputs the signal;

a waveform information detection unit which detects from said response signal at least one of the individual parameters as waveform information from the response signal, and outputs a detection signal representing the waveform information; and a biometric recognition unit which determines on the basis of the detection signal whether or not the object is a living body, wherein the individual parameters comprise a phase and amplitude of the response signal which change in accordance with an impedance of the object with which the apparatus is in contact through said detection element, said waveform information detection unit detects a phase difference between the supply signal and the response signal as the waveform information, and said detection element includes a first detection electrode which electrically contacts the object and is connected to a predetermined common potential, and a second detection electrode which electrically contacts the object, said response signal generating unit applies the supply signal to the second detection electrode of said detection element, and outputs, as a response signal, a signal whose amplitude has changed in accordance with the impedance of the object with which the apparatus is in contact through said detection element, said waveform information detection unit includes a maximum voltage detection circuit which detects a maximum voltage value of the response signal, a minimum detection circuit which detects a minimum voltage value of the response signal, and a voltage comparison circuit which compares the maximum voltage value with the minimum voltage value to detect the amplitude, and detects the amplitude as waveform information of the response signal, and said biometric recognition unit determines on the basis of the waveform information of the detection signal whether or not the object is a living body.

7. A biometric recognition apparatus comprising:

a detection element which electrically contacts an object;

a supply signal generating unit which generates an AC supply signal;

a response signal generating unit which includes a resistive element connected between said supply signal generating unit and said detection element, applies the supply signal to said detection element through the resistive element, extracts, from one terminal of the resistive element, a response signal containing not less than one individual parameter which changes depending on whether or not the object is a living body, and outputs the signal;

a waveform information detection unit which detects from said response signal at least one of the individual parameters as waveform information from the response signal, and outputs a detection signal representing the waveform information; and a biometric recognition unit which determines on the basis of the detection signal whether or not the object is a living body, wherein the individual parameters comprise a phase and amplitude of the response signal which change in accordance with an impedance of the object with which the apparatus is in contact through said detection element, said supply signal generating unit includes a frequency generating circuit which generates a rectangular wave signal having a predetermined frequency, and a waveform shaping circuit which extracts a desired frequency component from the rectangular wave signal generated by said frequency generating circuit as the supply signal, and generates, as the supply signal, a supply signal formed from an AC signal having a predetermined frequency, and said waveform shaping circuit includes an amplitude limiting circuit which outputs the rectangular wave signal upon limiting an amplitude thereof, a low-pass filter which extracts a desired low-frequency component from the signal obtained by the amplitude limiting circuit, and an amplification circuit which outputs the signal obtained by the low-pass filter upon amplifying the signal.

8. A biometric recognition apparatus according to claim 7, characterized in that said amplitude limiting circuit includes a first reference voltage generating circuit which generates a first reference voltage, a second reference voltage generating circuit which generates a second reference voltage, an inverter circuit which outputs the rectangular wave signal upon inverting a logical value of the signal, a first switch element which intermittently outputs the first reference voltage by performing switching operation in accordance with the signal obtained by the inverter circuit, and a second switch element which intermittently outputs the second reference voltage at a timing opposite to that of the first switch element by performing switching operation in accordance with the rectangular wave signal.

9. A biometric recognition apparatus according to claim 7, characterized in that said amplitude limiting circuit includes a first reference voltage generating circuit which generates a first reference voltage, a second reference voltage generating circuit which generates a second reference voltage, a first switch element which intermittently outputs the first reference voltage by performing switching operation in accordance with the rectangular wave signal, and a second switch element which intermittently outputs the second reference voltage at a timing opposite to that of the first switch element by performing switching operation in a phase opposite to that of the first switch element in accordance with the rectangular wave signal.

10. A biometric recognition apparatus comprising:

a detection element which electrically contacts an object;

a supply signal generating unit which generates an AC supply signal;

a response signal generating unit which includes a resistive element connected between said supply signal generating unit and said detection element, applies the supply signal to said detection element through the resistive element, extracts, from one terminal of the resistive element, a response signal containing not less than one individual parameter which changes depending on whether or not the object is a living body, and outputs the signal;

a waveform information detection unit which detects from said response signal at least one of the individual parameters as waveform information from the response signal, and outputs a detection signal representing the waveform information; and a biometric recognition unit which determines on the basis of the detection signal whether or not the object is a living body, wherein the individual parameters comprise a phase and amplitude of the response signal which change in accordance with an impedance of the object with which the apparatus is in contact through said detection element, said supply signal generating unit includes a frequency generating circuit which generates a rectangular wave signal having a predetermined frequency, and a waveform shaping circuit which extracts a desired frequency component from the rectangular wave signal generated by said frequency generating circuit as the supply signal, and generates, as the supply signal, a supply signal formed from an AC signal having a predetermined frequency, and said waveform shaping circuit includes an amplitude limiting low-pass filter which limits an amplitude of the rectangular wave signal and extracts a desired low-frequency component from the rectangular wave signal, and an amplification circuit which amplifies and outputs the signal obtained by the low-pass filter.

11. A biometric recognition apparatus according to claim 10, characterized in that said amplitude limiting low-pass filter includes a first resistive element having one terminal connected to a first common potential, a second resistive element having one terminal connected to a second common potential, a first switch element which outputs the first common potential through the first resistive element by being connected to the other terminal of the first resistive element and performing switching operation with a predetermined polarity in accordance with the rectangular wave signal, and a second switch element which intermittently outputs the second common potential through the second resistive element at a timing opposite to that of the first switch element by being connected to the other terminal of the second resistive element and performing switching operation in a phase opposite to that of the first switch element in accordance with the rectangular wave signal.

12. A biometric recognition apparatus according to claim 10, characterized in that the amplitude limiting low-pass filter includes a first reference voltage generating circuit which generates a first reference voltage, a second reference voltage generating circuit which generates a second reference voltage, a first switch element which performs switching operation upon input of the first reference voltage to a control terminal and input of the rectangular wave signal to an input terminal, and a second switch element which performs switching operation in a phase opposite to that of the first switch element upon input of the second reference voltage to a control terminal and connection of an output terminal of the first switch element to an input terminal.

13. A biometric recognition apparatus comprising:

a detection element which electrically contacts an object;

a supply signal generating unit which generates an AC supply signal;

a response signal generating unit which includes a resistive element connected between said supply signal generating unit and said detection element, applies the supply signal to said detection element through the resistive element, extracts, from one terminal of the resistive element, a response signal containing not less than one individual parameter which changes depending on whether or not the object is a living body, and outputs the signal;

a waveform information detection unit which detects from said response signal at least one of the individual parameters as waveform information from the response signal, and outputs a detection signal representing the waveform inflation; and a biometric recognition unit which determines on the basis of the detection signal whether or not the object is a living body, wherein the individual parameters comprise a phase and amplitude of the response signal which change in accordance with an impedance of the object with which the apparatus is in contact through said detection element, said supply signal generating unit includes a frequency generating circuit which generates a rectangular wave signal having a predetermined frequency, and a waveform shaping circuit which extracts a desired frequency component from the rectangular wave signal generated by said frequency generating circuit as the supply signal, and generates, as the supply signal, a supply signal formed from an AC signal having a predetermined frequency, said apparatus further comprising a frequency control unit which outputs a frequency control signal which designates a frequency of the supply signal, wherein said frequency generating circuit outputs a rectangular wave signal having a frequency corresponding to the frequency control signal, and said waveform shaping circuit extracts a frequency component corresponding to the frequency control signal from the rectangular wave signal and outputs the frequency component as the supply signal, wherein said variable low-pass filter includes a variable resistive element which changes a resistance value in accordance with the frequency control signal upon input of the rectangular wave signal to one terminal, and a variable capacitive element which changes a capacitance value in accordance with the frequency control signal upon being connected between the other terminal of the variable resistive element and a predetermined low impedance potential.

* * * * *